US006696557B1

(12) United States Patent
Caras

(10) Patent No.: US 6,696,557 B1
(45) Date of Patent: Feb. 24, 2004

(54) AL-2 NEUROTROPHIC FACTOR NUCLEIC ACID

(75) Inventor: Ingrid W. Caras, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 234 days.

(21) Appl. No.: 08/635,130

(22) Filed: Apr. 19, 1996

(51) Int. Cl.$^7$ ................................................ C07H 21/04
(52) U.S. Cl. ...................................... 536/23.4; 435/69.7
(58) Field of Search .......................... 435/6, 69.1, 69.4, 435/69.7, 70.1, 71.1, 71.2, 91.1, 91.4, 320.1; 536/23.1, 23.4, 23.5, 23.51, 24.31, 25.3

(56) References Cited

FOREIGN PATENT DOCUMENTS

| WO | WO 95/27060 | 12/1995 |
| WO | WO 97/15667 | 1/1997 |

OTHER PUBLICATIONS

Hiller et al, the WashU–Merck EST Project, Accession H 10006 NID g 874828, Jun. 23, 1995.*
Bowe etal. Science, 247: 1306–1310, 1990.*
Ngo etal"The Protein Folding Problem and Tertary Structure Prediction", 1994 Merzer(ed.) pp. 433 and 492–495.*
Frommel et al, J.Mcl. Evol 21 p. 233–257, 1985.*
Burgess etal, The Journal of Cell Biology 111:2129–2138, 1990.*
Lazar et al, Molecular and Celluar Biology, 8(3): 1247–1252, 1988.*
Davis et al., "Ligands for EPH–Related Receptor Tyrosine Kinases That Require Membrane Attachment or Clustering for Activity" *Science* 266:816–819 (Nov. 4, 1994).
Gale et al., "Elk–L3, A Novel Transmembrane Ligand for the Eph Family of Receptor Tyrosine Kinases, Expressed in Embryonic Floor Plate, Roof Plate and Hindbrain Segments" *Oncogene* 13:1343–1352 (1996).
Hillier et al., "EMBL Database Entry HS006163" *The WashU–Merck EST Project* (Accession No. H10006) (Jul. 2, 1995).
Hillier et al., "EMBL Database Entry Hsu57001" *LERK–8, A Ligand for the EPH–Related Receptor Tyrosine Kinases* (Accession No. U57001) (Jul. 31, 1996).
Tang et al., "cDNA Cloning, Chromosomal Localization, and Expression Pattern of EPLG8, A New Member of the EPLG Gene Family Encoding Ligands of EPH–Related Protein–Tyrosine Kinase Receptors" *Genomics* 41:17–24 (1997).
Winslow et al., "Cloning of AL–1, a Ligand for an Eph–Related Tyrosine Kinase Receptor Involved in Axon Bundle Formation" *Neuron* 14:973–981 (May 1995).

* cited by examiner

*Primary Examiner*—Patricia A. Duffy
(74) *Attorney, Agent, or Firm*—Atulya Agarwal; Ginger R. Dreger, Esq.; Heller Ehrman White & McAuliffe LLP

(57) ABSTRACT

The present invention provides nucleic acids encoding AL-2 protein, host cells and vectors containing these nucleic acids, and methods for their use to produce AL-2 protein by recombinant DNA methods.

2 Claims, 15 Drawing Sheets

| | | | | | |
|---|---|---|---|---|---|
| 1 | GNTCTAGAANTA | GTGGATCCCCCC | GGGCTGCAGGAA | TTCCGACGGCCC | CTGGAAGGGCTC | TGGTGGGGCTGA |
| | CNAGATCTTNAT | CACCTAGGGGGG | CCCGACGTCCTT | AAGGCTGCCGGG | GACCTTCCCGAG | ACCACCCCGACT |
| 73 | GCGCTCTGCCGC | GGGGGCGGGGC | ACAGCAGGAAGC | AGGTCCGCGTGG | GCGCTGGGGGCA | TCAGCTACCGGG |
| | CGCGAGACGGCG | CCCCGCGCCCG | TGTCGTCCTTCG | TCCAGGCGCACC | CGCGACCCCGT | AGTCGATGGCCC |
| 145 | GTGGTCCGGGCT | GAAGAGCCAGGC | AGCCAAGGCAGC | CACCCCGGGGGG | TGGGCGACTTTG | GGGGAGTTGGTG |
| | CACCAGGCCCGA | CTTCTCGGTCCG | TCGGTTCCGTCG | GTGGGGCCCCCC | ACCCGCTGAAAC | CCCCTCAACCAC |
| 217 | CCCCGCCCCCCA | GGCCTTGGCGGG | GTCATGGGGCCC | CCCCATTCTGGG | CCGGGGGGCGTG | CGAGTGGGGGCC |
| | GGGGCGGGGGGT | CCGAACCGCCC | CAGTACCCCGG | GGGGTAAGACCC | GGCCCCCGCAC | GCTCAGCCCCGG |
| 1 | | | MetGlySerGly | ProHisSerGly | ProGlyGlyVal | ArgValGlyAla |
| 289 | CTGCTGCTGCTG | GGGGTTTTGGGG | CTGGTGTCTGGG | CTCAGCCTGGAG | CCTGTCTACTGG | AACTCGGCGAAT |
| | GACGACGACGAC | CCCCAAAACCCC | GACCAGAGACCC | GAGTCGGACCTC | GGACAGATGACC | TTGAGCGCTTA |
| 16 | LeuLeuLeuLeu | GlyValLeuGly | LeuSerLeuGly | LeuSerLeuGlu | ProValTyrTrp | AsnSerAlaAsn |
| 361 | AAGAGGTTCCAG | GCAGAGGGTGGT | TATGTGCTGTAC | CCTCAGATCGGG | GACCGGCTAGAC | CTGCTCTGCCCC |
| | TTCTCCAAGGTC | CGTCTCCCACCA | ATACACGACATG | GGAGTCTAGCCC | CTGGCCGATCTG | GACGAGACGGGG |
| 40 | LysArgPheGln | AlaGluGlyGly | TyrValLeuTyr | ProGlnIleGly | AspArgLeuAsp | LeuLeuCysPro |
| 433 | CGGGCCCGGCCT | CCTGGCCCTCAC | TCCTCTCCTAAT | TATGAGTTCTAC | AAGCTGTACCTG | GTAGGGGGTGCT |
| | GCCCGGGCCGGA | GGACCGGGAGTG | AGGAGAGGATTA | ATACTCAAGATG | TTCGACATGGAC | CATCCCCACGA |
| 64 | ArgAlaArgPro | ProGlyProHis | SerSerProAsn | TryGluPheTyr | LysLeuTyrLeu | ValGlyGlyAla |
| 505 | CAGGGCCCGGCGC | TGTGAGGCACCC | CTGCCCCAAAC | CTCCTTCTCACT | TGTGATCGCCCA | GACCTGGATCTC |
| | GTCCCGGCCGCG | ACACTCCGTGGG | GGACGGGGTTTG | GAGGAAGAGTGA | ACACTAGCGGGT | CTGGACCTAGAG |
| 88 | GlnGlyArgArg | CysGluAlaPro | ProAlaProAsn | LeuLeuLeuThr | CysAspArgPro | AspLeuAspLeu |
| 577 | CGCTTCACCATC | AAGTTCCAGGAG | TATAGCCCTAAT | CTCTGGGGCCAC | GAGTTCCGCTCG | CACCACGATTAC |
| | GCGAAGTGGTAG | TTCAAGGTCCTC | ATATCGGGATTA | GAGACCCCGGTG | CTCAAGGCGAGC | GTGGTGCTAATG |
| 112 | ArgPheThrIle | LysPheGlnGlu | TyrSerProAsn | LeuTrpGlyHis | GluPheArgSer | HisHisAspTyr |

```
1297  ATACAACTGTTT TTCATGCGATCC AAGTGCTCCCGT GTCACTACATTC TTATTTCCTGTG CAAGTTATTACG
      TATGTTGACAAA AAGTACGCTAGG TTCACGAGGGCA CAGTGATGTAAG AATAAAGGACAC GTTCAATAATGC
352   IleGlnLeuPhe PheMetArgSer LysCysSerArg ValThrThrPhe LeuPheProVal GlnValIleThr

1369  ACATCGACTTGC CGGATGACTTCA TTTAGCTTTACC ACCCTGAACCCA TCCATGCAGGCC TGCAGAGCACAG
      TGTAGCTGAACG GCCTACTGAAGT AAATCGAAATGG TGGGACTTGGGT AGGTACGTCCGG ACGTCTCGTGTC
376   ThrSerThrCys ArgMetThrSer PheSerPheThr ThrLeuAsnPro SerMetGlnAla CysArgAlaGln

1441  ATGGGGGAATTC CGAATCAGATGG TGTTTCTGGGGG GACAGGATCCTG GGTACGGCTCTG TTTGTGCTTGTG
      TACCCCCTTAAG GCTTAGTCTACC ACAAAGACCCCC CTGTCCTAGGAC CCATGCCGAGAC AAACACGAACAC
400   MetGlyGluPhe ArgIleArgTrp CysPheTrpGly AspArgIleLeu GlyThrAlaLeu PheValLeuVal

1513  CTTATTCTTCTT CTTGGGAGGCTG AATATGCATCAG ACGACACTGCTC CGGCAACGGGCC AGTGTGGAGGCG
      GAATAAGAAGAA GAACCCTCCGAC TTATACGTAGTC TGCTGTGACGAG GCCGTTGCCCGG TCACACCTCCGC
424   LeuIleLeuLeu LeuGlyArgLeu AsnMetHisGln ThrThrLeuLeu ArgGlnArgAla SerValGluAla

1585  GAAGCCGGCCAG CATGGTCCCCTG TGATAGGATTGA AAGAGCTACTGA GAATAGGGGGCT TCTCAATGAGAG
      CTTCGGCCGGTC GTACCAGGGGAC ACTATCCTAACT TTCTCGATGACT CTTATCCCCCGA AGAGTTACTCTC
448   GluAlaGlyGln HisGlyProLeu (SEQ ID NO: 2)

1657  AGCGGAGGCTGC TGTTATCATGGG AACCAGGCAGAT CAATCATCCCTG GCAGGTCAGGCA GGAAGTTACTTA
      TCGCCTCCGACG ACAATAGTACCC TTGGTCCGTCTA GTTAGTAGGGAC CGTCCAGTCCGT CCTTCAATGAAT

1729  GCTTCTCCTTCA CCTTCTTCCCAC AGAATTTATTAT AGGCTTGTTCCA AGTTGTAGTGTG TGATCAGATTCG
      CGAAGAGGAAGT GGAAGAAGGGTG TCTTAAATAATA TCCGAACAAGGT TCAACATCACAC ACTAGTCTAAGC

1801  TGCTGCCTGTCA GCTCTGTGCTAC CTGGCAGTTCCC CTCATGGAATTC GATATCAAGCTT ATCGATACCGTC
      ACGACGGACAGT CGAGACACGATG GACCGTCAAGGG GAGTACCTTAAG CTATAGTTCGAA TAGCTATGGCAG

1873  GACCT (SEQ ID NO: 1)
      CTGGA
```

```
  1  GNTCTAGAANTA GTGGATCCCCCC GGGCTGCAGGAA TTCCGACGGCCC CTGGAAGGGCTC TGGTGGGGCTGA
     CNAGATCTTNAT CACCTAGGGGGG CCCGACGTCCTT AAGGCTGCCGGG GACCTTCCCGAG ACCACCCCGACT

73  GCGCTCTGCCGC GGGGGGGCGGGC ACAGCAGGAAGC AGGTCCGGGGCA GCGCTGGGGGCC TCAGCTACCGGG
     CGCGAGACGGCG CCCCCCGCCCCG TGTCGTCCTTCG TCCAGGCGCACC CGCGACCCCCGT AGTCGATGGCCC

145  GTGGTCCGGGCT GAAGAGCCAGGC AGCCAAGGCAGC CACCCCGGGGGG TGGGGACTTTG GGGGAGTTGGTG
     CACCAGGCCCGA CTTCTCGGTCCG TCGGTTCCGTCG GTGGGGCCCCCC ACCCGCTGAAAC CCCCTCAACCAC

217  CCCCGCCCCCA GGCCTTGGCGGG GTCATGGGGCCC CCCCATTCTGGG CCGGGGGGCGTG CGAGTCGGGGCC
     GGGGCGGGGGT CCGGAACCGCCC CAGTACCCCGGG GGGGTAAGACCC GGCCCCCGCAC GCTCAGCCCCGG
                                           MetGlyPro      ProHisSerGly  ProGlyGlyVal  ArgValGlyAla
                                             1

289  CTGCTGCTGCTG GGGGTTTTGGGG CTGGTGTCTGGG CTCAGCCTGGAG CCTGTCTACTGG AACTCGGCGAAT
     GACGACGACGAC CCCCAAAACCCC GACCACAGACCC GAGTCGGACCTC GGACAGATGACC TTGAGCCGCTTA
     LeuLeuLeuLeu GlyValLeuGly LeuSerLeuGlu LeuSerLeuGlu ProValTyrTrp AsnSerAlaAsn
     16

361  AAGAGGTTCCAG GCAGAGGGTGGT TATGTGCTGTAC CCTCAGATCGGG GACCGGCTAGAC CTGCTCTGCCCC
     TTCTCCAAGGTC CGTCTCCCACCA ATACACGACATG GGAGTCTAGCCC CTGGCCGATCTG GACGAGACGGGG
     LysArgPheGln AlaGluGlyGly TyrValLeuTyr ProGlnIleGly AspArgLeuAsp LeuLeuCysPro
     40

433  CGGGCCCCGGCT CCTGGCCCCTCAC TCCTCTCCTAAT TATGAGTTCTAC AAGCTGTACCTG GTAGGGGGTGCT
     GCCCGGGGCCGA GGACCGGGGAGTG AGGAGGATTA ATACTCAAGATG TTCGACATGGAC CATCCCCCACGA
     ArgAlaArgPro ProGlyProHis SerSerProAsn TyrGluPheTyr LysLeuTyrLeu ValGlyGlyAla
     64

505  CAGGGCCGGCGC TGTGAGGCACCC CCTGCCCCAAAC CTCCTTCTCACT TGTGATCGCCCA GACCTGGATCTC
     GTCCCGGCCGCG ACACTCCGTGGG GGACGGGGTTTG GAGGAAGAGTGA ACACTAGCGGGT CTGGACCTAGAG
     GlnGlyArgArg CysGluAlaPro ProAlaProAsn LeuLeuLeuThr CysAspArgPro AspLeuAspLeu
     88

577  CGCTTCACCATC AAGTTCCAGGAG TATAGCCCTAAT CTCTGGGCCAC GAGTTCCGCTCG CACCACGATTAC
     GCGAAGTGGTAG TTCAAGGTCCTC ATATCGGGATTA GAGACCCGGTG CTCAAGGCGAGC GTGGTGCTAATG
     ArgPheThrIle LysPheGlnGlu TyrSerProAsn LeuTrpGlyHis GluPheArgSer HisHisAspTyr
     112
```

FIG. 2A

```
649   TACATCATTGCC ACATCGGATGGG ACCCGGGAGGGC CTGGAGAGCCTG CAGGGAGGTGTG TGCCTAACCAGA
      ATGTAGTAACGG TGTAGCCTACCC TGGGCCCTCCCG GACCTCTCGGAC GTCCCTCCACAC ACGGATTGGTCT
136   TyrIleIleAla  ThrSerAspGly  ThrArgGluGly  LeuGluSerLeu  GlnGlyGlyVal  CysLeuThrArg

721   GGCATGAAGGTG CTTCTCCGAGTG GGACAAAGTCCC CGAGGAGGGGCT GTCCCCCGAAAA CCTGTGTCTGAA
      CCGTACTTCCAC GAAGAGGCTCAC CCTGTTTCAGGG GCTCCTCCCCGA CAGGGGGCTTTT GGACACAGACTT
160   GlyMetLysVal  LeuLeuArgVal  GlyGlnSerPro  ArgGlyGlyAla  ValProArgLys  ProValSerGlu

793   ATGCCCATGGAA AGAGACCGAGGG GCAGCCCACAGC CTGGAGCCTGGG AAGGAGAACCTG CCAGGTGACCCC
      TACGGGTACCTT TCTCTGGCTCCC CGTCGGGTGTCG GACCTCGGACCC TTCCTCTTGGAC GGTCCACTGGGG
184   MetProMetGlu  ArgAspArgGly  AlaAlaHisSer  LeuGluProGly  LysGluAsnLeu  ProGlyAspPro

865   ACCAGCAATGCA ACCTCCCGGGGT GCTGAAGGCCCC CTGCCCCCTCCC AGCATGCCTGCA GTGGCTGGGGCA
      TGGTCGTTACGT TGGAGGGCCCCA CGACTTCCGGGG GACGGGGGAGGG TCGTACGGACGT CACCGACCCCGT
208   ThrSerAsnAla  ThrSerArgGly  AlaGluGlyPro  LeuProProPro  SerMetProAla  ValAlaGlyAla

937   GCAGGGGGGCTG GCGCTGCTCTTG CTGGGCGTGGCA GGGGCGTGGGGT GCCATGTGTTGG CGGAGACGGCGG
      CGTCCCCCCGAC CGCGACGAGAAC GACCCGCACCGT CCCCGCACCCCA CGGTACACAACC GCCTCTGCCGCC
232   AlaGlyGlyLeu  AlaLeuLeuLeu  LeuGlyValAla  GlyAlaGlyGly  AlaMetCysTrp  ArgArgArgArg

1009  GCCAAGCCTTCG GAGAGTCGCCAC CCTGTCGTCCTGGC TCCTTCGGGAGG GAGGGTCTCTG GGCCTGGGGGGT
      CGGTTCGGAAGC CTCTCAGCGGTG GGACCAGGACCG AGGAAGCCCTCC CCTCCCAGAGAC CCGGACCCCCA
256   AlaLysProSer  GluSerArgHis  ProGlyProGly  SerPheGlyArg  GlyLySerLeu   GlyLeuGlyGly

1081  GGAGGTGGGATG GGACCTCGGGAG GCTGAGCCTGGG GAGCTAGGGATA GCTCTGCGGGGT GGGGGGCTGCA
      CCTCCACCCTAC CCTGGAGCCCTC CGACTCGGACCC CTCGATCCCTAT CGAGACGCCCCA CCGCCCGACGT
280   GlyGlyGlyMet  GlyProArgGlu  AlaGluProGly  GluLeuGlyIle  AlaLeuArgGly  GlyGlyAlaAla

1153  GATCCCCCCTTC TGCCCCCACTAT GAGAAGGTGAGT GGTGACTATGGG CATCCTGTGTAT ATCGTGCAGGAT
      CTAGGGGGGAAG ACGGGGGTGATA CTCTTCCACTCA CCACTGATACCC GTAGGACACATA TAGCACGTCCTA
304   AspProProPhe  CysProHisTyr  GluLysValSer  GlyAspTyrGly  HisProValTyr  IleValGlnAsp

1225  GGGCCCCCCCAG AGCCCTCCAAAC ATCTACTACAAG GTATGAGGGCTC TTGGAGTGGCCC ATATTGCATACG
      CCCGGGGGGGTC TCGGGAGGTTTG TAGATGATGTTC CATACTCCCGAG AACCTCACCGGG TATAACGTATGC
328   GlyProProGln  SerProProAsn  IleTyrTyrLys  ValOP*   (SEQ ID NO: 4)
```

FIG. 2B

```
1297  AGCCCTTCTGG  GGTGCTCCTCCA  GTTTAATTCCTG  GTTTGAGGGACA  CCTCTAACATCT  CGGCCCCCTGTG
      TCGGGAAGAACC  CCACGAGGAGGT  CAAATTAAGGAC  CAAACTCCCTGT  GGAGATTGTAGA  GCCGGGGGACAC

1369  CCCCCCAGCCC  CTTCACTCCTCC  CGGCTGCTGTCC  TCGTCTCCACTT  TTAGGATTCCTT  AGGATTCCCACT
      GGGGGGTCGGG  GAAGTGAGGAGG  GCCGACGACAGG  AGCAGAGGTGAA  AATCCTAAGGAA  TCCTAAGGGTGA

1441  GCCCCACTTCCT  GCCCTCCCGTTT  GGCCATGGGTGC  CCCCCTCTGTCT  CAGTGTCCCTGG  ATCCTTTTTCCT
      CGGGGTGAAGGA  CGGGAGGGCAAA  CCGGTACCCACG  GGGGAGACAGA   GTCACAGGGACC  TAGGAAAAGGA

1513  TGGGGAGGGGCA  CAGGCTCAGCCT  TGACCCAGGCCA  CCTTGTCCCCCT  CACCCACCCAGA  CACCCACCCAGA
      ACCCCTCCCCGT  GTCGAGTCGGA   ACTGGGTCCGTA  GGAACAGGGGGA  GTGGGTGGGTCT

1585  GCTAGGGGCGGG  AACAGCCCACCT  TTTGGTTGGCAC  CGCCCTTCTTTCT  GCCTCTCACTGG  TTTTCTCTCTC
      ACCCCTCCCCGCC  CGATCCCCGCCC  TTGTGGGTGGA  AAACCAACCGTG  GCGGAAGAAAGA  CGGAGAGTGACC  AAAGAGAAGAG

1657  TATCTCTTATTC  TTTCCCTCTCTT  CCGTCTCTAGGT  CTGTTCTCTTCC  CCTAGCATCCTC  CTCCCCACATCT
      ATAGAGAATAAG  AAAGGAGAGAA   GGCAGAGATCCA  GACAAGAGAAG   GGATCGTAGGAG  GAGGGGTGTAGA

1729  CCTTTCACCCTC  TTGGCTTCTTAT  CCTGTGCCCTC   CCATCTCCTCTGGG  TGGGGGCATCAA  AGCATTTCTCCC
      GGAAAGTGGGAG  AACCGAAGAATA  GGACACGGAGAG  GGTAGAGGACCC   ACCCCCGTAGTT  TCGTAAAGAGGG

1801  CTTAGCTTTCAG  CCCCCCTTCTGA  CCTCTCATACCA  CCACTCCCCTC    AGTCTGCCAAAA  ATGGGGCCCTTA
      GAATCGAAAGTC  GGGGGAAGACT   GGAGAGTATGGT  TGGTGAGGGAG   TCAGACGGTTTT  TACCCCCGGAAT

1873  TGGGAAGGCTC  TGACACTCCACC  CCAGCTCAGGCC  ATGGGCACCAGG  GCTCCATTCTCT  GGCCTGGCCAG
      ACCCCTTCCGAG  ACTGTGAGGTGG  GGTCGAGTCCGG  TACCCGTCGTCC  CGAGGTAAGAGA  CCGGACCGGTC

1945  GCCTCTACATAC  TTACTCCAGCCA  TTTGGGGTGGTT  GGGTCATGACAG  CTACCATGAGAA  GAAGTGTCCGT
      CGGAGATGTATG  AATGAGGTCGGT  AAACCCCACCAA  CCCAGTACTGTC  GATGGTACTCTT  CTTCACAGGGCA

2017  TTTGTCCSGTGG  CCAATAGCAAGA  TATGAACCGGTC  GGGACATGTATG  GACTTGGTCTGA  TGCTGAATGGGC
      AACAGGTCACC   GGTTATCGTTCT  ATACTTGGCCAG  CCCTGTACATAC  CTGAACCAGACT  ACGACTTACCCG
```

FIG. 2C

```
2089  CACTTGGGACCG GAAGTGACTTGC TCCAGACAAGAG GTGACCAGGCCC GGACAGAAATGG CCTGGGAAGTAG
      GTGAACCCTGGC CTTCACTGAACG AGGTCTGTTCTC CACTGGTCCGGG CCTGTCTTACC GGACCCTTCATC

2161  CAGAAGCAGTGC AGCAGGAACTGG AAGTGCCTTCAT CCAGGACAGGAA GTAGCACTTCTG AAACAGGAAGTG
      GTCTTCGTCACG TCGTCCTTGACC TTCACGGAAGTA GGTCCTGTCCTT CATCGTGAAGAC TTTGTCCTTCAC

2233  GTCTGGCTGGAA CTCCAAGTGGCT TAGTCTGGGGGA TCAGGAGGTGGG AGGTGGATGGTT CTTATTCTGTGG
      CAGACCGACCTT GAGGTTCACCGA ATCAGACCCCCT AGTCCTCCACCC TCCACCTACCAA GAATAAGACACC

2305  AGAAGAAGGGCG GGAAGAACTTCC TTTCAGGAGGAA GCTGGAACTTAC TGACTGTAAGAG GTTAGAGGTGGA
      TCTTCTTCCCGC CCTTCTTGAAGG AAAGTCCTCCTT CGACCTTGAATG ACTGACATTCTC CAATCTCCACCT

2377  CCGA (SEQ ID NO: 3)
      GGCT
```

FIG. 2D

| FIG. 2A |
| FIG. 2B |
| FIG. 2C |
| FIG. 2D |

```
AL-2b.L  751  AGT CCCCGAGGAGGGGCTGTGTCCCCGAAAACCTGTGTCTGAAATGCCCAT
H10006   243  AGT CCCCGAGGAGGGGCTGTGTCCCCGAAAACCTGTGTCTGAAATGCCCAT

AL-2b.L  801  GGAAAGAGACCGAGGGGCAGCCCACAGCCT GGAGCCT GGGAAGGAGAA
H10006   292  GGAAAGAGACCGAGGGGCAGCCCACAGCCT GGAGCCT GGGAAGGAGAA

AL-2b.L  849  CCTGCCAGGTGACCCCACCAGCAAT GCAACCTC CCGGGGT   GCT GAAGG
H10006   342  CCTGCCAGGTGACCCCACCAGCAAT NCAACCT T CCGGGGT TGCT GAAGG

AL-2b.L  897  C CCCT   G CCCC TCCCAGCA TGCC TGCAGT   GGCT GGGGCAGCAGG
H10006   392  G CCCCT T GACCCT T CCCAGCAT TGCAN TGCN TGGT TNGGGCAGCAN G

AL-2b.L  942  GGGGC     TGGCGCTGCTCTTGCTGGGCGTGCAGGGGCTGGGGGTGCC
H10006   442  GGGGN GTTTT TGGC (SEQ ID NO: 5)

AL-2b.L  988  ATGTGTTGGCGGAGACGGGCCAAGCCCTTCGGAGAGTCGCCACCCTGG

AL-2b.L 1038  TCCTGGCTCCTTCGGGAGGGGAGGGTCTCTGGGCCTGGGGGTGGAGGTG

AL-2b.L 1088  GGATGGGACCCTCGGGAGGCTGAGCCTGGGAGCTAGGGATAGCTCTGCGG

AL-2b.L 1138  GGTGGCGGGGGCTGCAGATCCCCCCCTTCTGCCCCACTATGAGAAGGTGAG

AL-2b.L 1188  TGGTGACTATGGGCATCCTGTGTATATCGTGCAGGATGGCCCCCCAGA

AL-2b.L 1238  GCCCTCCAAACATCTACTACACATCGATTTCTGTGTTGGAGTGGCCCATA

AL-2b.L 1288  TTGCATACGATACAACTGTTTTCATGCGATCCAAGTGCTCCCCGTGTCAC
```

FIG. 3B

```
AL-2b.L1338  TACATTCTTATTTCCTGTGCAAGTTATTACGACATCGACTTGCCGGATGA
AL-2b.L1388  CTTCATTTAGCTTTACGACCCTGAACCCATCCATGCAGGCCTGCAGAGCA
AL-2b.L1438  CAGATGGGGGAATTCCGAATCAGATGGTGTTTCTGGGGGGACAGGATCCT
AL-2b.L1488  GGGTACGGCTCTGTTTGTGCTTGTGCTTATTCTTCTTCTTGGGAGGCTGA
AL-2b.L1538  ATATGCATCAGACGACAGTGCTCCGGCAACGGGCCAGTGTGGAGGCGGAA
AL-2b.L1588  GCCGGCCAGCATGGTCCGCTGTGATAGGATTGAAAGAGCTACTGAGAATA
AL-2b.L1638  GGGGGCTTCTCAATGAGAGCGGAGGCTGTGTTATCATGGGAACCAGG
AL-2b.L1688  CAGATCAATCATCCCTGGCAGGTCAGGCAGGAAGTTACTTAGCTTCTCCT
AL-2b.L1738  TCACCTTCTTCCCACAGAATTTATTATAGGCTTGTTCCAAGTTGTAGTGT
AL-2b.L1788  GTGATCAGATTCGTGCTGCCCTGTCAGCTCTGTGCTACCTGGCAGTTCCC
AL-2b.L1838  TCATGGAATTCGATATCAAGCTTATCGATACCGTCGACCT (SEQ ID NO: 1)
```

| FIG. 3A |
| FIG. 3B |
| FIG. 3C |

```
lerk2       1  MA-RPGQRWLGKWLVAMVVWALCRLATPLAKNLEPVSMSSLNPKFLSGKG
huHTKL      1  MAVRRDSVWKYCWGVLMV---LCRTAISKSIVLEPLYWNSSNSKFLPGQG
AL2.sht     1  MG-PPHSGPGGVRVGALLLGVLGLVSGL--SLEPVYWNSANKRFQAEGG
AL2.long    1  MG-PPHSGPGGVRVGALLLGVLGLVSGL--SLEPVYWNSANKRFQAEGG lerk2      50  LVLYPKIGDKLDIICPRA---EAGR--PYEYYKLYLVRPEQAACSTVLD
huHTKL     48  LVLYPQIGDKLDIICPKV---DSKTVGQYEYYKYYMVDKDQADRCTIKKE
AL2.sht    48  YVLYPQIGDRLDLLCPRARPPGPHSSPNYEFYKLYLVGGAQGRRCEAPPA
AL2.long   48  YVLYPQIGDRLDLLCPRARPPGPHSSPNYEFYKLYLVGGAQGRRCEAPPA lerk2      95  PNVLVTCNRPEQEIRFTIKFQEFSPNYMGLEFKKHHDYYITSTSNGSLEG
huHTKL     95  NTPLLNCAKPDQDIKFTIKFQEFSPNLWGLEFQKNKDYYIISTSNGSLEG
AL2.sht    98  PNLLLTCDRPDLDLRFTIKFQEYSPNLWGHEFRSHHDYYIIATSDGTREG
AL2.long   98  PNLLLTCDRPDLDLRFTIKFQEYSPNLWGHEFRSHHDYYIIATSDGTREG lerk2     145  LENREGGVCRTRTMKIIMKVGQDPNAVTPEQLTTSRPSKEADNTVKMATQ
huHTKL    145  LDNQEGGVCQTRAMKILMKVGQDASS----AGSTRNKDPTRRPELEAG
AL2.sht   148  LESLQGGVCLTRGMKVLLRVGQSPRGGAVPRKPVSEMPMERDRGAAHSLE
AL2.long  148  LESLQGGVCLTRGMKVLLRVGQSPRGGAVPRKPVSEMPMERDRGAAHSLE
```

FIG. 4A

```
lerk2      195 APGSRGSLGDSDGKHETVNQEEKSGPGASGGSSGDPDGFFNSKVALFAAV
huHTKL     189 TNG-RSSTTSPFVKPNPGSSTDGNSAGHSG----NNILGSEVALFAGI
AL2.sht    198 -PGKENLPGDPTSNATSRGAEGPLPPPSMPAVAGAAGGL---ALLLGVA
AL2.long   198 -PGKENLPGDPTSNATSRGAEGPLPPPSMPAVAGAAGGL---ALLLGVA lerk2      245 GAGCVIFLLIIIFLTVLLLKLRHRHRKHTQ-QRAAALSLSTLASPKGGSG
huHTKL     232 ASGCIIFIVILITLVLLLKYRRHRHRKHSP-QHTTTLSLSTLATPKRSGN
AL2.sht    244 GAGGA--------MCWRRRAKPSESRHPGPGSFGRGGSLGLGG---GGGMG
AL2.long   244 GAGGA--------MCWRRRAKPSESRHPGPGSFGRGGSLGLGG---GGGMG lerk2      294 TAGTEPSDIIIPLR---TTENNYCPHYEKVSGDYGHPVYIVQEMPPQSPA
huHTKL     261 NNGSEPSDIIIPLR---TADSVFCPHYEKVSGDYGHPVYIVQEMPPQSPA
AL2.sht    265 PREAEPGELGIALRGGGAADPPFCPHYEKVSGDYGHPVYIVQDGPPQSPP
AL2.long   265 PREAEPGELGIALRGGGAADPPFCPHYEKVSGDYGHPVYIVQDGPPQSPP lerk2      341 NIYY-------------------------------------------
huHTKL     328 NIYY-------------------------------------------
AL2.sht    335 NIYY-------------------------------------------
AL2.long   335 NIYYTSISVLEWPILHTIQLFFMRSKCSRVTTFLFPVQVITTSCRMTSF
```

FIG. 4B

```
LERK2        1  MA-RPGQRMLSKWMLVAMVVLTLCRLATPLAKNLEPVSWSSLNPKFLSGKG
huHTKL       1  MAVRRDSVMKYCMGVLMV---LCRTAISKSIVLEPIYWNSNSKFLPGQG
AL2.long     1  MGPPHSGP-GGVRVGALLL---LGVLGLVSGLSLEPVYWNSANKRFQAEGG LERK2       50  LVIYPKIGDKLDIICPRA---EAGR--PYEYYKLYLVRPEQAAACSTVLD
huHTKL      48  LVLYPQIGDKLDIICPKV---DSKTVGQYEYYKVYMVDKDQADRCTIKKE
AL2.long    48  YVLYPQIGDRLDLLCPRARPPGPHSSPNYEFYKLYLVGGAQGRRCEAPPA LERK2       95  PNVLVTCNKPHQEIRFTIKFQEFSPNYMGLEFKKYHDYYITSTSNGSLEG
huHTKL      95  NTPLLNCAKPDQDIKFTIKFQEFSPNLWGLEFQKNKDYYIISTSNGSLEG
AL2.long    98  PNLLLTCDRPDLDLRFTIKFQEYSPNLWGHEFRSHHDYYIATSDGTREG LERK2      145  LENREGGVCRTRTMKIVMKVGQDPNAVTPEQLTTSRPSKESDNTVKTATQ
huHTKL     145  LDNQEGGVCQTRAMKILMKVGQDASS-----AGSTRNKDPTRRPELEAG
AL2.long   148  LESLQGGVCLTRGMKVLLRVGQSPRG------GAVPRKPVSEMPMERDRG huHTKL     195  APGRGSQGDSDGKHETVNQEEKSGPGAGGGGSGGDSDSFFNSKVALFAAVG
AL2.sht    189  TNGRSSTTSPFVKPNPGSSTDGNSAGHSG---NNILGSEVALFAGIA
AL2.long   192  AHSLEPGKENLPGDPTSNATSRGAE------GPLPPSMPAVAGAA
```

FIG. 5A

```
LERK2    245 AGCVIFLLIIF LTVLLLKLRKRHRKHTQQ- - -STLASPKGGS
huHTKL   233 SGCIIFIVIITLVVLLLKYRRRHRKHSPQH- - -STLATPKRSG
AL2.long 233 GGLALLLLGVAGAGGAMCWRRRAKPSESRHPGPGSFGRGGSLGLGGGGGG LERK2    292 -GTAGTEPSDIIIPLR- - -TTENNYCPHYEKVSGDYGHPVYIVQEMPPQS
huHTKL   280 -NNNGSEPSDIIIPLR- - -TADSVFCPHYEKVSGDYGHPVYIVQEMPPQS
AL2.long 283 MGPREAEPGELGIALRGGGAADPPFCPHYEKVSGDYGHPVYIVQDGPPQS LERK2    338 PANIYY- - - - - - - - - - - - - - - - - - - - - - - - - - - - - - - - -
huHTKL   326 PANIYY- - - - - - - - - - - - - - - - - - - - - - - - - - - - - - - - -
AL2.long 333 PPNIYYTSISVLEWPILHTIQLFFMRSKCSRVTTFLFPVQVITTSTCRMT LERK2    344 - - - - - - - - - - - - - - - - - - - - - - - - - - - - - - - - - KV- - - - - - - - - - - -     (SEQ ID NO: 9)
huHTKL   332 - - - - - - - - - - - - - - - - - - - - - - - - - - - - - - - - - KV- - - - - - - - - - - -     (SEQ ID NO: 10)
AL2.long 383 SFSFTTLNPSMQACRAQMGEFRIRWCFWGDRILGTALFVLVLILLLGRLN AL2.long 433 MHQTTLLRQRASVEAEAGQHGPL (SEQ ID NO: 2)
```

FIG. 5B

| FIG. 5A |
|---------|
| FIG. 5B |

FIG. 5

AL-2 NEUROTROPHIC FACTOR NUCLEIC ACID

TECHNICAL FIELD

This application relates to a receptor protein tyrosine kinase ligand and its uses. In particular this application relates to the production and use of purified forms of AL-2 and related proteins.

BACKGROUND

Protein neurotrophic factors, or neurotrophins, which influence growth and development of the vertebrate nervous system, are believed to play an important role in promoting the differentiation, survival, and function of diverse groups of neurons in the brain and periphery. Neurotrophic factors are believed to have important signaling functions in neural tissues, based in part upon the precedent established with nerve growth factor (NGF). NGF supports the survival of sympathetic, sensory, and basal forebrain neurons both in vitro and in vivo. Administration of exogenous NGF rescues neurons from cell death during development. Conversely, removal or sequestration of endogenous NGF by administration of anti-NGF antibodies promotes such cell death (Heumann, *J. Exp. Biol.*, 132:133–150 (1987); Hefti, *J. Neurosci.*, 6:2155–2162(1986); Thoenen et al., *Annu. Rev. Physiol.*, 60:284–335 (1980)).

Additional neurotrophic factors related to NGF have since been identified. These include brain-derived neurotrophic factor (BDNF) (Leibrock, et al., *Nature*, 341:149–152 (1989)), neurotrophin-3 (NT-3) (Kaisho, et al., *FEBS Lett.*, 266:187 (1990); Maisonpierre, et al., *Science*, 247:1446 (1990); Rosenthal, et al., *Neuron*, 4:767 (1990)), and neurotrophin 4/5 (NT-4/5) (Berkmeier, et al., *Neuron*, 7:857–866 (1991)).

Neurotrophins, similar to other polypeptide growth factors, affect their target cells through interactions with cell surface receptors. According to our current understanding, two kinds of transmembrane glycoproteins act as receptors for the known neurotrophins. Equilibrium binding studies have shown that neurotrophin-responsive neuronal cells possess a common low molecular weight (65,000–80,000 Daltons), a low affinity receptor typically referred to as $p75^{LNGFR}$ or p75, and a high molecular weight (130,000–150,000 Dalton) receptor. The high and low affinity receptors are members of the trk family of receptor tyrosine kinases.

Receptor tyrosine kinases are known to serve as receptors for a variety of protein factors that promote cellular proliferation, differentiation, and survival. In addition to the trk receptors, examples of other receptor tyrosine kinases include the receptors for epidermal growth factor (EGF), fibroblast growth factor (FGF), and platelet-derived growth factor (PDGF). Typically, these receptors span the cell membrane, with one portion of the receptor being intracellular and in contact with the cytoplasm, and another portion of the receptor being extracellular. Binding of a ligand to the extracellular portion of the receptor induces tyrosine kinase activity in the intracellular portion of the receptor, with ensuing phosphorylation of various intracellular proteins involved in cellular signaling pathways.

Recently, a receptor tyrosine kinase subclass referred to as the Eph receptor subclass or family has been identified. Eph was the first member of this Eph subclass of receptor tyrosine kinases to be identified and characterized by molecular cloning (Hirai et al., *Science*, 238:1717–1720 (1987)). The name Eph is derived from the name of the cell line from which the Eph cDNA was first isolated, the erythropoietin-producing human hepatocellular carcinoma cell line, ETL-1. The general structure of Eph is similar to that of other receptor tyrosine kinases and consists of an extracellular domain, a single membrane spanning region, and a conserved tyrosine kinase catalytic domain. However, the structure of the extracellular domain of Eph, which comprises an immunoglobulin (Ig)-like domain at its amino terminus, followed by a cysteine-rich region and two fibronectin type III repeats in close proximity to the transmembrane domain, is completely distinct from that of previously described receptor tyrosine kinases. The juxtamembrane domain and carboxy-terminus regions of Eph also are unrelated to the corresponding regions of other tyrosine kinase receptors.

Newly discovered members of the Eph receptor family include Elk, Cek5, Mek4, Cek4, Hek/Hek4 (Sajjadi et al., *The New Biologist*, 3:769–778 (1991)), Cek6 through Cek10 (Sajjadi et al., *Oncogene*, 8:1807–13 (1993), Sek, Hek2, and Ehk3 (Tuzi, et al., *Br. J. Cancer*, 69:417–421 (1994); Zhou, et *J. Neurosci. Res.*, 37:129–143 (1994)). Other Eph-related receptor kinases that have been identified include Sek (Gilardi-Hebenstreit et al, *Oncogene*, 7:2499–2506 (1992)), Eck (Lindberg et al., *Mol. Cell. Biol.*, 10:6316–6324 (1990)), Elk (Lhotak et al., *Mol. Cell. Biol.*, 11:2496–2502 (1991)), Eek (Chan et al., *Oncogene*, 6:1057–1061 (1991)), Rek7 (Winslow et al., *Neuron*, 14:973–981 (1995). Rek7 is a rat homolog of chicken Cek7 and closely related to Ehk-1 (Davis et al., *Science*, 266:816–819 (1994)) and bsk (Maisonpierre et al., *Oncogene*, 8:3277–3288 (1993); Zhou et al., *J. Neurosci. Res*,. 37:129–143 (1994)); the Rek7 cDNA corresponds to a splice variant of Ehk-1, lacking the first of two tandem fibronectin type-III domains. Human homologs of the chicken Cek receptors are referred to as Hek receptors (See WO 95/28484, which is incorporated herein by reference). For example, Hek5 (Fox et al., *Oncogene*, 10(5):897–905 (1995); WO 95/28484) is the human homolog of chicken Cek5. The amino acid sequence of Hek5 is very closely related (96% amino acid identity in the catalytic domain) to the chicken receptor Cek5 (Pasquale et al., *J. Neuroscience*, 12:3956–3967 (1992); Pasquale, *Cell Regulation*, 2:523–534 (1991)). A portion of the Hek5 sequence was previously disclosed as Erk, a human clone encoding about sixty amino acids (Chan et al., *Oncogene*, 6:1057–1061 (1991)). Mature Erk showed high homology with Cek5 (92.5%) and mouse Nuk (99.1%) (Kiyokawa et al., *Cancer Res.*, 54 (14):3645–50 (1994)). Other human Eph-family receptors include Hek (Wicks et al., *Proc. Natl. Acad. Sci. USA*, 89(5):161 1–1615 (1992); also known as Hek4), Hek2 (Bohme et al., *Oncogene*, 8:2857–2862 (1993)), Heks 7, 8 and 11 (WO 95/28484), Hek3, which is a homolog of rat Eek and murine Mdk-1, and Hek 12, which is a homolog of rat Ehk2.

Many of the Eph-receptor family members are "orphan receptors." However, recently, ligands have been reported including B61, an Eck receptor ligand (Bartley et al., *Nature*, 368:558–560 (1994) and Pandey et al., *Science*, (1995) 268:567–569), Elf-1, a Mek4 and Sek receptor ligand (Cheng et al., Cell, (1995) 82:371–381; Cheng et al., *Cell*, 79:157–168 (1994)), Htk-L (Bennett et al., *Proc. Natl. Acad. Sci. USA*, 92(6):1866–70 (1995)), AL-1 (Winslow et al, *Neuron*, 14:973–981 (1995)) and RAGS (Drescher et al., *Cell*, (1995) 82:359–370), which are Rek7 ligands, Ehk-1-L (Davis et al., *Science*, 266:816–819 (1994); see also efl-2 in WO 95/27060), Cek5-L, and Lerk2 (Beckmann et al., *EMBO J.*, 13:3757–3762 (1994)).

Aberrant expression of receptor tyrosine kinases correlates with transforming ability. This relationship includes members of the Eph subclass of receptor tyrosine kinases. For example, carcinomas of the liver, lung, breast and colon show elevated expression of Eph. Unlike many other tyrosine kinases, this elevated expression can occur in the absence of gene amplification or rearrangement. Such involvement of Eph in carcinogenesis also has been shown by the formation of foci of NIH 3T3 cells in soft agar and of tumors in nude mice following overexpression of Eph. Moreover, Hek has been identified as a leukemia-specific marker present on the surface of a pre-B cell leukemia cell line. As with Eph, Hek also was overexpressed in the absence of gene amplification or rearrangements in, for example, hemopoietic tumors and lymphoid tumor cell lines. Over-expression of Myk-1 (a murine homolog of human Htk (Bennett et al., *J. Biol. Chem.*, 269(19): 14211–8 (1994)) was found in the undifferentiated and invasive mammary tumors of transgenic mice expressing the Ha-ras oncogene. (Andres et al., *Oncogene*, 9(5): 1461–7 (1994) and Andres et al., *Oncogene*, 9(8):2431 (1994)).

In addition to their roles in carcinogenesis, a number of transmembrane tyrosine kinases have been reported to play key roles during development. Some receptor tyrosine kinases are developmentally regulated and predominantly expressed in embryonic tissues. Examples include Cek1, which belongs to the FGF subclass, and the Cek4 and Cek5 tyrosine kinases (Pasquale et al., *Proc. Natl. Acad Sci., USA*, 86:5449–5453 (1989); Sajjadi et al., *New Biol.*, 3(8):769–78 (1991); and Pasquale, *Cell Regulation*, 2:523–534 (1991)).

Eph family members are expressed in many different adult tissues, with several family members expressed in the nervous system or specifically in neurons (Maisonpierre et al., *Oncogene*, 8:3277–3288 (1993); Lai et al., *Neuron*, 6:691–704(1991)).

The aberrant expression or uncontrolled regulation of any one of these receptor tyrosine kinases can result in different malignancies and pathological disorders. Therefore, there exists a need to identify means to regulate, control and manipulate receptor tyrosine kinases and their ligands in order to provide new and additional means for the diagnosis and therapy of Eph-pathway related disorders and cellular processes. The present application provides the clinician and researcher with such means by providing new molecules that are specific for interacting with Eph-family receptors. These compounds and their methods of use, as provided herein, allow exquisite therapeutic control and specificity. Additional advantages are provided as well.

SUMMARY

The present invention provides a novel cytokine, an Eph-related tyrosine kinase receptor ligand referred to as AL-2.

The present invention provides nucleic acid encoding AL-2, particularly two forms referred to herein as AL-2s ("AL-2-short") and AL-21 ("AL-2-long"), and methods to use the nucleic acid to produce AL-2 in recombinant host cells for diagnostic or therapeutic purposes. Also provided are uses of nucleic acids encoding AL-2, and portions thereof, to identify related nucleic acids in the cells or tissues of various animal species.

By providing the full nucleotide coding sequence for AL-2, the invention enables the production of AL-2 by means of recombinant DNA technology, thereby making available for the first time sufficient quantities of substantially pure AL-2 protein or AL-2 antagonists for diagnostic and therapeutic uses. For example, method embodiments include treatment or prevention of a variety of neurological disorders and diseases as well as conditions that are angiogenesis-dependent such as solid tumors, diabetic retinopathy, rheumatoid arthritis, and wound healing.

Also provided are derivatives and modified forms of AL-2, including amino acid sequence variants and covalent derivatives thereof, as well as antagonists of AL-2, that are preferably biologically active (e.g., antigenically active. In one embodiment, the invention provides a soluble form of the ligand with at least the transmembrane region deleted. Usually, the cytoplasmic domain will also be absent. Immunogens are provided for raising antibodies, as well as to obtain antibodies, capable of binding to, preferably neutralizing, AL-2 or derivatives or modified forms thereof.

In a preferred embodiment, the invention provides AL-2 that is free of other human proteins.

AL-2 and modified and variant forms of AL-2 are produced by means of chemical or enzymatic treatment or by means of recombinant DNA technology, including in vivo production. Variant polypeptides can differ from native AL-2, for example, by virtue of one or more amino acid substitutions, deletions or insertions, or in the extent or pattern of glycosylation, but will substantially retain a biological activity of native AL-2.

Chimeras comprising AL-2 (or a portion thereof) fused to another polypeptide are provided. An example of such a chimera is epitope-tagged AL-2. In another embodiment a soluble form of an AL-2 chimera is provided, for example, as an immunoadhesin, which is a fusion of the extracellular domain of AL-2 and an immunoglobulin sequence.

Antibodies to AL-2 are produced by immunizing an animal with AL-2 or a fragment thereof, optionally in conjunction with an immunogenic polypeptide, and thereafter recovering antibodies from the serum of the immunized animals. Alternatively, monoclonal antibodies are prepared from cells of the immunized animal in conventional fashion. Antibodies obtained by routine screening will bind to AL-2 but, preferably, will not substantially bind to (i.e., cross react with) NGF, BDNF, NT-3, NT-4/5, GDNF, AL-1, Htk-L, Lerk-2, or other neurotrophic factors or cytokines; Immobilized anti-AL-2 antibodies are particularly useful in the detection of AL-2 in clinical samples for diagnostic purposes, and in the purification of AL-2.

AL-2, its derivatives, or its antibodies are formulated with physiologically acceptable carriers, especially for therapeutic use. Such carriers are used, for example, to provide sustained-release formulations of AL-2.

In further aspects, the invention provides a method for determining the presence of a nucleic acid molecule encoding AL-2 in test samples prepared from cells, tissues, or biological fluids, comprising contacting the test sample with isolated DNA comprising all or a portion of the nucleotide coding sequence for AL-2 and determining whether the isolated DNA hybridizes to a nucleic acid molecule in the test sample. DNA comprising all or a portion of the nucleotide coding sequence for AL-2 is also used in hybridization assays to identify and to isolate nucleic acids sharing substantial sequence identity to the coding sequence for AL-2, such as nucleic acids that encode allelic variants of AL-2.

Also provided is a method which involves contacting an AL-2 receptor with AL-2 in order to cause phosphorylation of the kinase domain of the receptor.

Also provided is a method for amplifying a nucleic acid molecule encoding AL-2 that is present in a test sample, comprising the use of an oligonucleotide having a portion of the nucleotide coding sequence for AL-2 as a primer in a polymerase chain reaction.

BRIEF DESCRIPTION OF THE DRAWINGS

FIGS. 1A–1C shows the AL-21-encoding nucleotide sequence (SEQ ID NO:1) its complementary sequence, and the deduced amino acid sequence (SEQ ID NO:2) of AL-2 of the isolated AL-21 ("AL-2-long") cDNA. The deduced N-terminus of the mature AL-2 protein begins with glycine-27 as numbered from the initiation methionine. The C-terminal hydrophobic transmembrane domain extends from amino acid Leu-220 to Ala-245. The deduced extracellular domain sequence includes amino acids Gly-27 to Pro-219.

FIGS. 2A–2D shows the AL-2s-encoding nucleotide sequence (SEQ ID NO: 3) its complementary sequence, and the deduced amino acid sequence (SEQ ID NO:4) of AL-2 of the isolated AL-2s ("AL-2-short") cDNA. The deduced N-terminus of the mature AL-2 protein begins with glycine-27 as numbered from the initiation methionine. The C-terminal hydrophobic transmembrane domain extends from amino acid Leu-220 to Ala-245. The deduced extracellular domain sequence includes amino acids Gly-27 to Pro-219.

FIGS. 3A–3C depicts an alignment of the AL-21 nucleotide sequence with human EST sequence H10006 (SEQ ID NO:5).

FIG. 5 shows a comparison of the AL-21 amino acid sequences with that of Lerk2 (SEQ ID NO: 9) and human Htk-L. Identical amino acids are boxed, and gaps introduced for optimal alignment are indicated by dashes. Conserved cysteine residues can be seen.

DETAILED DESCRIPTION

Figure 1B:
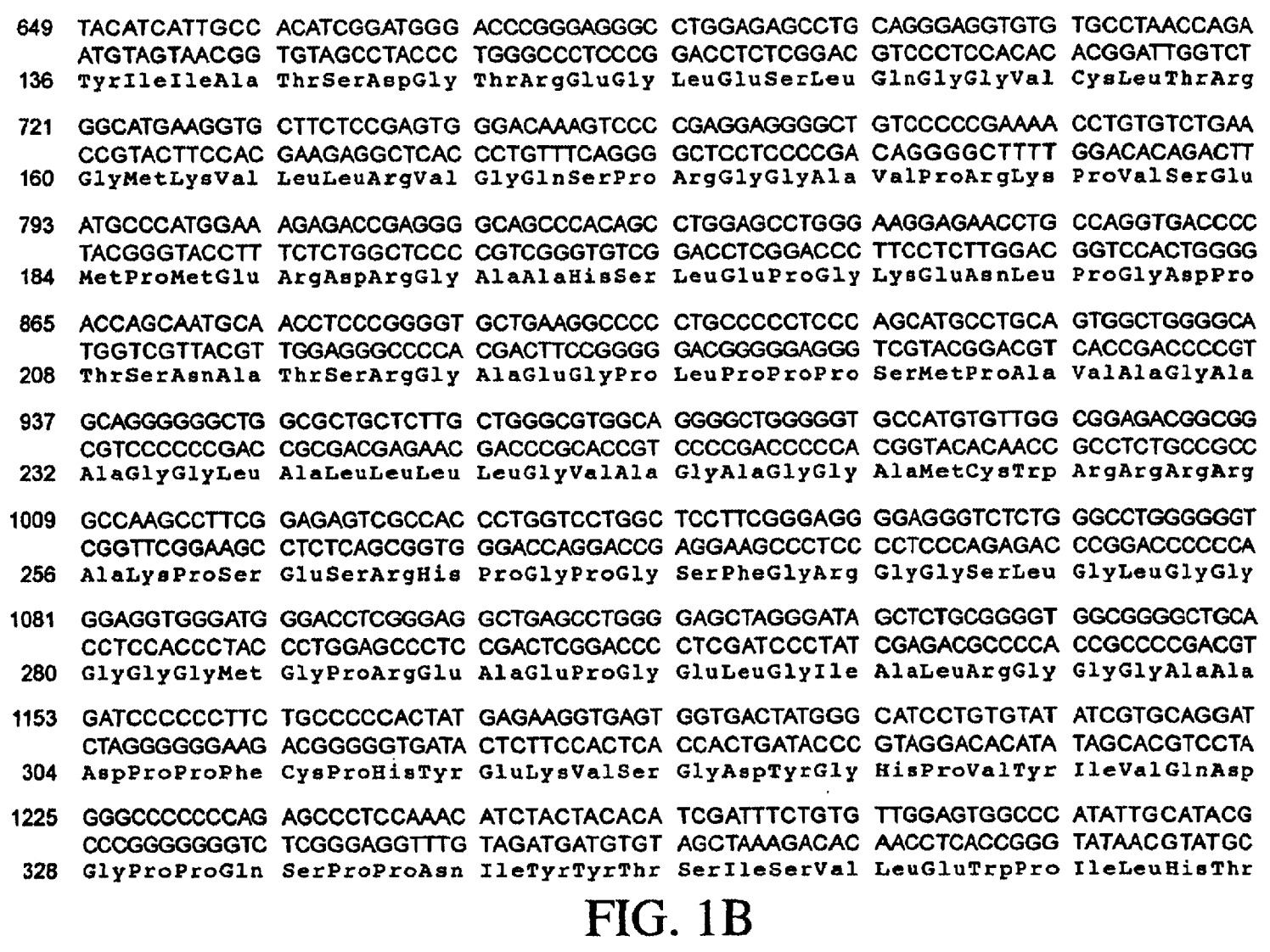
Figures 4, 4C:
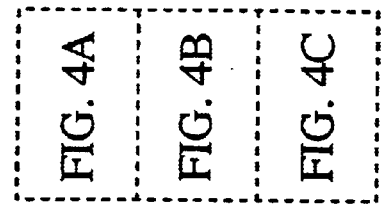
FIG. 4 shows a comparison of the AL-21 and AL-2s amino acid sequences with that of Lerk2 (SEQ ID NO:9) (Beckmann et al., *EMBO J.*, 13:3757–3762 (1994)) and human Htk-L (SEQ ID NO: 10) (Bennett et al., *Proc. Natl. Acad. Sci. USA*, 92:1866–70 (1995); WO 96/02645 published Feb. 1, 1996; both are incorporated by reference herein). Identical amino acids are boxed, and gaps introduced for optimal alignment are indicated by dashes. Conserved cysteine residues can be seen. The deduced C-terminal amino acid for AL-2s is valine.

"AL-2" or "AL-2 protein" refers to a polypeptide or protein encoded by the AL-2 nucleotide sequence set forth in FIGS. 1A–1B (showing AL-21) or 2 (showing AL-2s); a polypeptide that is the translated amino acid sequence set forth in FIGS. 1A–1B or 2A–2B; fragments thereof having greater than about 5 contiguous amino acid residues and comprising an immune epitope or other biologically active site of AL-2; amino acid sequence variants of the amino acid sequence set forth in FIGS. 1A–1B or 2A–2B wherein one or more amino acid residues are added at the N- or C-terminus of, or within, said FIGS. 1A–1B or 2A–2B sequences or its fragments as defined above; amino acid sequence variants of said FIGS. 1A–1B or 2A–2B sequences or its fragments as defined above wherein one or more amino acid residues of said FIGS. 1A–1B or 2A–2B sequences or fragment thereof are deleted, and optionally substituted by one or more amino acid residues; and derivatives of the above proteins, polypeptides, or fragments thereof, wherein an amino acid residue has been covalently modified so that the resulting product is a non-naturally occurring amino acid. Preferred embodiments retain a biological property of AL-2. AL-2 amino acid sequence variants may be made synthetically, for example, by site-directed or PCR mutagenesis, or may exist naturally, as in the case of allelic forms and other naturally occurring variants of the translated amino acid sequence set forth in FIGS. 1A–1B or 2A–2B that occur in human or other animal species. Accordingly, within the scope of the present invention are AL-2 proteins derived from other animal species, preferably mammalian, including but not limited to murine, rat, bovine, porcine, or various primates. As used herein, the term "AL-2" includes membrane-bound proteins (comprising a cytoplasmic domain, a transmembrane region, and an extracellular domain), including the long and short forms of AL-2, as well as truncated proteins that retain Eph-family-receptor binding property. Truncated AL-2 proteins include, for example, soluble AL-2 comprising only the extracellular (receptor binding) domain. Such fragments, variants, and derivatives exclude any polypeptide heretofore identified, including any known neurotrophic factor, such as nerve growth factor (NGF), brain derived neurotrophic factor (BDNF), neurotrophin-3 (NT-3), and neurotrophin-4/5 (NT-4/5), Eph family receptor ligand such as Erk-L or Lerk-2, as well as statutorily obvious variants thereof. A preferred AL-2 is one having a contiguous amino acid sequence of or derived from mature AL-2 shown in FIGS. 1A–1B or 2A–2B.

By "Eph-related protein tyrosine kinase" or "Eph-related kinase" or "Eph-family receptor" means herein a receptor tyrosine kinase having an extracellular ligand binding domain, a transmembrane domain, and a cytoplasmic catalytic domain, and belonging to the Eph subclass of receptor tyrosine kinases. Eph-family receptors include, for example, human receptor tyrosine kinases, Eph, Erk/Nuk, Htk, Eck, and Heks (e.g., Hek, Hek2, Hek3, Hek4, Hek5, Hek6, Hek7, Hek8, Hek9, Hek11, Hek12), an counterparts including chicken Ceks (e.g., Cek5, Cek6, Cek7, Cek8, Cek9, Cek10), murine Nuk, Seks (e.g., Sek1, Sek2, Sek3, Sek4; Gilardi-Hebenstreit et al, *Oncogene* 7:2499–2506 (1992)), Myk-1 (Andres et al., *Oncogene* 9(5):1461–7 (1994)), Mek4, Mdk-1, and rat Tyros (e.g., Tyro1, Tyro4, Tyro5, Tyro6, Tyro11), Rek7, Ehk1, Ehk2, Ehk3, Bsk, Eek, and Elk. Natural ligands for these receptors can be characterized by means of ligand attachment to a cell membrane—either by a GPI-anchor (e.g., Lerk3 and Lerk4 (Koziosky et al., *Oncogene*, 10(2): 299–306 (1995)) or by a transmembrane sequence. Preferred receptors for AL-2 are receptors that are recognized by transmembrane-sequence type ligands. Preferred receptors include rat Elk, Tyro5 (Marcelle et al., *Oncogene*, 7:2479–87 (1992)), and Tyro6, murine Nuk/Sek3 (Henkemeyer et al., *Oncogene*, 9(4):1001–14 (1994); Becker et al., *Mech. Dev.*, 47(1):3–17 (1994)), Myk-1, and Sek4 (Beker et al., *Mechanisms of Development*, 47:3–17 (1994)), chicken Cek5, Cek6 and Cek10, and their human homologs. More preferred are human receptors Hek5, Hek6, Hek3, Hek2, Keh9, Hek11, Hek12, Htk, Erk and Eph. Even more preferred are human receptors Htk (WO 96/02645 published Feb. 1, 1996), Hek2 (Bohme et al., *Oncogene*, 8:2857–2862 (1993)), Hek5/Erk (Fox et al., *Oncogene*, 10(5):897–905 (1995); (Kiyokawa et al., *Cancer Res.*, 54 (14):3645–50 (1994), and Hek6. Of particularly preferred interest as an AL-2 binding receptor candidate are "orphan receptors," including human Eph, Hek3, Hek9, Hek11 and Hek12, and less preferably their non-human homologs, as well as Ehk3 for which a human homolog is not known.

Eph-family-receptor-binding-transmembrane-sequence-containing ligands include the human Erk-L or Lerk2 ligand (Fletcher et al., *Oncogene*, 9(11):3241–7 (1994)) and the human Htk-L or Lerk5 ligand (Cerretti et al., *Mol. Immunol.*, 32(16):1197–205 (1995)). Non-human ligands include Cek5-L, Elf-2 and Elk-L.

Biologically active or antigenically active AL-2 polypeptides embodiments of this invention include the polypeptide represented by the entire translated nucleotide sequence of AL-2l and AL-2s (including their signal sequence); mature AL-2, i.e., AL-2 without the signal sequence; fragments consisting essentially of the intracellular domain or transmembrane domain of AL-2; fragments of the AL-2 having a contiguous sequence of at least 5, 10, 15, 20, 25, 30, or 40 consecutive amino acid residues from AL-2; amino acid sequence variants of AL-2 wherein an amino acid residue has been inserted N- or C-terminal to, or within, AL-2 or its fragment as defined above; amino acid sequence variants of AL-2 or its fragment as defined above wherein an amino acid residue of AL-2 or its fragment as defined above has been substituted by another residue, including predetermined mutations by, e.g., site-directed or PCR mutagenesis, AL-2 of various animal species such as rabbit, rat, porcine, non-human primate, equine, murine, and ovine AL-2 and alleles or other naturally occurring variants of the foregoing and human AL-2; derivatives of AL-2 or its fragments as defined above wherein AL-2 or its fragments have been covalent modified, by substitution, chemical, enzymatic, or other appropriate means, with a moiety other than a naturally occurring amino acid; and glycosylation variants of AL-2 (insertion of a glycosylation site or alteration of any glycosylation site by deletion, insertion, or substitution of suitable residues). The preferred AL-2 is human AL-2, especially native human AL-2 having the sequence shown in FIGS. 1A–1B or 2A–2B.

One embodiment of the present invention provides soluble AL-2. By "soluble AL-2" is meant AL-2 which is essentially free of at least a transmembrane sequence and, optionally, the intracellular domain of native AL-2. By "essentially free" is meant that the soluble AL-2 sequence has less than 2% of the transmembrane domain, preferably less than 1% of the transmembrane domain, and more preferably less than 0.5% of this domain. The transmembrane domain of the native human mature amino acid sequences are delineated in FIGS. 1A–1B and 2A–2B,(for AL-2l and AL-2s, respectively), i.e., resides Gly-27 to Pro-219. Soluble AL-2s have therapeutic advantages because they are generally soluble in the patient's blood stream. Similarly, soluble ligands may prove to be particularly useful as diagnostics since they are expected to have a reduced tendency to incorporate in the cell membrane. Soluble AL-2 polypeptides comprise all or part of the extracellular domain of a native AL-2 but lack the transmembrane region that would cause retention of the polypeptide on a cell membrane. Soluble,AL-2 polypeptides advantageously comprise the native (or a heterologous) signal peptide when initially synthesized to promote secretion, but the signal peptide is cleaved upon secretion. In preferred embodiments, the soluble AL-2 polypeptides retain the ability to bind an Eph-family receptor with preferences as discussed herein. Soluble AL-2 can also include part of the transmembrane region or part of the cytoplasmic domain or other sequences, provided that the soluble AL-2 protein is capable of being secreted or otherwise isolated.

In one embodiment a soluble AL-2 is an "immunoadhesin". The term "immunoadhesin" is used interchangeably with the expression "AL-2-immunoglobulin chimera" and refers to a chimeric molecule that combines the extracellular domain ("ECD") of AL-2 with an immunoglobulin sequence. The immunoglobulin sequence preferably, but not necessarily, is an immunoglobulin constant domain. The immunoglobulin moiety in the chimeras of the present invention may be obtained from IgG-1, IgG-2, IgG-3 or IgG-4 subtypes, IgA, IgE, IgD or IgM, but preferably IgG-1 or IgG-3. The expression "extracellular domain" or "ECD" when used herein refers to any polypeptide sequence that shares a receptor binding function of the extracellular domain of the naturally occurring AL-2 disclosed herein. Receptor binding function refers to the ability of the polypeptide to bind the extracellular domain of a Eph-family receptor, with preferences as discussed herein, and, optionally, activate the receptor. Accordingly, it is not necessary to include the entire extracellular domain since smaller segments are commonly found to be adequate for receptor binding. The term ECD encompasses polypeptide sequences in which the cytoplasmic domain and hydrophobic transmembrane sequence (and, optionally, 1–20 amino acids amino-terminal to the transmembrane domain) of the mature AL-2 have been deleted. The extracellular domain sequence of AL-2 is provided in FIGS. 1A–1B and 2A–2B.

The term "epitope tagged" when used herein refers to a chimeric polypeptide comprising the entire AL-2, or a portion thereof, fused to a "tag polypeptide." The tag polypeptide has sufficient amino acids to provide an antibody-binding epitope but not interfere with activity of the AL-2. The tag polypeptide preferably also is fairly unique so that an antibody against it does not substantially cross-react with other epitopes. Suitable tag polypeptides generally have at least 6 amino acid residues and usually between about 8–50 amino acid residues, preferably between about 9–30 residues.

"Isolated", when used to describe the various proteins disclosed herein, means protein that has been identified and separated and/or recovered from a component of its natural environment. Contaminant components of its natural environment are materials that would interfere with diagnostic or therapeutic uses for the protein, and may include enzymes, hormones, and other proteinaceous or non-proteinaceous solutes.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

An AL-2 amino acid sequence variant is included within the scope of the invention provided that it is functionally active. As used herein, "functionally active" and "functional activity" in reference to AL-2 for the purposes herein means an in vivo effector or antigenic function or activity that is performed by AL-2 of the sequences in FIGS. 1A–1B or 2A–2B (whether in its native or denatured conformation). A principal effector function is the ability of AL-2 to bind to, and/or activate, a receptor from the Eph-receptor family, preferably a receptor for the transmembrane-ligand family that is also, more preferably, a human receptor. Less preferred are their non-human homologs.

Generally, the ligand will bind to the extracellular domain of the receptor and thereby activate its intracellular tyrosine kinase domain. Consequently, binding of the ligand to the receptor can result in enhancement or inhibition of proliferation and/or differentiation and/or activation of cells having a receptor for AL-2 in vivo, ex vivo, or in vitro. Other effector functions include signal transduction, any enzyme activity or enzyme modulatory activity (e.g., tyrosine kinase activity), or any structural role, for example. An antigenic function means possession of an epitope or antigenic site that is capable of cross-reacting with antibodies raised against the polypeptide sequence of a naturally occurring polypeptide comprising the polypeptide sequences of FIGS. 1A–1B and 2A–2B.

In preferred embodiments, antigenically active AL-2 is a polypeptide that binds with an affinity of at least about $10^6$ 1/mole to an antibody capable of binding AL-2. Ordinarily, the polypeptide binds with an affinity of at least about $10^7$ 1/mole. In particular, an AL-2 is able to promote or enhance the growth, survival, function, activation, and/or differentiation of neurons and glia, whether the neurons be central, peripheral, motoneurons, or sensory neurons, e.g., photoreceptors, vestibular ganglia, spinal ganglia, auditory hair cells, and the AL-2 is immunologically cross-reactive with an antibody directed against an epitope of naturally occurring AL-2. Therefore, AL-2 amino acid sequence variants generally will share at least about 75% (preferably at least 80%, more preferably at least 90%, even more preferably at least 95%, with increasing preference to at least 99%, and finally, 100%) sequence identity with the translated amino acid sequence set forth in FIGS. 1A–1B and 2A–2B, after aligning the sequences and introducing gaps, if necessary, to achieve maximal percent identity. This is typically determined, for example, by the Fitch, et al., *Proc. Nat. Acad. Sci. USA*, 80:1382–1386 (1983), version of the algorithm described by Needleman, et al., *J. Mol. Biol.*, 48:443–453 (1970). None of N-terminal, C-terminal, or internal extensions, deletions, or insertions into the AL-2 sequence shall be construed as affecting sequence identity or homology. Preferably, the AL-2 nucleic acid molecule that hybridizes to nucleic acid sequence encoding AL-2 contains at least 20, more preferably 40, even more preferably 70, and most preferably 90 bases. For fragments, the percent identity is calculated for that portion of-a native sequence that is present in the fragment.

In one embodiment an isolated AL-2 protein induces phosphorylation of an Eph-family receptor and contains an amino acid sequence selected from the group consisting of (a) the amino acid sequence for mature AL-2l, (b) the amino acid sequence for mature AL-2s, (c) the naturally occurring amino acid sequence for mature AL-2 from a non-human animal species, (d) allelic variants of the sequences of (a), (b), or (c), and (e) the sequences of (a), (b), (c), or (d) having a single preferred conservative amino acid substitution as defined in Table 1. In a preferred embodiment the phosphorylation-inducing AL-2 has the amino acid sequence for mature human AL-2 shown in FIGS. 1A–1B or 2A–2B. Generally the AL-2 will be a chimera, membrane or liposome bound, or epitope tagged and "clustered" (see WO 95/27060, which is incorporated herein by reference), thus mimicking its membrane-bound state and ability to induce receptor phosphorylation. In another embodiment an isolated AL-2 protein binds to the Eph-family receptor and contains an amino acid sequence selected from the group consisting of (a) the amino acid sequence for mature AL-2l, (b) the amino acid sequence for mature AL-2s, (c) the naturally occurring amino acid sequence for mature AL-2 from a non-human animal species, (d) allelic variants of the sequences of (a), (b), or (c), and (e) the sequences of (a), (b), (c), or (d) having a single preferred conservative amino acid substitution as defined in Table 1. In a preferred embodiment the AL-2 has the amino acid sequence for mature human AL-2 shown in FIGS. 1A–1B or 2A–2B. In another embodiment isolated soluble AL-2 binds to a Eph-family receptor and contains an amino acid sequence selected from the group consisting of (a) the amino acid sequence for mature soluble AL-2l, (b) the amino acid sequence for mature soluble AL-2s, (c) the naturally occurring amino acid sequence for mature soluble AL-2 from a non-human animal species, (d) allelic variants of the sequences of (a), (b), or (c), and (e) the sequences of (a), (b), (c), or (d) having a single preferred conservative amino acid substitution as defined in Table 1. In a preferred embodiment the soluble AL-2 has the amino acid sequence for mature soluble human AL-2 shown in FIGS. 1A–1B or 2A–2B. In another preferred embodiment, the soluble AL-2 is a chimeric polypeptide containing an amino acid sequence encoding mature soluble AL-2 fused to an immunoglobulin sequence. In a more preferred embodiment the chimeric polypeptide contains a fusion of an AL-2 extracellular domain sequence to an immunoglobulin constant domain sequence. Preferably the constant domain sequence is that of an immunoglobulin heavy chain. Also preferred are chimeric polypeptides containing a mature, soluble Al-2 amino acid sequence fused to an epitope tag polypeptide sequence.

AL-2 can be recovered from culture of cells expressing AL-2, preferably from the culture medium as a secreted polypeptide; although, AL-2 can be recovered from host cell lysates when directly produced without a secretory signal. When AL-2 is membrane-bound, it can be released from the membrane using a suitable detergent solution (e.g., Triton-X100™). When AL-2 is produced in a recombinant cell other than one of human origin, AL-2 is completely free of proteins or polypeptides of human origin. However, it is necessary to purify AL-2 from recombinant cell proteins or polypeptides to obtain preparations that are substantially homogeneous in AL-2. As a first step, the culture medium or lysate is centrifuged to remove particulate cell debris. Then AL-2 is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex™ G-75; and protein A Sepharose™ columns to remove contaminants such as IgG.

In a preferred embodiment, an AL-2-receptor-Fc fusion, using the preferred AL-2-receptors in Fc constructs, for example as disclosed by Bennett et al., *J. Biol. Chem.*, 269(19):14211–8 (1994), is immobilized on a protein A Sepharose™ column and AL-2 can be isolated by affinity purification using this column.

AL-2 variants in which residues have been deleted, inserted, or substituted are recovered in the same fashion as native AL-2, taking account of any substantial changes in properties resulting from the variation. For example, preparation of an AL-2 fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-AL-2 column can be employed to absorb the AL-2 variant by binding it to at least one remaining immune AL-2 epitope. A protease inhibitor such as phenyl methyl sulfonyl fluoride (PMSF) also may be useful to inhibit proteolytic degradation during purification, and antibiotic s may be included to prevent the growth of adventitious contaminants. One skilled in the art will appreciate that purification methods suitable for native AL-2 can require modification to account for changes in the character of AL-2 or its variants upon expression in recombinant cell culture.

Amino acid sequence variants of AL-2 are prepared by introducing appropriate nucleotide changes into AL-2 DNA and thereafter expressing the resulting modified DNA in a host cell, or by in vitro synthesis. Such variants include, for example, deletions from, or insertions or substitutions of, amino acid residues within the AL-2 amino acid sequence set forth in FIGS. 1A–1B and 2A–2B. Any combination of deletion, insertion, and substitution may be made to arrive at an amino acid sequence variant of AL-2, provided that such variant possesses the desired characteristics described herein. Changes that are made in the amino acid sequence set forth in FIGS. 1A–1B and 2A–2B to arrive at an amino acid sequence variant of AL-2 also may result in further modifications of AL-2 upon its expression in host cells, for example, by virtue of such changes introducing or moving sites of glycosylation, or introducing membrane anchor sequences as described, for example, in PCT Pat. Pub. No. WO 89/01041 (published Feb. 9, 1989).

There are two principal variables in the construction of amino acid sequence variants of AL-2: the location of the mutation site and the nature of the mutation. These are variants from the amino acid sequence set forth in FIGS. 1A–1B and 2A–2B, and may represent naturally occurring allelic forms of AL-2, or predetermined mutant forms of AL-2 made by mutating AL-2 DNA, either to arrive at an allele or a variant not found in nature. In general, the location and nature of the mutation chosen will depend upon the AL-2 characteristic to be modified.

For example, due to the degeneracy of nucleotide coding sequences, mutations can be made in the AL-2 nucleotide sequence set forth in FIGS. 1A–1B and 2A–2B without affecting the amino acid sequence of the AL-2 encoded thereby. Other mutations can be made that will result in a AL-2 that has an amino acid sequence different from that set forth in FIGS. 1A–1B and 2A–2B, but which is functionally active. Such functionally active amino acid sequence variants of AL-2 are selected, for example, by substituting one or more amino acid residues in the amino acid sequence set forth in FIGS. 1A–1B and 2A–2B with other amino acid residues of a similar or different polarity or charge.

One useful approach is called "alanine scanning mutagenesis." Here, a an amino acid residue or group of target residues are identified (e.g., charged residues such as arginine, aspartic acid, histidine, lysine, and glutamic acid) and, by means of recombinant DNA technology, replaced by a neutral or negatively charged amino acid (most preferably alanine or polyalanine) to affect the interaction of the amino acids with the surrounding aqueous environment in or outside the cell, (Cunningham, et al., Science, 244:1081–1085 (1989)). Those domains demonstrating functional sensitivity to the substitutions then are refined by introducing further or other variants at or for the sites of substitution. Obviously, such variations that, for example, convert the amino acid sequence set forth in FIGS. 1A–1B and 2A–2B to the amino acid sequence of a known neurotrophic factor, such as NGF, BDNF, NT-3, NT-4/5, Eph-family receptor ligand (e.g., see FIGS. 4 and 5), or another known polypeptide or protein are not included within the scope of this invention, nor are any other fragments, variants, and derivatives of the amino acid AL-2 that are not novel and unobvious over the prior art. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed AL-2 variants are screened for functional activity.

Amino acid sequence deletions generally range from about 1 to 30 residues, more preferably about 1 to 10 residues, and typically are contiguous. Deletions from regions of substantial homology with other tyrosine kinase receptor ligands, for example, are more likely to affect the functional activity of AL-2. Generally, the number of consecutive deletions will be selected so as to preserve the tertiary structure of AL-2 in the affected domain, e.g., beta-pleated sheet or alpha helix.

Amino acid sequence insertions include amino- and/or carboxyl-terminal fusions ranging in length from one amino acid residue to polypeptides containing a hundred or more residues, as well as intrasequence insertions of single or multiple amino acid residues. Intrasequence insertions, i.e., insertions made within the amino acid sequence set forth in FIGS. 1A–1B or 2A–2B, may range generally from about 1 to 10 residues, more preferably 1 to 5, even more preferably 1 to 3, and most preferably 1 to 2. Examples of terminal insertions include AL-2 with an N-terminal methionyl residue (such as may result from the direct expression of AL-2 in recombinant cell culture), and AL-2 with a heterologous N-terminal signal sequence to improve the secretion of AL-2 from recombinant host cells. Such signal sequences generally will be homologous to the host cell used for expression of AL-2, and include STII or lpp for E. coli, alpha factor for yeast, and viral signals such as herpes gD for mammalian cells. Other insertions include the fusion to the N- or C-terminus of AL-2 of immunogenic polypeptides (for example, bacterial polypeptides such as beta-lactamase or an enzyme encoded by the E. coli trp locus, or yeast protein), and C-terminal fusions with proteins having a long half-life such as immunoglobulin constant regions, albumin, or ferritin, as described in PCT Pat. Pub. No. WO 89/02922 published Apr. 6, 1989.

The third group of variants are those in which at least one amino acid residue in the amino acid sequence set forth in FIGS. 1A–1B or 2A–2B, preferably one to four, more preferably one to three, even more preferably one to two, and most preferably only one, has been removed and a different residue inserted in its place. The sites of greatest interest for making such substitutions are in the regions of the amino acid sequence set forth in FIGS. 1A–1B or 2A–2B that have the greatest homology with other tyrosine kinase receptor ligands (for non-limiting examples, see comparisons in FIGS. 4 and 5). Those sites are likely to be important to the functional activity of the AL-2. Accordingly, to retain functional activity, those sites, especially those falling within a sequence of at least three other identically conserved sites, are substituted in a relatively conservative manner. Such conservative substitutions are shown in Table 1 under the heading of preferred substitutions. If such substitutions do not result in a change in functional activity, then more substantial changes, denominated exemplary substitutions in Table 1, or as further described below in reference to amino acid classes, may be introduced and the resulting variant AL-2 analyzed for functional activity.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |

TABLE 1-continued

| Original Residue | Exemplary Substitutions | Preferred Substitutions |
|---|---|---|
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Insertional, deletional, and substitutional changes in the amino acid sequence set forth in FIGS. 1A–1B and 2A–2B may be made to improve the stability of AL-2. For example, trypsin or other protease cleavage sites are identified by inspection of the encoded amino acid sequence for an arginyl or lysinyl residue. These are rendered inactive to protease by substituting the residue with another residue, preferably a basic residue such as glutamine or a hydrophobic residue such as serine; by deleting the residue; or by inserting a prolyl residue immediately after the residue. Also, any cysteine residues not involved in maintaining the proper conformation of AL-2 for functional activity may be substituted, generally with serine, to improve the oxidative stability of the molecule and prevent aberrant crosslinking.

Additional sites for mutation are those sites that are conserved in AL-2 amongst species variants of AL-2 but are not conserved between AL-2 and another ligand in the Eph ligand family, preferably between AL-2 and at least two ligands, and more preferably at least three ligands. Such sites, which are not conserved between AL-2 and another transmembrane-ligand, are candidates sites for modulating receptor specificity and selectivity. Sites that are conserved between AL-2 and other transmembrane-ligands are candidate sites for modulating activities shared by transmembrane-ligands, such as stability, folding, tertiary conformation, protease susceptibility, and amount of ligand specific activity.

A comparison of AL-2 amino acid sequences with other Eph-family receptor ligand sequences (see FIGS. 4 and 5) reveals AL-2 as a new Eph-family receptor ligand. AL-2, having a transmembrane sequence, is more closely related to other transmembrane-containing ligands than to the GPI-anchored ligands, of which AL-1 is an example. Transmembrane-containing ligands include Lerk-2, a ligand for the Eph-related receptor Hek5, and Htk-L, a ligand for the Htk receptor. Percent identities of ligand comparisons are provided in Table 2, in which "ECD" indicates extracellular domain.

TABLE 2

| Ligand | % IDENTITY | | |
|---|---|---|---|
| | Full Length | ECD | Cytoplasmic Domain |
| Lerk2 vs. HtkL | 56.0% | 49.3% | 74.7% |
| AL-2 vs Lerk2 | 41.5% | 42.1% | 48.2% |
| AL-2 vs HtkL | 40.8% | 39.5% | 56.6% |
| AL-2 vs AL-1 | 28.0% | | |

Covalent modifications of AL-2 molecules also are included within the scope of this invention. For example, covalent modifications are introduced into AL-2 by reacting targeted amino acid residues of the AL-2 with an organic derivatizing agent that is capable of reacting with selected amino acid side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking AL-2 to a water-insoluble support matrix or surface for use in the method for purifying anti-AL-2 antibodies, or for therapeutic use. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio]pro-pioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group, (Creighton, *Proteins: Structure and Molecular Properties*, pp.79–86 (W. H. Freeman & Co., 1983)). AL-2 also is covalently linked to nonproteinaceous polymers, e.g., polyethylene glycol, polypropylene glycol or polyoxyalkylenes, in the manner set forth in U.S. Pat. Nos. 4,179,337; 4,301,144; 4,496,689; 4,640,835; 4,670,417; or 4,791,192.

"AL-2 antagonist" or "antagonist" refers to a substance that opposes or interferes with a functional activity of AL-2.

"Cell," "host cell," "cell line," and "cell culture" are used interchangeably and all such terms should be understood to include progeny. Thus, the words "transformants" and "transformed cells" include the primary subject cell and cultures derived therefrom without regard for the number of times the cultures have been passaged. It should also be understood that all progeny may not be precisely identical in DNA content, due to deliberate or inadvertent mutations.

"Plasmids" are DNA molecules that are capable of replicating within a host cell, either extrachromosomally or as part of the host cell chromosome(s), and are designated by a lower case "p" preceded and/or followed by capital letters and/or numbers. The starting plasmids herein are commercially available, are publicly available on an unrestricted basis, or can be constructed from such available plasmids as disclosed herein and/or in accordance with published procedures. In certain instances, as will be apparent to the ordinarily skilled artisan, other plasmids known in the art may be used interchangeably with plasmids described herein.

"Control sequences" refers to DNA sequences necessary for the expression of an operably linked nucleotide coding sequence in a particular host cell. The control sequences that are suitable for expression in prokaryotes, for example, include origins of replication, promoters, ribosome binding sites, and transcription termination sites. The control sequences that are suitable for expression in eukaryotes, for example, include origins of replication, promoters, ribosome binding sites, polyadenylation signals, and enhancers.

An "exogenous" element is one that is foreign to the host cell, or homologous to the host cell but in a position within the host cell in which the element is ordinarily not found.

"Digestion" of DNA refers to the catalytic cleavage of DNA with an enzyme that acts only at certain locations in the DNA. Such enzymes are called restriction enzymes or restriction endonucleases, and the sites within DNA where such enzymes cleave are called restriction sites. If there are multiple restriction sites within the DNA, digestion will produce two or more linearized DNA fragments (restriction fragments). The various restriction enzymes used herein are commercially available and their reaction conditions, cofactors, and other requirements as established by the enzyme manufacturers are used. Restriction enzymes commonly are designated by abbreviations composed of a capital letter followed by other letters representing the microorganism from which each restriction enzyme originally was obtained and then a number designating the particular enzyme. In general, about 1 μg of DNA is digested with about 1–2 units of enzyme in about 20 μl of buffer solution. Appropriate buffers and substrate amounts for particular restriction enzymes are specified by the manufacturer, and/or are well known in the art.

"Recovery" or "isolation" of a given fragment of DNA from a restriction digest typically is accomplished by separating the digestion products, which are referred to as "restriction fragments," on a polyacrylamide or agarose gel by electrophoresis, identifying the fragment of interest on the basis of its mobility relative to that of marker DNA fragments of known molecular weight, excising the portion of the gel that contains the desired fragment, and separating the DNA from the gel, for example by electroelution.

"Ligation" refers to the process of forming phosphodiester bonds between two double-stranded DNA fragments. Unless otherwise specified, ligation is accomplished using known buffers and conditions with 10 units of T4 DNA ligase per 0.5 μg of approximately equimolar amounts of the DNA fragments to be ligated.

"Oligonucleotides" are short-length, single- or double-stranded polydeoxynucleotides that are chemically synthesized by known methods (involving, for example, triester, phosphoramidite, or phosphonate chemistry), such as described by Engels, et al., *Agnew. Chem. Int. Ed. Engl,.* 28:716–734 (1989). They are then purified, for example, by polyacrylamide gel electrophoresis.

"Polymerase chain reaction," or "PCR," as used herein generally refers to a method for amplification of a desired nucleotide sequence in vitro, as described in U.S. Pat. No. 4,683,195. In general, the PCR method involves repeated cycles of primer extension synthesis, using two oligonucleotide primers capable of hybridizing preferentially to a template nucleic acid. Typically, the primers used in the PCR method will be complementary to nucleotide sequences within the template at both ends of or flanking the nucleotide sequence to be amplified, although primers complementary to the nucleotide sequence to be amplified also may be used (Wang, et al., in *PCR Protocols*, pp.70–75 (Academic Press, 1990); Ochman, et al., in *PCR Protocols*, pp. 219–227; Triglia, et al., *Nuc. Acids Res.*, 16:8186 (1988)).

"PCR cloning" refers to the use of the PCR method to amplify a specific desired nucleotide sequence that is present amongst the nucleic acids from a suitable cell or tissue source, including total genomic DNA and cDNA transcribed from total cellular RNA (Frohman, et al., *Proc. Nat. Acad. Sci. USA*, 85:8998–9002 (1988); Saiki, et al., *Science*, 239:487–492 (1 988); Mullis, et al., *Meth. Enzymol.*, 155:33–350 (1987)).

"Stringent conditions" for hybridization or annealing of nucleic acid molecules are those that (1) employ low ionic strength and high temperature for washing, for example, 0.015 M NaCl/0.00 15 M sodium citrate/0.1% sodium dodecyl sulfate (SDS) at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with washes at 42° C. in 0.2×SSC and 0.1% SDS.

"AL-2 nucleic acid" is RNA or DNA that encodes AL-2. "AL-2 DNA" is DNA that encodes AL-2. AL-2 DNA is obtained from cDNA or genomic DNA libraries, or by in vitro synthesis. Identification of AL-2 DNA within a cDNA or a genomic DNA library, or in some other mixture of various DNAs, is conveniently accomplished by the use of an oligonucleotide hybridization probe that is labeled with a detectable moiety, such as a radioisotope (Keller, et al., *DNA Probes*, pp.149–213 (Stockton Press, 1989)). To identify DNA encoding AL-2, the nucleotide sequence of the hybridization probe preferably is selected so that the hybridization probe is capable of hybridizing preferentially to DNA encoding the AL-2 amino acid sequence set forth in FIGS. 1A–1B or 2A–2B, or a variant or derivative thereof as described herein, under the hybridization conditions chosen. Another method for obtaining AL-2 nucleic acid is to chemically synthesize it using one of the methods described, for example, by Engels, et al., *Agnew. Chem. Int. Ed. Engl.*, 28:716–734 (1989). A preferred embodiment is an isolated nucleic acid molecule that includes a nucleotide sequence encoding the amino acid sequence shown in FIGS. 1A–1B or 2A–2B for mature AL-2, and in which, more preferably, the AL-2 codons are contiguous. A preferred nucleotide sequence encoding the amino acid sequence for mature AL-2 can be found in FIGS. 1A–1B or 2A–2B. Also included are AL-2-encoding nucleic acid sequences based on the codon degeneracy of the genetic code.

If the entire nucleotide coding sequence for AL-2 is not obtained in a single cDNA, genomic DNA, or other DNA, as determined, for example, by DNA sequencing or restriction endonuclease analysis, then appropriate DNA fragments (e.g., restriction fragments or PCR amplification products) may be recovered from several DNAs and covalently joined to one another to construct the entire coding sequence. The preferred means of covalently joining DNA fragments is by ligation using a DNA ligase enzyme, such as T4 DNA ligase.

"Isolated" AL-2 nucleic acid is AL-2 nucleic acid that is identified and separated from (or otherwise substantially free from) contaminating nucleic acid encoding another polypeptide or from nucleic acid with which it is normally associated in the natural source of AL-2 nucleic acid. Isolated AL-2 nucleic acid molecules therefore are distinguished from the AL-2 nucleic acid molecule as it occurs naturally in cells. However, an isolated AL-2 nucleic acid molecule includes AL-2 nucleic acid molecules contained in cells that ordinarily express AL-2 where, for example, the nucleic acid molecule is in a chromosomal location different from that of natural cells. The isolated AL-2 nucleic acid can be incorporated into a plasmid or expression vector for in vitro, ex vivo or in vivo use, or can be labeled for diagnostic and probe purposes, using a label as described further herein in the discussion of diagnostic assays and nucleic acid hybridization methods.

For example, isolated AL-2 DNA, or a fragment thereof comprising at least about 15 nucleotides, is used as a hybridization probe to detect, diagnose, or monitor disorders or diseases that involve changes in AL-2 expression, such as may result from neuron damage. In one embodiment of the invention, total RNA in a tissue sample from a patient (that is, a human or other mammal) can be assayed for the presence of AL-2 messenger RNA, wherein the decrease in the amount of AL-2 messenger RNA is indicative of neuronal degeneration.

The present invention further provides antisense or sense oligonucleotides comprising a single-stranded nucleic acid sequence (either RNA or DNA) capable of binding to target AL-2 mRNA (sense) or AL-2 DNA (antisense) sequences. Antisense or sense oligonucleotides, according to the present invention, comprise a fragment of the coding region of AL-2 cDNA. Such a fragment generally comprises at least about 14 nucleotides, preferably from about 14 to about 30 nucleotides. The ability to create an antisense or a sense oligonucleotide, based upon a cDNA sequence for a given protein is described for example, in Stein et al., *Cancer Res.*, 48:2659 (1988) and van der Krol et al., *BioTechniques*, 6:958, 1988. Although not to be restricted by the following working model, it is generally believed that binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides can be used to block expression of AL-2 proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes can be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO4-mediated DNA transfection, electroporation, or other gene transfer vectors such as Epstein-Barr virus or adenovirus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT U.S. application Ser. No. 90/02656). Alternatively, other promoter sequences may be used to express the oligonucleotide. Most preferably, target-tissue specific promoters (either constitutive or inducible) are used.

Sense or antisense oligonucleotides are also introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to specific cell surface receptors. Alternatively, a sense or an antisense oligonucleotide is introduced into a cell containing the target nucleic acid sequence by formation of an oligonucleotide-lipid complex, as described in WO 90/10448. The sense or antisense oligonucleotide-lipid complex is preferably dissociated within the cell by all endogenous lipase.

Isolated AL-2 nucleic acid also is used to produce AL-2 by recombinant DNA and recombinant cell culture methods. In various embodiments of the invention, host cells are transformed or transfected with recombinant DNA molecules comprising an isolated AL-2 DNA, to obtain expression of the AL-2 DNA and thus the production of AL-2 in large quantities. DNA encoding amino acid sequence variants of AL-2 is prepared by a variety of methods known in the art. These methods include, but are not limited to, isolation from a natural source (in the case of naturally occurring amino acid sequence variants of AL-2) or preparation by site-directed (or oligonucleotide-mediated) mutagenesis, PCR mutagenesis, and cassette mutagenesis of an earlier prepared DNA encoding a variant or a non-variant form of AL-2.

Site-directed mutagenesis is a preferred method for preparing substitution, deletion, and insertion variants of AL-2 DNA. This technique is well known in the art (Zoller et al., *Meth. Enz.*, 100:4668–500 (1983); Zoller et al., *Meth. Enz.*, 154:329–350(1987); Carter, *Meth. Enz.*, 154:382–403 (1987); Horwitz al., *Meth. Enz.* 185:599–611 (1990)), and has been used, for example, to produce amino acid sequence variants of trypsin and T4 lysozyme, which variants have certain desired functional properties (Perry et al., *Science*, 226:555–557 (1984); Craik et al., *Science*, 228:291–297 (1985)).

Briefly, in carrying out site-directed mutagenesis of AL-2 DNA, the AL-2 DNA is altered by first hybridizing an oligonucleotide encoding the desired mutation to a single strand of such AL-2 DNA. After hybridization, a DNA polymerase is used to synthesize an entire second strand, using the hybridized oligonucleotide as a primer, and using the single strand of AL-2 DNA as a template. Thus, the oligonucleotide encoding the desired mutation is incorporated in the resulting double-stranded DNA.

Oligonucleotides for use as hybridization probes or primers may be prepared by any suitable method, such as by purification of a naturally occurring DNA or by in vitro synthesis. For example, oligonucleotides are readily synthesized using various techniques in organic chemistry, such as described by Narang et al., *Meth. Enzymol.*, 68:90–98 (1979); Brown et al., *Meth. Enzymol.*, 68:109–151 (1979); and Caruther et al., *Meth. Enzymol.*, 154:287–313 (1985). The general approach to selecting a suitable hybridization probe or primer is well known (Keller et al., *DNA Probes*, pp. 11–18 (Stockton Press, 1989)). Typically, the hybridization probe or primer will contain; 10–25 or more nucleotides, and will include at least 5 nucleotides on either side of the sequence encoding the desired mutation so as to ensure that the oligonucleotide will hybridize preferentially to the single-stranded DNA template molecule.

Multiple mutations are introduced into AL-2 DNA to produce amino acid sequence variants of AL-2 comprising several or a combination of insertions, deletions, or substitutions of amino acid residues as compared to the amino acid sequence set forth in FIGS. 1A–1B or 2A–2B. If the sites to be mutated are located close together, the mutations may be introduced simultaneously using a single oligonucleotide that encodes all of the desired mutations. If, however, the sites to be mutated are located some distance from each other (separated by more than about ten nucleotides), it is more difficult to generate a single oligonucleotide that encodes all of the desired changes. Instead, one of two alternative methods may be employed.

In the first method, a separate oligonucleotide is,generated for each desired mutation. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for introducing a single mutation: a single strand of a previously prepared AL-2 DNA is used as a template, an oligonucleotide encoding the first desired mutation is annealed to this template, and a heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid sequence variants of AL-2 (Higuchi, in *PCR Protocols*, pp. 177–183 (Academic Press, 1990); Vallette et al., *Nuc. Acids Res.*, 17:723–733 (1989)). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, for example, one of the primers is designed to overlap the position of the mutation and to contain the mutation; the sequence of the other primer must be identical to a nucleotide sequence within the opposite strand of the plasmid DNA, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone (Wagner et al., in *PCR Topics*, pp.69–71 (Springer-Verlag, 1991)).

If the ratio of template to product amplified DNA is extremely low, the majority of product DNA fragments incorporate the desired mutation(s). This product DNA is used to replace the corresponding region in the plasmid that served as PCR template using standard recombinant DNA methods. Mutations at separate positions can be introduced simultaneously by either using a mutant second primer, or performing a second PCR with different mutant primers and ligating the two resulting PCR fragments simultaneously to the plasmid fragment in a three (or more)-part ligation.

Another method for preparing variants, cassette mutagenesis, is based on the technique described by Wells et al., *Gene*, 34:315–323 (1985). The starting material is the plasmid (or other vector) comprising the AL-2 DNA to be mutated. The codon(s) in the AL-2 DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the AL-2 DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated AL-2 DNA sequence.

In another embodiment, AL-2 suitable for therapy is AL-2 covalently joined to another protein, such as an immunoglobulin domain (for example, to produce an AL2-IgG fusion protein). Immunoglobulin fusions, immunoadhesins, are chimeric antibody-like molecules that combine the functional domain(s) of a binding protein (in this case AL-2 or its receptor) with the an immunoglobulin sequence. The immunoglobulin sequence preferably (but not necessarily) is an immunoglobulin constant domain. Immunoglobulins (Ig) and certain variants thereof are known and many have been prepared in recombinant cell culture. For example, see U.S. Pat. No. 4,745,055; EP 256,654; Faulkner et al., *Nature*, 298:286 (1982); EP 120,694; EP 125,023; Morrison, *J. Immun.*, 123:793 (1979); Köhler et al., *Proc. Nat'l. Acad. Sci. USA*, 77:2197 (1980); Raso et al., *Cancer Res.*, 41:2073 (1981); Morrison et al., *Ann. Rev. Immunol.*, 2:239 (1984); Morrison, *Science*, 229:1202 (1985); Morrison et al., *Proc. Nat'l. Acad. Sci. USA*, 81:6851 (1984); EP 255,694; EP 266,663; and WO 88/03559. Reassorted-immunoglobulin chains also are known. See for example U.S. Pat. No. 4,444,878; WO 88/03565; and EP 68,763 and references cited therein. The immunoglobulin moiety in the chimeras of the present invention may be obtained from IgG-1, IgG-2, IgG-3 or IgG-4 subtypes, IgA, IgE, IgD or IgM, but preferably IgG-1 or IgG-3.

Chimeras constructed from a receptor sequence linked to an appropriate immunoglobulin constant domain sequence (immunoadhesins) are known in the art. Immunoadhesins reported in the literature include fusions of the T cell receptor* (Gascoigne et al., *Proc. Natl. Acad. Sci. USA*, 84:2936–2940 (1987)); CD4* (Capon et al., *Nature*, 337:525–531 (1989); Traunecker et al., *Nature*, 339:68–70 (1989); Zettmeissl et al., *DNA Cell Biol. USA*, 9:347–353 (1990); Byrn et al., *Nature*, 344:667–670 (1990)); L-selectin (homing receptor) (Watson et al., *J. Cell. Biol.*, 110:2221–2229 (1990); Watson et al., *Nature*, 349:164–167 (1991)); CD44* (Aruffo et al., *Cell*, 61:1303–1313(1990)); CD28* and B7* (Linsley et al., *J. Exp. Med.*, 173721–730 (1991)); CTLA-4* (Lisley et al., *J. Exp. Med.*, 174:61–569 (1991)); CD22* (Stamenkovic et al., *Cell*, 66:1133–1144 (1991)); where the asterisk (*) indicates that the receptor is member of the immunoglobulin superfamily.

The simplest and most straightforward immunoadhesin design combined the binding region(s) of the 'adhesin' protein (in this case AL-2) with the hinge and Fc regions of an immunoglobulin heavy chain. Ordinarily, when preparing chimeras of the present invention, nucleic acid encoding the extracellular domain or a fragment thereof of AL-2 will be fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of AL-2-immunoglobulin chimeras.

In some embodiments, chimeras are assembled as monomers, or hetero- or homo-multimers, and particularly as dimers ortetramers, essentially as illustrated in WO 91/08298. In a preferred embodiment, the AL-2 extracellular domain sequence is fused to the N-terminus of the C-terminal portion of an antibody (in particular the Fc domain), containing the effector functions of an immunoglobulin, e.g., immunoglobulin $G_1$ (IgG-1). It is possible to fuse the entire heavy chain constant region to the AL-2 extracellular domain sequence. Preferably a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In one embodiment, an AL-2 amino acid sequence is fused to the hinge region and CH2 and CH3 or CH1, hinge, CH2 and CH3 domains of an IgG-1, IgG-2, or IgG-3 heavy chain. The precise site at which the fusion is made is not critical, and the optimal site can be determined by routine experimentation. The immunoglobulin portion can genetically engineered or chemically modified to inactivate a biological activity of the immunoglobulin portion, such as T-cell binding, while retaining desirable properties such as its scaffolding property for presenting AL-2 function to an axon or target cell. Chimeras can be assembled as multimers, particularly as homo-dimers or -tetramers. Generally, these assembled immunoglobulins-will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different. Alternatively, the AL-2 extracellular domain sequences can be inserted between immunoglobulin heavy chain and light chain sequences such that an immunoglobulin comprising a chimeric heavy chain is obtained. In this embodiment, the sequences are fused to the 3' end of an immunoglobulin heavy chain in each arm of an immunoglobulin, either between the hinge and the CH2 domain, or between the CH2 and CH3 domains (see Hoogenboom et al., *Mol. Immunol.*, 28:1027–1037 (1991)). The presence of an immunoglobulin light chain is not required in the immunoadhesins of the present invention; an immunoglobulin light chain might be present either covalently associated to a immunoglobulin heavy chain fusion polypeptide, or directly fused to the AL-2 extracellular domain. In the former case, DNA encoding an immunoglobulin light chain is typically coexpressed with the DNA encoding the AL-2-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Preparation of such structures are, for example, disclosed in U.S. Pat. No. 4,816,567 issued Mar. 28, 1989. The immunoglobulin sequences used in the construction of the immunoadhesins of the present invention can be from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger 'adhesin' domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For AL-2-Ig immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life i approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m1 and 2) are located in the Fc region; and one of these sites G1m1, is non-immunogenic. In contrast, there are 12 serologically-defined allotypes in IgG3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

In designing the chimeras of the present invention domains that are not required for neurotrophin binding and/or biological activity may be deleted. In such structures, it is important to place the fusion junction at residues that are located between domains, to avoid misfolding. With respect to the parental immunoglobulin, a useful joining point is just upstream of the cysteines of the hinge that form the disulfide bonds between the two heavy chains. In a frequently used design, the codon for the C-terminal residue of the 'adhesin' part of the molecule is placed directly upstream of the codons for the sequence DKTHTCPPCP (SEQ ID NO:6 of the IgG1 hinge region.

The general methods suitable for the construction and expression of immunoadhesins are the same those disclosed hereinabove with regard to (native or variant) AL-2. For example, AL-2-Ig immunoadhesins are most conveniently constructed by fusing the cDNA sequence encoding the AL-2 portion in-frame to an Ig cDNA sequence. However, fusion to genomic Ig fragments can also be used (see, e.g., Gascoigne et al., *Proc. Natl. Acad. Sci. USA*, 84:2936–2940 (1987); Aruffo et al., *Cell*, 61:1303–1313 (1990); Stamenkovic et al., *Cell*, 66:1133–1144 (1991)). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the 'adhesin' and the Ig parts of the immunoadhesin are inserted in tandem into a plasmid vector that directs' efficient expression in the chosen host cells. For expression in mammalian cells pRK5-based vectors (Schall et al., *Cell*, 61:361–370 (1990)) and CDM8-based vectors (Seed, *Nature*, 329:840 (1989)). The exact junction can be created by removing the extra sequences between the designed junction codons using oligonucleotide-directed deletional mutagenesis (Zoller et al., *Nucleic Acids Res*., 10:6487 (1982); Capon et al., *Nature*, 337:525–531 (1989)). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of AL-2-Ig immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently, with pRK5-based vectors by a modification of the calcium phosphate method to allow efficient immunoadhesin expression. CDM8-based vectors can be used to transfect COS cells by the DEAE-dextran method (Aruffo et al., *Cell*, 61:1303–1313 (1990); Zettmeissl et al., *DNA Cell Biol*., (US) 9:347–353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts (Gascoigne et al., *Proc. Natl. Acad. Sci. USA*, 84:2936–2940 (1987); Martin et al., *J. Virol*., 67:3561–3568 (1993)).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., *J. Immunol. Meth*., 62:1–13 (1983)). Protein G is recommended for all mouse isotypes and for human γ3 (Guss et al., *EMBO J*., 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens et al., *Anal. Biochem.*, 159:217–226 (1986)) and immobilized metal chelate chromatography (Al-Mashikhi et al., *J. Dairy Sci.*, 71:1756–1763 (1988)). In contrast to antibodies, however, their behavior on ion exchange columns is dictated not only by their isoelectric points, but also by a charge dipole that may exist in the molecules due to their chimeric nature.

If desired, the immunoadhesins can be made bispecific, that is, directed against two distinct ligands. Thus, the immunoadhesins of the present invention can have binding specificities for AL-2, or can specifically bind to a AL-2 and to an other determinant, for example one specifically expressed on the cells expressing a receptor to which the AL-2 portion of the immunoadhesin structure binds. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

This application encompasses chimeric polypeptides comprising AL-2 fused to another polypeptide (such as the immunoadhesins mentioned above). In one preferred embodiment, the chimeric polypeptide contains a fusion of the AL-2 (or a fragment thereof, e.g., the ECD of the AL-2) with a tag polypeptide which provides an epitope to which an anti-tag antibody can selectively bind. The epitope tag is generally provided at the amino- or carboxyl- terminus of the AL-2. Such epitope-tagged-AL-2 can be detected using a labelled antibody against the tag polypeptide. Also, the epitope tag allows AL-2 to be readily purified by anti-tag antibody affinity purification. Affinity purification techniques and diagnostic assays involving antibodies are well-known.

Tag polypeptides and their respective antibodies are well known in the art. Examples include the flu HA tag polypeptide and its antibody 12CA5, (Field et al., *Mol. Cell. Biol.*, 8:2159–2165 (1988)); the c-myc tag and the 8F9, 3C7, 6E10, G4, B7 and 9E10 antibodies thereto (Evan et al., *Molecular and Cellular Biology*, 5(12):3610–3616 (1985)); and the Herpes Simplex virus glycoprotein D (gD) tag and its antibody (Paborsky et al., *Protein Engineering*, 3(6): 547–553 (1990)). Other tag polypeptides have been disclosed. Examples include the Flag-peptide (Hopp et al., *BioTechnology*, 6:1204–1210 (1988)); the KT3 epitope peptide (Martin et al., *Science*, 255:192–194 (1992)); an α-tubulin epitope peptide (Skinner et al., *J. Biol. Chem.*, 266:15163–15166 (1991)); and the T7 gene 10 protein peptide tag (Lutz-Freyermuth et al., *Proc. Natl. Acad. Sci. USA*, 87:6393–6397 (1990). Once the tag polypeptide has been selected, an antibody thereto can be generated using the techniques disclosed herein.

The general methods suitable for the construction and production of epitope tagged AL-2 are-the same as those disclosed herein with regard to (native or variant) AL-2. AL-2-tag polypeptide fusions are most conveniently constructed by fusing the cDNA sequence encoding the AL-2 portion in-frame to the tag polypeptide DNA sequence and expressing the resultant DNA fusion construct in appropriate host cells. Ordinarily, nucleic acid encoding the AL-2 (or a fragment thereof) will be fused at its 3' end to nucleic acid encoding the N-terminus of the tag polypeptide, however 5' fusions are also possible.

Epitope tagged AL-2 can be conveniently purified by affinity chromatography using the anti-tag antibody. The matrix to which the affinity antibody is attached is most often agarose, but other matrices are available (e.g. controlled pore glass or poly(styrenedivinyl)benzene). The epitope tagged AL-2 can be eluted from the affinity column by varying the buffer pH or ionic strength or adding chaotropic agents, for example.

In another embodiment of the invention, multimeric soluble ligands are prepared by expression as chimeric molecules utilizing flexible linker loops. A DNA construct encoding the chimeric protein is designed such that it expresses two or more soluble or extracellular domains fused together in tandem (e.g., "head-to-head") by a flexible loop. This loop may be entirely artificial (e.g. polyglycine repeats interrupted by serine or threonine at a certain interval) or "borrowed" from naturally occurring proteins (e.g. the hinge region of hIgG). Molecules can be engineered in which the length and composition of the loop is varied, to allow for selection of molecules with desired characteristics. Although not wishing to be limited by theory, it is believed that membrane attachment of the ligands can facilitate ligand clustering, which in turn can promote receptor multimerization and activation. Thus, one means of obtaining biological activity of the soluble AL-2 is mimicking, in solution, membrane associated ligand clustering. Thus, a biologically active, clustered soluble Eph-family ligand comprises (soluble AL-2)$_n$, wherein the soluble AL-2 is the receptor-binding AL-2 extracellular domain and n is 2 or greater. For example, despite the fact that receptor phosphorylation is markedly induced by stimulating receptor expressing reporter cells with mammalian cells overexpressing membrane-linked forms of the ligands AL-1 or B61, there is little or no observable phosphorylation using soluble forms of these ligands. However, when secreted forms of B61 are myc-tagged and antibodies are used to cluster the ligands, or When AL-1-IgG chimera is used, the previously inactive soluble ligands strongly induce receptor tyrosine phosphorylation in reporter cells expressing Ehk-1 or Rek7 receptors, respectively. Dimerization of the soluble ligand, e.g., utilizing Fc, can be sufficient for achieving a biological response, however, further clustering of the ligand according to the invention, for example using anti-Fc antibodies, may achieve an increase in biological activity. Cells of the present invention may transiently or, preferably, constitutively and permanently express AL-2 in native form, or in soluble form as chimeric tagged AL-2, AL-2 immunoadhesin, or clustered AL-2 as described herein.

Accordingly, a method of enhancing the biological activity of the soluble AL-2 or its ECD is provided that includes the steps of (a) expressing the soluble domain of AL-2 with an epitope tag and (b) exposing the tagged soluble domain to anti-tag antibodies. The position of the tag with respect to AL-2 is not important so long as the tag does not interfere with AL-2 function and, in turn, AL-2 does not interfere with tag function. The tag is preferably located at either termini of AL-2, more preferably at the C-terminus of AL-2. However, the tag may be attached by covalent means, including with oxime linkages as taught for example in WO 9425071 published Nov. 11, 1994.

In additional embodiments are compounds of the formula (AL-2)$_n$X, where n is an integer greater than or equal to 2 and X is an organic linker covalently binding each AL-2. For example, AL-2 dimers and multimers can be made by attaching AL-2 peptides to an organic linker or baseplate (designated as X in the formula) using methods and linkers (e.g., baseplates or templates) described in the art, for example in WO 94/25071, WO 95/19567, or WO 95/04543. Accordingly, a biologically active, soluble AL-2 is provided that contains 2 or greater number of soluble AL-2 peptides where the soluble AL-2 is the AL-2 extracellular domain that binds an Eph-family receptor. Preferably n is 2 to 20, more preferably 2 to 10, even more preferably 2 to 4. In one preferred embodiment n is 2. For example, multiple AL-2 are covalently attached to the same baseplate, e.g., an organic molecule such as a penta-lysine, where each AL-2 is attached site-specifically via a covalent linkage, e.g., an oxime linkage, which can be formed by reaction of a reactive group on AL-2 with its complementary reactive group on,the baseplate. Oxime linkages have superior hydrolysis stability over a range of physiological conditions compared to hydrazones, etc. Oxime linkages are not commonly subject to enzymatic hydrolysis. Polyoximes are therefore suited to applications where integrity and stability of the complex is desired. The linker (or baseplafe) should not interfere with AL-2 activity. Baseplates can be designed to improve solubility of peptides, as well as to present peptides to receptors. A chemically reactive group suitable for oxime linkage formation can be site-specifically added to AL-2 through methods known in the art (see for example WO 90/02135, WO 94/25071, or EP 243929 B1 issued Sep. 27, 1995).

It is apparent that AL-2 antagonists can be prepared or used applying the above guidelines appropriately. For example, a AL-2-binding Eph-family-receptor-IgG chimera fusion (see Winslow et al., Neuron, 14:973–981 (1995)), for a method of making receptor-IgG fusions by recombinant means that is suitable for use with other Eph-family receptors and their extracellular domains) or anti-AL-2 antibody can be adsorbed onto a membrane, such as a silastic membrane, which can be implanted in proximity to tumors or arthritic tissue, or can be incorporated into liposomes (see for example WO 91/04014 published Apr. 4, 1991).

It will be appreciated that some screening of the recovered variant will be needed to select one having the desired activity. A change in the immunological character of the AL-2 molecule, such as affinity for a given antibody, can be measured by a competitive-type immunoassay. The variant is assayed for changes in the suppression or enhancement of its enzymatic activity by comparison to the activity observed for native AL-2 in the same assay. For example, one can screen for the ability of the variant AL-2 to stimulate protein kinase activity of an Eph-family receptor using the techniques set forth, for example, in Lokker et al., EMBO J., 11:2503–2510 (1992), Winslow et al., Neuron, 14:973–981 (1995), or Bennett et al., J. Biol. Chem., 269(19):14211–8 (1994). Other potential modifications of protein or polypeptide properties such as redox or thermal stability, hydrophobicity, susceptibility to proteolytic degradation, or the tendency to aggregate with carriers or into multimers are assayed by methods well known in the art.

AL-2 DNA, whether cDNA or genomic DNA or a product of in vitro synthesis, is ligated into a replicable vector for further cloning or for expression. "Vectors" are plasmids and other DNAs that are capable of replicating autonomously within a host cell, and as such, are useful for performing two functions in conjunction with compatible host cells (a vector-host system). One function is to facilitate the cloning of the nucleic acid that encodes the AL-2, i.e., to produce usable quantities of the nucleic acid. The other function is to direct the expression of AL-2. One or both of these functions are performed by the vector-host system. The vectors will contain different components depending upon the function they are to perform as well as the host cell with which they are to be used for cloning or expression.

To produce AL-2, an expression vector will contain nucleic acid that encodes AL-2 as described above. The AL-2 of this invention is expressed directly in recombinant cell culture, or as a fusion with a heterologous polypeptide, preferably a signal sequence or other polypeptide having a specific cleavage site at the junction between the heterologous polypeptide and the AL-2.

In one example of recombinant host cell expression, mammalian cells are transfected with an expression vector comprising AL-2 DNA and the AL-2 encoded thereby is recovered from the culture, preferably cell culture medium in which the recombinant host cells are grown. But the expression vectors and methods disclosed herein are suitable for use over a wide range of prokaryotic and eukaryotic organisms.

Prokaryotes may be used for the initial cloning of DNAs and the construction of the vectors useful in the invention. However, prokaryotes may also be used for expression of DNA encoding AL-2. Polypeptides that are produced in prokaryotic host cells typically will be non-glycosylated.

Plasmid or viral vectors containing replication origins and other control sequences that are derived from species compatible with the host cell are used in connection with prokaryotic host cells, for cloning or expression of an isolated DNA. For example, E. coli typically is transformed using pBR322, a plasmid derived from an E. coli species (Bolivar, et al., Gene, 2:95–113 (1987)). PBR322 contains genes for ampicillin and tetracycline resistance so that cells transformed by the plasmid can easily be identified or selected. For it to serve as an expression vector, the pBR322 plasmid, or other plasmid or viral vector, must also contain, or be modified to contain, a promoter that functions in the host cell to provide messenger RNA, (mRNA) transcripts of a DNA inserted downstream of the promoter (Rangagwala, et al., Bio/Technology, 9:477–479 (1991)).

In addition to prokaryotes, eukaryotic microbes, such as yeast, may also be used as hosts for the cloning or expression of DNAs useful in the invention. Yeast, for example, Saccharomyces cerevisiae, is a commonly used eukaryotic microorganism. Plasmids useful for cloning or expression in yeast cells of a desired DNA are well known, as are various promoters that function in yeast cells to produce mRNA transcripts.

Furthermore, cells derived from multicellular organisms also may be used as hosts for the cloning or expression of DNAs useful in the invention. Mammalian cells are most commonly used, and the procedures for maintaining or propagating such cells in vitro, which procedures are commonly referred to as tissue culture, are well known. Kruse and Patterson, eds., Tissue Culture (Academic Press, 1977). Examples of useful mammalian cells are human cell lines such as 293, HeLa, and WI-38, monkey cell lines such as COS-7 and VERO, and hamster cell lines such as BHK-21 and CHO, all of which are publicly available from the American Type Culture Collection (ATCC), Rockville, Md. 20852 USA.

Expression vectors, unlike cloning vectors, should contain a promoter that is recognized by the host organism and is operably linked to the AL-2 nucleic acid., Promoters are untranslated sequences that are located upstream from the start codon of a gene and that control transcription of the gene (that is, the synthesis of mRNA). Promoters typically fall into two classes, inducible and constitutive. Inducible promoters are promoters that initiate high level transcription of the DNA under their control in response to some change in culture conditions, for example, the presence or absence of a nutrient or a change in temperature.

A large number of promoters are known, that may be operably linked to AL-2 DNA to achieve expression of AL-2 in a host cell. This is not to say that the promoter associated with naturally occurring AL-2 DNA is not usable. However, heterologous promoters generally will result in greater transcription and higher yields of expressed AL-2.

Promoters suitable for use with prokaryotic hosts include the β-lactamase and lactose promoters, (Goeddel et al., *Nature*, 281:544–548 (1979)), tryptophan (trp) promoter, (Goeddel et al., *Nuc. Acids Res.*, 8:4057–4074 (1980)), and hybrid promoters such as the tac promoter, (deBoer et al., *Proc. Natl. Acad. Sci. USA*, 80:21–25 (1983)). However, other known bacterial promoters are suitable. Their nucleotide sequences have been published, (Siebenlist et al., *Cell*, 20:269–281 (1980)), thereby enabling a skilled worker operably to ligate them to DNA encoding AL-2 using linkers or adaptors to supply any required restriction sites (Wu et al., *Meth. Enz.*, 152:343–349 (1987)).

Suitable promoters for use with yeast hosts include the promoters for 3-phosphoglycerate kinase, (Hitzeman et al., *J. Biol. Chem.*, 255:12073–12080 (1980); Kingsman et al., *Meth. Enz.*, 185:329–341 (1990)), or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase (Dodson et al., *Nuc. Acids Res.*, 10:2625–2637 (1982); Emr, *Meth. Enz.*, 185:231–279 (1990)).

Expression vectors useful in mammalian cells typically include a promoter derived from a virus. For example, promoters derived from polyoma virus, adenovirus, cytomegalovirus (CMV), and simian virus 40 (SV40) are commonly used. Further, it is also possible, and often desirable, to utilize promoter or other control sequences associated with a naturally occurring DNA that encodes AL-2, provided that such control sequences are functional in the particular host cell used for recombinant DNA expression.

Other control sequences that are desirable in an expression vector in addition to a promoter are a ribosome binding site, and in the case of an expression vector used with eukaryotic host cells, an enhancer. Enhancers are cis-acting elements of DNA, usually about from 10–300 bp, that act on a promoter to increase the level of transcription. Many enhancer sequences are now known from mammalian genes (for example, the genes for globin, elastase, albumin, α-fetoprotein and insulin). Typically, however, the enhancer used will be one from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers (Kriegler, *Meth. Enz.*, 185:512–527 (1990)).

Expression vectors may also contain sequences necessary for the termination of transcription and for stabilizing the messenger RNA (mRNA) (Balbas et al., *Meth. Enz.*, 185:14–37 (1990)); Levinson, *Meth. Enz,*. 185:485–511 (1990)). In the case of expression vectors used with eukaryotic host cells, such transcription termination sequences may be obtained from the untranslated regions of eukaryotic or viral DNAs or cDNAs. These regions contain polyadenylation sites as well as transcription termination sites (Birnsteil et al., *Cell*, 41:349–359 (1985)).

In general, control sequences are DNA sequences necessary for the expression of an operably liked coding sequence in a particular host cell. "Expression" refers to transcription and/or translation. "Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic,oligonucleotide adaptors or linkers are used, in conjunction with standard recombinant DNA methods.

Expression and cloning vectors also will contain a sequence that enables the vector to replicate in one or more selected host cells. Generally, in cloning vectors this sequence is one that enables the vector to replicate independently of the host chromosome(s), and includes origins of replication or autonomously replicating sequences. Such sequences are well known for a variety of bacteria, yeast, and viruses. The origin of replication from the plasmid pBR322 is suitable for most gram-negative bacteria, the 2μ plasmid origin is suitable for yeast, and various viral origins (for example, from SV40, polyoma, or adenovirus) are useful for cloning vectors in mammalian cells. Most expression vectors are "shuttle" vectors, i.e., they are capable of replication in at least one class of organisms but can be transfected into another organism for expression. For example, a vector may be cloned in *E. coli* and then the same vector is transfected into yeast or mammalian cells for expression even though it is not capable of replicating independently of the host cell chromosome.

The expression vector may also include an amplifiable gene, such as that comprising the coding sequence for dihydrofolate reductase (DHFR). Cells containing an expression vector that includes a DHFR gene may be cultured in the presence of methotrexate, a competitive antagonist of DHFR. This leads to the synthesis of multiple copies of the DHFR gene and, concomitantly, multiple copies of other DNA sequences comprising the expression vector (Ringold et al., *J. Mol. Apl. Genet.*, 1: 165–175 (1981)), such as a DNA sequence encoding AL-2. In that manner, the level of AL-2 produced by the cells may be increased.

DHFR protein encoded by the expression vector also may be used as a selectable marker of successful transfection. For example, if the host cell prior to transformation is lacking in DHFR activity, successful transformation by an expression vector comprising DNA sequences encoding AL-2 and DHFR protein can be determined by cell growth in medium containing methotrexate. Also, mammalian cells transformed by an expression vector comprising DNA sequences encoding AL-2, DHFR protein, and aminoglycoside 3' phosphotransferase (APH) can be determined by cell growth in medium containing an aminoglycoside antibiotic such as kanamycin or neomycin. Because eukaryotic cells do not normally express an endogenous APH activity, genes encoding APH protein, commonly referred to as neo$^r$ genes, may be used as dominant selectable markers in a wide range of eukaryotic host cells, by which cells transfected by the vector can easily be identified or selected (Jiminez et al., *Nature*, 287:869–871 (1980); Colbere-Garapin et al., *J. Mol. Biol.*, 150:1–14 (1981); Okayama et al., *Mol. Cell. Biol.*, 3:280–289(1983)).

Many other selectable markers are known that may be used for identifying and isolating recombinant host cells that express AL-2. For example, a suitable selection marker for use in yeast is the trp1 gene present in the yeast plasmid YRp7 (Stinchcomb et al., *Nature*, 282:39–43 (1979); Kingsman et al., *Gene*, 7:141–152 (1979); Tschemper, et al., *Gene*, 10: 157–166 (1980)). The trp1 gene provides a selection marker for a mutant strain of yeast lacking the ability to grow in tryptophan, for example, ATCC No. 44076 or PEP4-1 (available from the American Type Culture Collection, Rockville, Md. 20852 USA) (Jones, *Genetics*, 85:12 (1977)). The presence of the trp1 lesion in the yeast host cell genome then provides an effective environment for detecting transformation by growth in the absence of tryptophan. Similarly, Leu2-deficient yeast strains (ATCC Nos. 20622 or 38626) are complemented by known plasmids bearing the Leu2 gene.

Accordingly, a method for producing AL-2 is provided that includes the steps of transforming a cell containing an endogenous AL-2 gene with a homologous DNA comprising an amplifiable gene and a flanking sequence of at least about 150 base pairs that is homologous with a DNA sequence within or in proximity to the endogenous AL-2 gene, whereby the homologous DNA integrates into the cell genome by recombination, then culturing the cells under conditions that select for amplification of the amplifiable gene whereby the AL-2 gene is also amplified, and thereafter recovering AL-2 from the cells.

For diagnostic applications, anti-AL-2 antibodies typically will be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; radioactive isotopic labels, such as, e.g., $^{125}$I, $^{32}$P, $^{14}$C, or $^3$H, or an enzyme, such as alkaline phosphatase, beta-galactosidase or horseradish peroxidase.

Any method known in the art for separately conjugating the antibody to the detectable moiety may be employed, including those methods described by David et al., *Biochemistry*, 13:1014–1021 (1974); Pain et al., *J. Immunol. Meth.*, 40:219–231 (1981); and Bayer et al., *Meth. Enz.*, 184:138–163 (1990).

The anti-AL-2 antibodies may be employed in any known assay method, such as competitive binding assays, direct and indirect sandwich assays, and immunoprecipitation assays (Zola *Monoclonal Antibodies: A Manual of Techniques*, pp.147–158 (CRC Press, Inc., 1987)). The term "antibody" is used in the broadest sense and specifically covers single anti-AL-2 monoclonal antibodies (including agonist and antagonist antibodies) and anti-AL-2 antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-AL-2 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g., U.S. Pat. No. 4,816,567 and Mage et al., *Monoclonal Antibody Production Techniques and Applications*, pp.79–97 (Marcel Dekker, Inc., New York (1987)).

Thus, the modifier "monoclonal" indicates the character of the antibody as being obtained from a substantially homogeneous population of antibodies, and is not to be construed as requiring production of the antibody by any particular method. Monoclonal antibodies include hybrid and recombinant antibodies produced by splicing a variable (including hypervariable) domain of an anti-AL-2 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g., Mage et al., *Monoclonal Antibody Production Techniques and Applications*, pp.79–97 (Marcel Dekker, Inc., New York (1987)). The monoclonal antibodies to be used in accordance with the present invention can be made by hybridoma method known in the art, or may be made by recombinant DNA methods (U.S. Pat. No. 4,816,567). The "monoclonal antibodies" may also be isolated from phage libraries generated using the techniques described in McCafferty et al., *Nature*, 348:552–554 (1990), for example. The individual antibodies comprising the monoclonal antibody population are identical except for possible naturally-occurring mutations that may be present in minor amounts.

"Humanized" forms of non-human (e.g. murine) antibodies are specific chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or. substantially all of the FR regions are those of a human immunoglobulin consensus sequence. The humanized antibody optimally also will comprise at least a portion of an immunoglobulin constant region (Fc), typically that of a human immunoglobulin.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567 by Cabilly et al.) wherein substantially less than an intact human variable domain has been substituted by the corresponding sequence from a non-human species. In practice, humanized antibodies are typically human antibodies in which some CDR residues, and possibly some FR residues, are substituted by residues from analogous sites' in rodent antibodies.

It is important that antibodies be humanized with;retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see WO 92/22653, published Dec. 23, 1992.

Bispecific antibodies are monoclonal, preferably human or humanized, antibodies that have binding specificities for at least two different antigens. In the present case, one of the binding specificities is for a AL-2, the other one is for any other antigen, and preferably for a receptor or receptor subunit. For example, bispecific antibodies specifically binding a Htk receptor and AL-2 are within the scope of the present invention.

Methods for making bispecific antibodies are known in the art. Traditionally, the recombinant production of bispecific antibodies is based on the coexpression of two immunoglobulin heavy chain-light chain pairs, where the two heavy chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829, published May 13, 1993, and in Traunecker et al., *EMBO J.*, 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Competitive binding assays rely on the ability of a labeled standard (e.g., AL-2 or an immunologically reactive portion thereof) to compete with the test sample analyte (AL-2) for binding with a limited amount of antibody. The amount of AL-2 in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex (for example, see U.S. Pat. No. 4,376,110). The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

AL-2 antibodies may be useful in certain therapeutic indications to block activity of the AL-2 (for example in carcinogenesis).

Therapeutic AL-2 antibody formulations and modes for administration will be similar to those described herein for AL-2. A typical daily dosage of the antibody ranges from about 1 $\mu$g/kg to up to 5 mg/kg or more, depending on the factors mentioned herein for AL-2 administration.

AL-2 antibodies may also be useful in diagnostic assays for AL-2, e.g., detecting its expression in specific cells, tissues, or serum. The antibodies are labeled in the same fashion as AL-2 described above and/or are immobilized on an insoluble matrix. AL-2 antibodies also are useful for the affinity purification of AL-2 from recombinant cell culture or natural sources. AL-2 antibodies that do not detectably cross-react with other proteins can be used to purify AL-2 free from these other known proteins. Suitable diagnostic assays for AL-2 and its antibodies are described herein.

The anti-AL-2 antibodies of the invention also are useful for in vivo imaging, wherein an antibody labeled with a detectable moiety is administered to a host, preferably into the bloodstream, and the presence and location of the labeled antibody in the host is assayed. This imaging technique is useful in the staging and treatment of various neurological disorders. The antibody may be labeled with any moiety that is detectable in a host, whether by nuclear magnetic resonance, radiology, or other detection means known in the art.

Neutralizing anti-AL-2 antibodies are useful as antagonists of AL-2. The term "neutralizing anti-AL-2 antibody" as used herein refers to an antibody that is capable of specifically binding to AL-2, and which is capable of substantially inhibiting or eliminating the functional activity of AL-2 in vivo or in vitro. Typically a neutralizing antibody will inhibit the functional activity of AL-2 at least about 50%, preferably greater than 80%, and more preferably greater than 90% as determined, for example, by an in vitro receptor binding assay, or in vitro cell-based receptor activation assays (for example, see Winslow et al., Neuron, 14:973–981 (1995)).

Other AL-2 antagonists are prepared using AL-2 receptor proteins. One example of an AL-2 antagonist is an Eph-family-receptor-IgG chimeric protein that binds AL-2 as described herein. Another example of an AL-2 antagonist is a soluble form of an AL-2 receptor, which comprises the extracellular domain or the receptor substantially free of the transmembrane domain. The soluble form of the receptor can be used directly as an antagonist, or it can be used to screen for small molecules that would antagonize AL-2 activity.

As stated previously, receptor tyrosine kinases are involved in many signal transduction events that regulate important cellular processes. Such processes include, for example, cellular differentiation and proliferation. Abnormal regulation or expression of the signal transduction machinery can lead to aberrant and malignant growth of the abnormally regulated cells. Abnormal expression of Eph is known to be associated with carcinomas of the liver, lung, breast and colon, for example. Likewise, since some Eph-related tyrosine kinases are, at least, found within the same tissues as Eph, their abnormal expression may also lead to the development of the carcinomas described above as well as other types of cancers. Additionally, cancers of the neuronal linage are likely to be caused by the abnormal expression or regulation of Cek5, since this Eph-related kinase is found exclusively in neuronal tissues. Cek5 and the other Eph-related kinases expressed in the nervous system also are likely to be involved in nerve regeneration. A change in the amount or activity of an Eph-related kinase in a sample, compared to a normal sample, will be indicative of cancerous stages and of their level of malignancy. Depending on whether the normal state is caused by the presence or absence of an Eph-related kinase, the change can involve either an increase or decrease in the amount or activity of the Eph-related kinase. One skilled in the art can measure these parameters and compare them to those obtained from a normal sample. Methods for determining the levels or activity of Eph-related kinases are known to one skilled in the art and include, for example, RNA and protein blot analysis, ELISA using specific antibodies to each of the Eph-related kinases and direct measurement of catalytic activity such as tyrosine kinase activity. Such methods can be found in Harlow et al., Antibodies: A Laboratory Manual Cold Spring Harbor Laboratory (1989), which is incorporated herein by reference. The compositions and methods of receptor modulation as taught herein can then be effectively applied where AL-2-binding receptors are involved.

AL-2 is believed to find therapeutic use for treating mammals via stimulation or inhibition of growth and/or differentiation and/or activation and/or metabolism of cells having a receptor for AL-2 as described herein, such as Htk, Hek2, or Hek5. The interaction of ligand and receptor may result in activation of the receptor and transduction of a signal which modulates the physiological state of the receptor-bearing cells. The ligand can act as a growth factor to stimulate the proliferation of target cells. Alternatively, ligand binding may not activate the receptor. In this instance, the ligand may act as an antagonist for other molecules which activate the receptor and induce signal transduction.

The invention provides a method of modulating the endogenous enzymatic activity of an AL-2-binding Eph-family receptor. The method includes the step of administering to a mammal an effective amount of AL-2 to modulate the receptor enzymatic activity. In one embodiment is provided a method for stimulating the proliferation, differentiation, metabolism, regeneration, growth, process-out growth, or cell migration of AL-2-receptor expressing cells in a mammal by administering a therapeutically effective amount of receptor-activating AL-2. Receptor-activating forms of AL-2, such as AL-2-IgG, find use in alleviating cell damage or promoting neurogenesis following disease or injury, such as cytotoxicity, caused by chemotherapy. For example, a method for stimulating proliferation of neurons innervating the liver includes the step of administering a therapeutically effective amount of AL-2. Treatment with AL-2 is useful for repairing liver damage resulting from disease or injury.

Soluble Eph-family-receptor polypeptides can be used to modulate the activation of the cell-associated receptors, typically by competing with the cell-bound receptor for unbound AL-2. Modulation of Eph-family receptor activation may in turn alter the proliferation and/or differentiation of receptor-bearing cells.

Antibodies to Eph-like receptors are useful reagents for the detection of receptors in different cell types using immunoassays conventional to the art. Antibodies are also useful therapeutic agents for modulating receptor activation. Antibodies may bind to the receptor so as to directly or indirectly block ligand binding and thereby act as an antagonist of receptor activation. Alternatively, antibodies may act as an agonist by binding to receptor so as to facilitate ligand binding and bring about receptor activation at lower ligand concentrations. In addition, antibodies can themselves act as a ligand by inducing receptor activation. In this context the present invention provides anti-idiotype antibodies, i.e., anti-AL-2-antibodies, that recognize an AL-2-binding-Eph-family receptor.

Accordingly, a method for modulating the activation of an AL-2-binding-Eph-family receptor by administering a modulation-effective amount of AL-2 or soluble AL-2. The term "modulation-effective amount" is that amount which effects an increase or decrease in the activation of an AL-2-binding-Eph-family receptor. Preferably the amount will range from about 0.01 μg to about 100 mg of polypeptide per kg body weight. In general, for therapeutic purposes, therapy will be appropriate for a patient having a condition in part related to the state of proliferation and/or differentiation of receptor-bearing cells. Based in part upon the tissue distribution of AL-2, and thus presumably its receptors in some embodiments, treatment with the pharmaceutical compositions of the invention may be particularly indicated for disorders involving brain, heart, muscle, lung, kidney, pancreas, skeletal muscle, liver, and more preferably involving brain, pancreas, and skeletal muscle.

AL-2 is also useful for selection of cell populations enriched for AL-2-receptor bearing cells. Such populations can be useful in cellular therapy regimens where it is necessary to treat patients that are depleted of certain cell types.

The human AL-2 is clearly also useful insofar as it can be administered to a human having depressed levels of endogenous AL-2, preferably in the situation where such depressed levels lead to a pathological disorder.

The prominent expression of AL-2 DNA in the cerebellum, cerebral cortex, medulla, spinal cord, occipital pole, frontal lobe, temporal lobe, putamen, amygdala, caudate nucleus, corpus callosum, hippocampus, substantia nigra, subthalamic nucleus, and thalamus (see Examples) is consistent with the use of AL-2 to treat neurodegenerative diseases or, other neuronal disorders or conditions in which these structures, or neurons projecting to these structures, are affected.

AL-2 finds use in treating neurodegenerative disorders or nerve damage where nerve regeneration and (re)establishment of neuronal pathways are desired outcomes, since it may play a role in neuronal cell migration and axonogenesis. A critical stage in the development of the nervous system, and during nerve regeneration as might occur after injury, is the projection of axons to their targets. Navigational decisions are made at the growth cones of the migrating axons. As axons grow their growth cones extend and retract filopodia and lamellipodia processes which are implicated in the navigational decisions and pathfinding abilities of migrating axons. Like peripheral nervous system axons, the growth cones of neurons associated with the central nervous system follow stereotyped pathways and apparently can selectively choose from a number of possible routes (reviewed by Goodman et al., *Cell*, 72:77–98 (1993)). For example, subcellular localization of a Hek5 homolog, the murine Nuk receptor tyrosine kinase, indicates that this receptor is concentrated at sites of cell-cell contact, often involving migrating neuronal cells or their extensions (Henkemeyer et al., *Oncogene*, 9:1001–14 (1994)). Most notably, high levels of Nuk protein are found within initial axon outgrowths and associated nerve fibers. The axohal localization of Nuk was transient and not detected after migrations have ceased, which suggests a role for this tyrosine kinase during the early pathfinding and/or fasciculation stages of axonogenesis, which can be important processes during recovery from neuronal damage.

Accordingly, AL-2 (and embodiments disclosed herein or identified by the methods presented herein) is believed to be useful in promoting the development, maintenance, regeneration, migration, or process-outgrowth of neurons in vivo, including central (brain and spinal chord), peripheral (sympathetic, parasympathetic, sensory, and enteric neurons), and motoneurons. The ligands, agonists and antagonists may accordingly be used to stimulate or inhibit these activities associated with neurodegenerative conditions and conditions involving trauma and injury to the nervous system. Consequently, AL-2 may be utilized in methods for the diagnosis and/or treatment of a variety of neurologic diseases and disorders.

In some embodiments of the invention, purified AL-2 can be administered to patients in whom the nervous system has been damaged by trauma, surgery, stroke, ischemia, infection, metabolic disease, nutritional deficiency, malignancy, or toxic agents, to promote the survival or growth of neurons. For example, AL-2 can be used to promote the survival or growth of motoneurons that are damaged by trauma or surgery. Also, AL-2 can be used to treat motoneuron disorders, such as amyotrophic lateral sclerosis (Lou Gehrig's disease), Bell's palsy, and various conditions involving spinal muscular atrophy, or paralysis. AL-2 can be used to treat human neurodegenerative disorders, such as Alzheimer's disease, Parkinson's disease, epilepsy, demyelinating diseases, such as multiple sclerosis, Huntington's chorea, Down's Syndrome, nerve deafness, Meniere's disease, and other disorders of the cerebellum (Hefti, *Neurobiol.*, 25(11):1418–35 (1994); Marsden, *Lancet*, 335:948–952 (1990); Agid, *Lancet*, 337:1321–132 Wexler et al., *Ann. Rev. Neurosci.*, 14:503–529 1991)). AL-2 can be used as cognitive enhancer, to enhance learning particularly in dementias or trauma, since they can promote axonal outgrowth and synaptic plasticity, particularly of hippocampal neurons that express AL-2-binding Eph-family receptors and cortical neurons that express AL-2. AL-2 can be used in bacterial and viral infections of the nervous system, deficiency diseases, such as Wernicke's disease and nutritional polyneuropathy, progressive supranuclear palsy, Shy Drager's syndrome, multistem degeneration and olivo ponto cerebellar atrophy, and peripheral nerve damage.

For example, in Alzheimer's disease there is a critical loss of basal forebrain cholinergic neurons, cortical neurons, and hippocampal neurons. Although maximally effective treatment of this neurodegenerative condition may require protection of all vulnerable neuronal populations, treatment with AL-2 alone is expected to provide therapeutic benefit. Alzheimer's disease, which has been identified by the National Institutes of Aging as accounting for more than 50% of dementia in the elderly, is also the fourth or fifth leading cause of death in Americans over 65 years of age. Four million Americans, 40% of Americans over age 85 (the fastest growing segment of the U.S. population), have Alzheimer's disease. Twenty-five percent of all patients with Parkinson's disease also suffer from Alzheimer's disease-like dementia. And in about 15% of patients with dementia, Alzheimer's disease and multi-infarct dementia coexist. The third most common cause of dementia, after Alzheimer's disease and vascular dementia, is cognitive impairment due to organic brain disease related directly to alcoholism, which occurs in about 10% of alcoholics. However, the most consistent abnormality for Alzheimer's disease, as well as for vascular dementia and cognitive impairment due to organic brain disease related to alcoholism, is the degeneration of the cholinergic system arising from the basal forebrain (BF) to both the codex and hippocampus (Bigl et al., in *Brain Cholinergic Systems*, M. Steriade and D. Biesold, eds., Oxford University Press, Oxford, pp.364–386 (1990)). And there are a number of other neurotransmitter systems affected by Alzheimer's disease (Davies, *Med. Res. Rev.*, 3:221 (1983)). However, cognitive impairment, related for example to degeneration of the cholinergic neurotransmitter system, is not limited to individuals suffering from dementia. It has also been seen in otherwise healthy aged adults and rats. Studies that compare the degree of learning impairment with the degree of reduced cortical cerebral blood flow in aged rats show a good correlation (Berman et al., *Neurobiol Aging*, 9:691 (1988)). In chronic alcoholism the resultant organic brain disease, like Alzheimer's disease and normal aging, is also characterized by diffuse reductions in cortical cerebral blood flow in those brain regions where cholinergic neurons arise (basal forebrain) and to which they project (cerebral cortex) (Lofti et al., Cerebrovasc.and Brain Metab. Rev. 1:2 (1989)).

The progressive nature of Parkinson's disease is due to a loss of nigral dopaminergic neurons of the substantia nigra (Studer et al., *Eur. J. Neuroscience*, 7:223–233 (1995)). ALS involves progressive degeneration of motoneurons of the spinal cord, brain stem and cerebral cortex.

Further, AL-2 can be used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to distal sensorimotor neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine.

AL-2 may play a role in neurogenesis, for example in axon bundling or process outgrowth. The following mechanism is not meant to be limiting to the invention. Any role of AL-2 in axon fascicle formation may be indirect, i.e. AL-2 and its receptor, may not themselves function as adhesion molecules but rather are involved in regulating the fasciculation process. Accordingly, activation of AL-2-receptor expressed on the neurons, by AL-2 expressed on astrocytes for example, might activate a signaling pathway that promotes fasciculation, possibly by up-regulating or activating adhesion molecules. Activation of AL-2-receptor may cause growth cone repulsion and collapse, forcing axons together for fasciculation. AL-2 expressed on astrocytes would serve as a repulsive cue to axons driving axons together. This model is compatible with the current view that astrocytes play an important role during development of the CNS, where they are thought to provide a substratum and trophic support for growing axons (Hatten et al., *Semin. Neurosci.*, 2:455–465 (1990)).

A tyrosine kinase is required for axon bundling. Neurons in the developing or regenerating nervous system presumably require two types of factors, those that promote growth and survival, and those that provide spatial or directional guidance in the establishment of neuronal pathways (Tessier-Lavigne, *Curr. Opin.Genet. Devel.*, 4:596–601 (1994)). Tyrosine kinases are known to play a well-established role in the former and can participate in the latter. Accordingly, AL-2 can play role in the formation of neuronal pathways, a crucial feature of both development and regeneration in the nervous system.

In still further embodiments of the invention, AL-2 antagonists, and especially anti-AL-2 antibodies, can be administered to patients suffering from neurologic diseases and disorders characterized by excessive production or activity of AL-2. AL-2 antagonists can be used in the prevention of aberrant regeneration of sensory neurons such as may occur post-operatively, or in the selective ablation of sensory neurons, for example, in the treatment of chronic pain syndromes.

In yet another embodiment AL-2 stimulates hematopoiesis and thus find use in treating hematopoietic-related disorders. Htk, a candidate receptor for AL-2, has a wide tissue distribution including expression in several myeloid hematopoietic cell lines (Bennett et al., *J. Biol. Chem.* 269:14211–8 (1994)). Hematopoietic expression of Htk in the monocytic lineage (myeloid but not lymphoid hematopoietic cells) indicates that AL-2, upon Htk binding and activation, can activate differentiation and/or proliferation of these cells, finding use in treating conditions such as anemia, bone marrow transplant (autologous or otherwise) or as adjunct therapy in chemo- or radiation-therapies. Furthermore, AL-2 antagonists can reduce or prevent differentiation and/or proliferation of these cells, a function that finds particular use in disease conditions involving malignant forms of these cells, for example, in treating acute myeloid leukemia (AML), chronic myeloid leukemia (CML), or myelodysplastic syndrome (MDS). AL-2 antagonists can be administered in conjunction with other agents or therapies for AML or CML.

The development of a vascular supply, angiogenesis, is essential for the growth, maturation, and maintenance of normal tissues, including neuronal tissues. It is also required for wound healing and the rapid growth of solid tumors and is involved in a variety of other pathological conditions. Current concepts of angiogenesis, based in large part on studies on the vascularization of tumors, suggest that cells secrete angiogenic factors which induce endothelial cell migration, proliferation, and capillary formation. Numerous factors have been identified which induce vessel formation in vitro or in vivo in animal models. These include FGFα, FGFβ, TGF-α, TNF-α, VPF or VEGF, monobutyrin, angiotropin, angiogenin, hyaluronic acid degradation products, and more recently, B61 for TNF-α-induced angiogenesis (Pandey et al., *Science*, 268:567–569 (1995)). Inhibitors of angiogenesis include a cartilage-derived inhibitor identified as TIMP, PF-4, thrombospondin, laminin peptides, heparin/cortisone, minocycline, fumagillin, difluoromethyl ornithine, sulfated chitin derivatives, and B61 antibody. The major development of the vascular supply occurs during embryonic development, at ovulation during formation of the corpus luteum, and during wound and fracture healing. Many pathological disease states are characterized by augmented angiogenesis including tumor growth, diabetic retinopathy, neovascular glaucoma, psoriasis, and rheumatoid arthritis. During these processes normally quiescent endothelial cells which line the blood vessels sprout from sites along the vessel, degrade extracellular matrix barriers, proliferate, and migrate to form new vessels. Angiogenic factors, secreted from surrounding tissue, direct the endothelial cells to degrade stromal collagens, undergo directed migration (chemotaxis), proliferate, and reorganize into capillaries.

AL-2 may stimulate either the growth or differentiation of cells expressing an AL-2 receptor. AL-2 that induces differentiation of AL-2-receptor bearing may be useful in the treatment of certain types of cancers. AL-2 may be used alone or in combination with'standard chemotherapy or radiation therapy for cancer treatment. Where an AL-2-receptor is shown to be involved in the development of a cancerous state, either through stimulation of cell growth or through promotion of metastasis by stimulating cell mobility and adhesion, AL-2 antagonists as taught herein will find use. Fragments or analogs of AL-2 that bind to but do not activate the receptor are useful antagonists. Administration of an antagonist having affinity for the receptor will block receptor binding and activation by endogenous activators. Administration of soluble AL-2 receptor may also be used to counteract the biological effects of receptor activation. Soluble AL-2 receptor will compete with endogenous cell surface receptors for binding to activators, including AL-2, and thereby reduce the extent of AL-2 receptor activation. In addition, monoclonal antibodies directed either to AL-2 or to the receptor may be useful in blocking the interactions of AL-2, or other activator, with AL-2 receptors on cell surfaces.

Accordingly, AL-2 can find further use in promoting or enhancing angiogenesis by receptor activation on endothelial or stromal cells. The induction of vascularization is a critical component of the wound healing process. Neovascularization, also known as angiogenesis, is a complex process involving several sequential steps including basement membrane degradation, endothelial cell mobilization and proliferation, vessel canalization, and new basement membrane formation (Mantovani, *Int. J. Cancer*, 25:617 (1980)). Vascularization ensures that proliferating and differentiating fibroblasts are supplied with nutrients and oxygen, and that elements of humoral and cellular immunity are delivered to sites of potential bacterial infection. It is desirable to induce neovascularization as early as possible in the course of wound healing, particularly in the case of patients having conditions that tend to retard wound healing, e.g., burns, decubitus ulcers, diabetes, obesity and malignancies. Even normal post-surgical patients will be benefited if they can be released from hospital care at any earlier date because of accelerated wound healing. This invention provides novel compositions and methods for modulating angiogenesis. A patient bearing a wound can be treated by applying an angiogenically active dose of an AL-2 compound to the wound; This facilitates the neovascularization of surgical incisions, burns, traumatized tissue, skin grafts, ulcers and other wounds or injuries where accelerated healing is desired. In individuals who have substantially impaired wound healing capacity, thereby lack the ability to provide to the wound site endogenous factors necessary for the process of wound healing, the addition of exogenous AL-2 and compositions of the invention enable wound healing to proceed in a normal manner. The proteins of the present invention are expected to accelerate the healing process in a broad spectrum of wound conditions. Novel topical compositions containing an Al-2 compound are provided for use in the inventive method, as are novel articles such as sutures, grafts and dressings containing an AL-2 compound. The term "wound" is defined herein as any opening in the skin, mucosa or epithelial linings, most such openings generally being associated with exposed, raw or abraded tissue. There are no limitations as to the type of wound or other traumata that can be treated in accordance with this invention, such wounds including (but are not limited to): first, second and third degree burns (especially second and third degree); surgical incisions, including those of cosmetic surgery; wounds, including lacerations, incisions, and penetrations; and ulcers, e.g., chronic non-healing dermal ulcers, including decubital ulcers (bed-sores) and ulcers or wounds associated with diabetic, dental, hemophilic, malignant and obese patients. Furthermore, normal wound-healing may be retarded by a number of factors, including advanced age, diabetes, cancer, and treatment with anti-inflammatory drugs or anticoagulants, and the proteins described herein may be used to offset the delayed wound-healing effects of such treatments.

Although the primary concern is the healing of major wounds by neovascularization, it is contemplated that an AL-2 compound may also be useful for minor wounds, and for cosmetic regeneration of epithelial cells. Preferably, the wounds to be treated are burns and surgical incisions, whether or not associated with viral infections or tumors. In most cases wounds are not the result of a tumor or a viral infection and ordinarily they do not include tumor cells.

AL-2 is preferably delivered to wounds by topical application, "topical" in this context meaning topical to the wound, and does not necessarily refer to epidermal application. When applied topically, the AL-2 compound is usually combined with other ingredients, such as carriers and/or adjuvants. There are no limitations on the nature of such other ingredients, except that they must be pharmaceutically acceptable, efficacious for their intended administration, and cannot degrade or inactivate AL-2. AL-2 is applied to burns in the form of an irrigant or salve, and if so then in an isotonic solution such as physiological saline solution or D5W. AL-2 is particularly useful in accelerating the growth and survival of skin grafts applied to burns. Ordinarily, an AL-2-containing composition is impregnated into the grafts or adherently coated onto the face of the graft, either on the side of the graft to be applied to the burn or on the exterior side of the graft. AL-2 also is included in burn debridement salves which contain proteases so long as the debridement enzyme does not proteolytically inactivate the AL-2.

AL-2 is impregnated into surgical articles in accordance with this invention, such articles being defined as items to be contacted with wounds which articles are typically water adsorbent or hydratable and which have a therapeutic utility in treating wounds. Examples of surgical articles are dressings, sutures, pledgets, skin grafting films (including living skin grafts as well as collagen-containing membranes or synthetic skin substitutes) and the like as will be known to the clinician: Dressings for use herein generally comprise water adsorbent laminates containing AL-2 to be adherently placed into contact with wounds. Improved dressings for use with AL-2 as described herein preferably will have a membrane such as a dialysis membrane interposed between the wound surface and the adsorbent substance in the dressing, the membrane containing pores sufficiently small for AL-2 to diffuse into the wound but not sufficiently large for epithelial cells to penetrate into the adsorbent. The degree of adsorbency will vary considerably and in fact dressings are included herein which are nonadsorbent, i.e., the AL-2 is deposited or stored in an aqueous reservoir which is used to irrigate the wound on a continuous or intermittent basis.

AL-2 also is formulated into ointments or suspensions, preferably in-combination with purified collagen, in order to produce semisolid or suspension vehicles. Conventional oleaginous formulations containing AL-2 are useful as salves. Such AL-2 carriers and formulations release AL-2 on a sustained basis at the wound, thereby serving to create a chemotactic gradient that directionally orients neovascularization, e.g., into a skin graft. Sustained release formulations for AL-2 include semipermeable polymer matrices in the form of shaped articles, e.g., films, or microcapsules. Implantable sustained release matrices include copolymers of L-glutamic acid and gamma ethyl-L-glutamate (Sidman et al., *Biopolymers*, 22(1):547–556 (1983)), poly (2-hydroxyethyl-methacrylate) (Langer et al., *J. Biomed. Mater. Res.*, 15:167–277 (1981) and Langer, *Chem. Tech.*, 12:98–105 (1982)), ethylene vinyl acetate (Langer et al., Id.), or poly-D-(–)-3-Hydroxybutyric acid (EP 133,988A). These formulations may function as bio-erodible matrices or as stable sources for the passive diffusion of AL-2.

Sustained release AL-2 compositions for contact with wounds also include liposomally entrapped AL-2. Liposomes containing AL-2 are prepared by methods known per se: DE 3,218,121 A; Epstein et al., *Proc. Natl. Acad. Sci. USA*, 82:3688–3692 (1985); Hwang et al., *Proc. Natl. Acad. Sci. USA*, 77:4030–4034 (1980); EP 52322A; EP 36676A; EP 88046A; EP 143949A; EP 142641A; Japanese patent application 83–118008; U.S. Pat. Nos. 4,485,045 and 4,544,545; and EP 102,324A. Ordinarily the liposomes are of the small (about 200–800 Angstroms) unilamellar type in which the lipid content is greater than about 30 mol. % cholesterol, the selected proportion being adjusted for the optimal rate of AL-2 leakage.

AL-2 is formulated with other ingredients such as carriers and/or adjuvants, e.g., albumin, nonionic surfactants and other emulsifiers. There are no limitations on the nature of such other ingredients, except that they must be pharmaceutically acceptable, efficacious for their intended administration, and cannot degrade the activity of the active ingredients of the compositions. Suitable adjuvants include collagen or hyaluronic acid preparations, fibronectin, factor XIII, or Other proteins or substances designed to stabilize or otherwise enhance the active therapeutic ingredient(s).

AL-2 optionally is supplied with other known angiogenic agents such as heparin, which has been shown to accelerate the healing of thermal burns, TNF, TGF-α, TGF-β, fibroblast growth factor, epidermal growth factor, B61, angiogenin, platelet factor 4, insulin, PDGF, and angiogenesis factor and the angiogenic activity of the combinations observed for synergistic effects. AL-2 optionally also is combined with an with an IFN, e.g., IFN-γ, and other cytokines, or may be free of interferons such as IFN-γ. Where such cytokines or known angiogenic agents are species-specific, the appropriate cytokine or agent will be selected for the species to be treated.

Animals or humans are treated in accordance with this invention. It is possible but not preferred to treat an animal of one species with AL-2 of another species. A preferred AL-2 for use herein is soluble AL-2-IgG.

The amount of AL-2 to be contacted with the wound depends upon a great number of variables that will be taken into account by the clinician, including the presence of other angiogenic agents in the AL-2 formulations, the nature of the wound to be treated, the condition of the patient, the AL-2 formulation selected, the neovascularizing activity of the molecular species of AL-2 chosen and the route of administration. Lesser amounts of AL-2 typically are administered when the AL-2 is formulated into a sustained release vehicle, e.g., dressing or ointment, and when the AL-2 is administered by direct topical contact rather than impregnated into a bandage or dressing. Concentrations in the range of 0.10 ng/ml–100 ug/ml may be used. The typical topical formulation will be capable of delivering a concentration of AL-2-IgG, or equivalent, at the neovascularization target site (for example, a skin graft) in a range of about from 0.10 ng/ml to 10000 ng/ml, more preferably 0.20 ng/ml to 1000 ng/ml, and even more preferably 0.25 ng/ml to 350 ng/ml, although this therapeutic dose range is subject to considerable variation as noted above. Delivery of concentrations outside of this range may offer certain of the benefits of AL-2 neovascularization, but the clinician will be expected to monitor dosages in order to optimize performance of AL-2 in wound healing. It also should be noted that the weight amount will vary for other AL-2 variants and forms if their molecular weight and/or angiogenic potency differ from that of AL-2-IgG. Potency differences are easily determined by comparing the degree of neovascularization achieved with the candidate AL-2 and AL-2-IgG in any of the assays set forth in the Examples herein.

Accordingly, a method for accelerating the neovascularization of a wound is provided that includes the step of applying to the wound an angiogenically effective dose of a composition comprising tumor necrosis factor. The composition can be applied topically by direct contact with the wound, particularly when the wound is a fresh surgical incision. In a preferred embodiment the composition further comprises collagen or a synthetic skin substitute. The caregiver may further administer to the wound a growth factor, an antibiotic, a debridement agent, and/or angiogenin. A preferred composition for the debridement of burns contains an AL-2 compound and a proteolytic enzyme which does not inactivate the neovascularizing activity of AL-2. The therapeutic compositions can be reapplied at one-to-several-day-intervals until healing is complete.

Therapeutic options for patients with vascular disease, particularly vascular obstructive disease, are sometimes limited. Such patients are often refractory to conservative measures and typically unresponsive to drug therapy (Takeshita et al., *J. Clin. Invest.*, 93:662–670 (1994)). When vascular obstruction is lengthy and/or widespread, nonsurgical revascularization may not be feasible. Surgical therapy, consisting of arterial bypass and/or amputation, may be complicated by a variable morbidity and mortality, and is often dependent for its efficacy upon short- and long-term patency of the conduit used. Therapeutic angiogenesis constitutes an alternative treatment strategy for such patients. The present invention provides methods for enhancing angiogenesis in a mammal comprising administering to the mammal an effective amount of AL-2. The AL-2 alone may be administered to the mammal, or alternatively, may be administered to the mammal in combination with other therapies and/or pharmacologic agents. In particular AL-2 finds use in patients suffering from vascular insufficiency or limb ischemia secondary to arterial occlusive disease. The effects of AL-2 proteins of the invention on angiogenesis can be tested, for example, in a rabbit model of hindlimb ischemia. This rabbit model was designed to simulate ischemia characteristics of patients with severe lower extremity arterial occlusive disease and is performed essentially as described in Takeshita et al., *J. Clin. Invest.*, 93:662–670 (1994). Measurements of calf blood pressure (BP) index; angiographic score of collateral formation; intravascular Doppler-wire analysis of blood flow; and microsphere-based analysis of muscle perfusion at rest and during stress are performed.

AL-2 antagonists can find use in inhibiting, preventing or treating pathological angiogenesis, such as during tumor vascularization. Tumor neovascularization is a vital stage in the growth of solid tumors (Polverini et al., *Lab. Invest.*, 51:635–642 (1985)). The progressive growth of solid tumors is strictly dependent on their ability to attract new blood vessels that will supply them with oxygen and essential nutrients (Bouck, *Cancer Cells*, 2(6): 179–185 (1990)). Angiogenesis has been shown to precede or accompany malignancy. In the absence of neovascularization the size of tumor grafts becomes limited. When angiogenesis is absent, tumors tend to remain dormant. Therefore, angiogenic activity has been directly correlated with tumor growth. AL-2 antagonist compositions and methods of the invention can modulate (e.g., prevent or reduce) new capillary growth into tumors.

A variety of non-neoplastic diseases, previously thought to be unrelated, can be considered "angiogenic diseases" because they are dominated by the pathological growth of capillary blood vessels. These diseases include diabetic retinopathy, arthritis, hemangiomas, psoriasis, and ocular neovascularization. AL-2 antagonist compositions and methods of the invention can be used to treat these conditions.

Vascularization also plays a critical role in chronic inflammatory conditions such as rheumatoid arthritis (Koch et al., *Arthr. Rheum.*, 29:471–479 (1986)). Rheumatoid arthritis ("RA") is a chronic heterogeneous disorder in which a variety of etiological agents may be responsible for initiating a series of events leading to inflammation in multiple joints. The cause of the disease remains unknown, although by analogy with other forms of arthritis such as that accompanying Lyme disease, it has been postulated that infection with as yet unidentified bacteria or viruses in a genetically susceptible host is an initiating event. Persistence could result from the presence of viral or bacterial antigens that generate an immune response or cross-react with host tissues together with amplification effects of cellular products of the host. While many patients have systemic manifestations in RA, many of the most serious consequences of RA stem from its effects on articular connective tissues, which are characterized by alterations of the synovial membrane with proliferation of lining cells and infiltration by chronic inflammatory cells. Erosions of bone occur in areas contiguous with the inflammatory cell mass as well as in regions adjacent to bone marrow distant from the inflammation. The bone erosions are probably produced through induction of differentiation and activation of osteoclast progenitors. The erosion of soft connective tissues, e.g., cartilage, joint capsules, tendons, and ligaments, results from direct release of proteolytic enzymes from cells of the inflammatory cell mass or from polymorphonuclear leukocytes that are typically abundant in rheumatoid synovial fluids, although rare in the synovial membrane. See, for example, Harris, W. N. Kelley et al., eds., *Textbook of Rheumatology*, W. B. Saunders, Philadelphia, pp. 886–915 (1985); Dayer et al., *Clin. Rheum. Dis.*, 4:517–537 (1978); Krane, *Arthritis and Allied Conditions. A textbook of Rheumatology*, ed. by D. J. McCarty, pp. 593–604, Lea and Febiger, Philadelphia (1985); and Krane et al., *Lymphokines*, 7:75–136 (1982). Therapy for RA depends on the stage of the disease. Stage 1, where a postulated antigen is presented to T-cells with no obvious arthritic symptoms, is not treated. Stage 2 involves T-cell and B-cell proliferation and angiogenesis in synovial membrane, resulting in malaise, mild joint stiffness, and swelling. During Stage 3, neutrophils accumulate in synovial fluid and synovial cells proliferate without polarization or invasion of cartilage, resulting in joint pain and swelling, morning stiffness, malaise, and weakness. Current therapy for Stages 2 and 3 includes bed rest, application of heat, supplemental eicosapentaenoic and docosahexanoic acid, and drugs. Nonsteroidal anti-inflammatory drugs, including aspirin, continue to be the foundation of drug therapy in treating Stages 2 and 3 of the disease. Those anti-inflammatory drugs other than aspirin include indomethacin, phenylbutazone, phenylacetic acid derivatives such as ibuprofen and fenoprofen, naphthalene acetic acids (naproxen), pyrrolealkanoic acid (tometin), indoleacetic acids (sulindac), halogenated anthranilic acid (meclofenamate sodium), piroxicam, zomepirac, and diflunisal. Second-line drugs for RA Stages 2 and 3 include anti-malarial drugs such as hydroxychloroquine, sulfasalazine, gold salts, and penicillamine, and low-dose methotrexate. These alternatives frequently produce severe side effects, including retinal lesions and kidney and bone marrow toxicity. The irreversible destruction of cartilage occurs in Stage 4 of the disease. Currently available drugs and treatments include total lymphoid irradiation, high-dose intravenous methylprednisolone, and cyclosporine. Cyclosporine is nephrotoxic and the other treatments exert substantial toxicity as well. As a result, such immunosuppressive agents heretofore have been used only in the treatment of severe and unremitting RA. Other possible therapeutic drugs for Stage 4 of RA include cyclic oligosaccharides (cyclodextrins), which, when combined with a noninflammatory steroid (cortexolone), inhibit angiogenesis in vivo. Folkman et al., *Science* 243:1490–1493 (1989). Antibodies against crucial components of the early phase of the immune response include anti-Class II MHC antibodies (Gaston et al., *Arthritis Rheum.*, 31:21–30 (1988); Sany et al., *Arthriutis Rheum.*, 25:17–24 (1982)), anti-interleukin-2 receptor antibodies (Kyle et al., *Ann. Rheum. Dis.*, 48:428–429 (1989)), 20 anti-CD4 antibodies (Herzog et al., *J. Autoimmun.*, 2:627–642 (1989); Walker et al., *J. Autoimmun.*, 2:643–649 (1989)), and antithymocyte globulin (Shmerling et al., *Arthritis Rheum.*, 32:1495–1496 (1989)). The last three of these drugs have been used in patients with RA. The present invention provides compositions and methods that down-regulate inflammatory and proliferative pathways in RA by modulating the associated angiogenesis. The compositions contain an angiogenesis-modulating effective amount of an AL-2 antagonist. The compositions can further comprise other angiogenesis-modulating agents, particularly agents for treating RA as discussed above or agents for treating tumors. The methods involve the step of administering an angiogenesis-modulating effective amount of an AL-2 antagonist to a mammal in need of such treatment. By "modulating" in the context of conditions in which angiogenesis is undesirable is meant blocking, inhibiting, preventing, reversing, or reducing angiogenesis, or preventing further progression of angiogenesis.

There seems to be little or no biochemical difference between angiogenic peptides expressed by tumors and those expressed by normal tissues. Nor are there any morphological differences between the new capillaries that respond to a malignancy and the capillary growth that occurs during physiological neovascularization (Folkman et al., *Science*, 235:442–447 (1987)). As there is no qualitative difference between the angiogenic capabilities of nonmalignant and malignant diseases, results from normal and malignant vascularization assays can be easily compared, and progress can be made in either area independently of the system of investigation used (Paweletz et al., *Critical Reviews in Oncology/Hematology*, 9(3):197–198 (1989)). Thus, the invention relates to a method comprising inhibiting angiogenesis by administering an effective amount of AL-2 antagonist. The invention comprises a method for the treatment of angiogenesis-dependent diseases by administering an effective amount of AL-2 antagonist to a mammal. Angiogenesis dependent diseases include, but are not limited to diabetic retinopathy, arthritis, tumor growth and metastasis, neovascular glaucoma, retinopathy of prematurity, senile macular degeneration, and hypergeneration of scars after wound healing. The pharmaceutical composition of the present invention exhibit therapeutic properties and, preventative or inhibitive properties against diseases associated with angiogenesis, for example, inflammatory diseases (e.g., rheumatoid arthritis), diabetic retinopathy, tumors such as malignant tumors (e.g., cancer such as mastocarcinoma, hepatoma, colic carcinoma, Kaposi's sarcoma, lung carcinomas and other epithelial carcinomas).

Numerous methods, in vitro and in vivo, are available to screen candidate AL-2 or AL-2 antagonists compounds for angiogenic or angiogenesis-inhibiting properties. Several in vitro assays of endothelial cell growth, migration, and capillary tube formation are known and can be used with the compounds of the invention, particularly as initial screening methods for angiogenic or angiostatic substances. Further testing would typically use in vivo animal testing. U.S. Pat. No. 5,382,514, which is incorporated herein, describes numerous models for angiogenesis in vivo. For example, the corneal pocket assay involves the surgical implantation of polymer pellets containing angiogenic factors in the cornea of larger animals such as rabbits. Since quantitation can be difficult the assay is usually used for preferred candidate compounds. The rabbit ear chamber assay requires the surgical insertion of a glass or plastic viewing device and measurement of capillary migration by microscopy. The rat dorsal air sac assay involves implants of stainless steel chambers containing angiogenic factors. An alginate assay which generates an angiogenic response has been described which involves the injection of tumor cells encased in alginate subcutaneously into mice. The accumulation of hemoglobin in the injected gel is used to quantitate the angiogenic response. A compound can be administered to the chorio-allantoic membranes of aged, typically three-day-aged, fertilized chicken eggs and the appearance of neovascularization after a lapse of time, typically two days is observed (CAM assay; Ausprunk et al., *Am. J. Pathol.*, 97:597 (1975)). The neovascularization inhibitory rates are compared with an untreated control group. A more recent assay method involves providing a liquid matrix material which forms a matrix gel when injected into a host; adding an angiogenic agent to the liquid matrix material; injecting the liquid matrix material containing the angiogenic agent into a host to form a matrix gel; recovering the matrix gel from the host; and quantitating angiogenesis of the recovered matrix gel. A variation of this can be used to test for inhibitors of vascularization in a tissue by providing a liquid matrix material which forms a matrix gel when injected into a host; adding an angiogenic inhibiting agent to the liquid matrix material; and injecting the liquid matrix material containing the angiogenic inhibiting agent into a tissue situs of a host to form a matrix gel. This system can be used with compounds of the invention when inducing vascularization in a tissue is desired by providing a liquid matrix material which forms a matrix gel when injected into a host; adding an angiogenic inducing agent to the liquid matrix material; and injecting the liquid matrix material containing the angiogenic inducing agent into a tissue situs of a host to form a matrix gel. In a preferred embodiment, a solution of basement membrane proteins supplemented with fibroblast growth factor and heparin is injected subcutaneously in a host, e.g., a mouse, where it forms a gel. Sprouts from vessels in the adjacent tissue penetrate into the gel within days connecting it with the external vasculature. Angiogenesis is then quantitated by image analysis of vessels and by measuring the hemoglobin present in the vessels within the gel. This assay method facilitates the testing of both angiogenic and angiostatic agents in vivo. In addition, the endothelial cells responding to the angiogenic factors can be recovered in vitro for further studies. Preferred compounds have 50–70% inhibition rates, and more preferred compounds show 80–100% inhibition rates. As described herein the angiogenically active proteins of the invention provide use in in vitro and in vivo screens for compounds that inhibit angiogenesis by measuring inhibition of AL-2 stimulated angiogenesis in the presence and absence of the candidate inhibitor.

Therapeutic formulations of AL-2 and AL-2 antagonists for treating neurologic diseases and disorders and for modulating angiogenesis and other disorders ate prepared by mixing AL-2 or AL-2 antagonist, e.g., anti-AL-2 antibody or a soluble AL-2-binding-Eph-receptor, having the desired degree of purity, with optional physiologically acceptable carriers,:excipients, or stabilizers which are well known. Acceptable carriers, excipients or stabilizers are nontoxic at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

It may be desirable to adsorb AL-2 onto a membrane, such as a silastic membrane, which can be implanted in proximity to damaged neural tissue, or to incorporate AL-2 into liposomes (PCT Pat. Pub. No. WO 91/04014, published Apr. 4, 1991).

AL-2 optionally is combined with or administered in concert with other neurotrophic factors to achieve a desired therapeutic effect. For example, AL-2 may be used together with NGF, NT-3, BDNF, NT-4/5, an insulin-like growth factor (e.g., IGF-1, IGF-2, or IGF-3) or another neurotrophic factor to achieve a synergistic stimulatory effect on the growth of sensory neurons, wherein the term "synergistic" means that the effect of the combination of AL-2 with a second substance is greater than that achieved with either substance used individually.

AL-2 and AL-2 antagonists to be used for in vivo administration must be sterile. This is readily accomplished by filtration of a solution of AL-2 or anti-AL-2 antibody through sterile filtration membranes. Thereafter, the filtered solution may be placed into a container having a sterile access port, for example, an intravenous solution bag or vial having a stopper pierceable by a hypodermic injection needle. The filtered solution also may be lyophilized to produce sterile AL-2 or anti-AL-2 antibody in a powder form.

Methods for administering AL-2 and AL-2 antagonists in vivo include injection or infusion by intravenous, intraperitoneal, intracerebral, intrathecal, intramuscular, intraocular, intraarterial, or intralesional routes, and by means of sustained-release formulations.

Sustained-release formulations generally consist of AL-2 or AL-2 antagonists and a matrix from which the AL-2 or AL-2 antagonists are released over some period of time. Suitable matrices include semipermeable polymer matrices in the form of shaped articles, for example, membranes, fibers, or microcapsules. Sustained release matrices may comprise polyesters, hydrogels, polylactides, U.S. Pat. No. 3,773,919, copolymers of L-glutamic acid and gamma ethyl-L-glutamate, Sidman, et al., *Biopolymers*, 22: 547–556 (1983), poly (2-hydroxyethyl-methacrylate), or ethylene vinyl acetate, Langer, et al., *J. Biomed. Mater. Res.*, 15: 167–277 (1981); Langer, *Chem. Tech.*, 12:98–105 (1982).

In one embodiment of the invention, the therapeutic formulation comprises AL-2 or AL-2 antagonist entrapped within or complexed with liposomes. For example, AL-2 covalently joined to a glycophosphatidyl-inositol moiety may be used to form a liposome comprising AL-2. In a further embodiment, the therapeutic formulation comprises cells actively producing AL-2 or AL-2 antagonist. Such cells may be directly introduced into the tissue of a patient, or may be encapsulated within porous membranes which are then implanted in a patient, in either case providing for the delivery of AL-2 or anti-AL-2 antagonist into areas within the body of the patient in need of increased or decreased concentrations of AL-2. Alternatively, an expression vector comprising AL-2 DNA may be used for in vivo transformation of a patient's cells to accomplish the same result.

An effective amount of AL-2 or AL-2 antagonist, e.g., anti-AL-2 antibody, to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 100 mg/kg or more, depending on the factors mentioned above. Where possible, it is desirable to determine appropriate dosage ranges first in vitro, for example, using assays for neuronal cell survival or growth which are known in the art, and then in suitable animal models, from which dosage ranges for human patients may be extrapolated. In a specific embodiment of the invention, a pharmaceutical composition effective in promoting the survival or growth of neurons will provide a local growth promoting activity concentration in vivo of between about 0.1 and 10 ng/ml. Typically, the clinician will administer AL-2 until a dosage is reached that achieves the desired effect. Therapeutic progress is easily monitored by conventional assays.

In the treatment of tumors the compositions described herein can be administered subcutaneously or intramuscularly, for example, and the pharmacological activities of an AL-2 antagonist can be maintained over a long period of time by the sustained-release effect of a composition of the present invention. The number of administrations can therefore be reduced. The composition can also be by directly injecting the composition into a tumor-controlling artery. In the case of treatment of an adult patient having a tumor, the dose of the AL-2 antagonist can be appropriately selected depending upon the kind of tumor, site, size, and kind of AL-2 antagonist. For example, the dose of a protein AL-2 antagonists, particularly an antibody, can be-about 0.1 mg to about 500 mg, typically about 1.0 mg to about 300 mg, more typically about 25 mg to about 100 mg. The administration frequency can be appropriately selected depending upon the kind of disease and dosage form. In the case of injection into the tumor-controlled artery or tumor itself, frequently repeated injections are not required and a single injection once every one to 4 weeks may be sufficient for the desired therapeutic effects.

The nucleic acid encoding the AL-2 may be used as a diagnostic for tissue-specific typing. For example, such procedures as in situ hybridization, Northern and Southern blotting, and PCR analysis, can be used to determine whether DNA and/or RNA encoding AL-2 is present in the cell type(s) being evaluated. AL-2 nucleic acid or polypeptide may also be used as diagnostic markers for such tissues. For example, the AL-2 may be labeled, using the techniques described herein, and expression of AL-2-receptor, including the preferred receptors disclosed herein, receptor can be quantified via its binding to labelled AL-2.

AL-2 nucleic acid is also useful for the preparation of AL-2 polypeptide by recombinant techniques exemplified herein.

The invention also provides methods for studying the function of the AL-2 protein. Cells, tissues, and non-human animals lacking AL-2 expression, partially lacking in AL-2 expression, or over-expressing AL-2 can be developed using recombinant molecules of the invention having specific deletion or insertion mutations in the AL-2 gene. For example, the extracellular domain or parts thereof, the transmembrane region or parts thereof, and the cytoplasmic domain can be deleted. A recombinant molecule may be used to inactivate or alter the endogenous gene by homologous recombination, and thereby create an AL-2 deficient (or over-expressing) cell, tissue or animal.

Null alleles can be generated in cells, such as embryonic stem cells by deletion mutation. A recombinant AL-2 gene may also be engineered to contain an insertion mutation which inactivates AL-2. Such a construct may then be introduced into a cell, such as an embryonic stem cell, by a technique such as transfection, electroporation, injection, etc. Cells lacking an intact AL-2 gene can then be identified, for example by Southern blotting, Northern blotting or by assaying for expression of AL-2 protein using the methods described herein. Such cells may then be fused to embryonic stem cells to generate transgenic non-human animals deficient in AL-2. Germine transmission of the mutation may be achieved, for example, by aggregating the embryonic stem cells with early stage embryos, such as 8 cell embryos, in vitro; transferring the resulting blastocysts into recipient females and; generating germine transmission of the resulting aggregation chimeras. Such a mutant animal may be used to define specific nerve cell populations, developmental patterns of axonogenesis, neural tube formation and nerve regeneration and in vivo processes, normally dependent on AL-2 expression.

Methods for preparing cells, tissues, and non-human animals lacking in AL-2 expression or partially lacking in AL-2 expression, and deficient in the expression of other genes are provided. In one embodiment, an animal may be generated which is deficient in AL-2 and another tyrosine kinase receptor ligand. Such animals could be used to determine how the members of the family cooperate in embryonic development, particularly development of the nervous system. For example, an animal lacking or partially lacking AL-2 expression and Htk-L expression can be generated to determine how the receptor tyrosine kinases cooperate in neurogenesis, e.g., the segmental patterning of the hindbrain. Multiple deficient mice can also be generated to study the interaction of AL-2 and other proteins such as the ligands of the Src-family of cytoplasmic tyrosine kinases. For example, an animal may be generated which lacks or partially lacks AL-2 expression, and expression of one or more Src family tyrosine kinases including Src or Fyn and their ligands.

The binding characteristics of AL-2 (including variants) can also be determined using purified receptor, e.g., conjugated, soluble receptor (for example, $^{125}$I-Htk-Fc or Hek5-IgG) in competition assays as described herein. For example, either intact cells expressing AL-2 or soluble AL-2 bound to a solid substrate are used to measure the extent to which a sample containing a putative AL-2-receptor competes for binding of a conjugated soluble receptor to AL-2.

The AL-2 of the present invention can be used in a binding assay to detect cells expressing an Eph-family receptor that binds AL-2. For example, AL-2 or an extracellular domain or a fragment thereof can be conjugated to a detectable moiety such as $^{125}$I. Radiolabeling with $^{125}$I can be performed by any of several standard methodologies that yield a functional $^{125}$I-AL-2 molecule labeled to high specific activity. Alternatively, another detectable moiety such as an enzyme that can catalyze a calorimetric or fluorometric reaction, biotin or avidin may be used. Cells or samples to be tested for AL-2-receptor expression can be contacted with labeled AL-2. After incubation, unbound labeled AL-2 is removed and binding is measured using the detectable moiety.

The AL-2 proteins disclosed herein can be employed to measure the biological activity of an AL-2 receptor in terms of binding affinity for AL-2. For example, AL-2 can be employed in a binding affinity study to measure the biological activity of a receptor that has been stored at different temperatures, or produced in different cell types. Thus, AL-2 proteins find use as reagents in "quality assurance" studies, e.g., to monitor shelf life and stability of receptor protein under different conditions. Furthermore, AL-2 can be used in determining whether biological activity is retained after modification of a receptor protein (e.g., chemical modification, truncation, mutation, etc.). The binding affinity of the modified receptor for an AL-2 is compared to that of an unmodified receptor to detect any adverse impact of the modifications on biological activity of the receptor.

Binding of AL-2 to an Eph-family receptor can be determined using conventional techniques, including competitive binding methods, such as RIAs, ELISAs, and other competitive binding assays. Ligand/receptor complexes can be identified using such separation methods as filtration, centrifugation, flow cytometry (see, e.g., Lyman et al., *Cell* 75:1157–1167 (1993); Urdal et al., *J. Biol. Chem.* 263:2870–2877 (1988); and Gearing et al., *EMBO J.* 8:3667–3676 (1989)). Results from binding studies can be analyzed using any conventional graphical representation of the binding data, such as Scatchard analysis (Scatchard, *Ann. NY Acad. Sci.* 51:660–672 (1949); and Goodwin et al., *Cell* 73:447–456 (1993)), and the like. Since the AL-2 induces receptor phosphorylation, conventional tyrosine phosphorylation assays can also be used.

Isolated AL-2 polypeptide may be used in quantitative diagnostic assays as a standard or control against which samples containing unknown quantities of AL-2 may be prepared.

AL-2 preparations are also useful in generating antibodies, as standards in assays for AL-2 (e.g., by labeling AL-2 for use as a standard in a radioimmunoassay, or enzyme-linked immunoassay), for detecting the presence of an AL-2-receptor in a biological sample (e.g., using a labelled AL-2), in affinity purification techniques, and in competitive-type receptor binding assays when labeled for example with radioiodine, enzymes, fluorophores, spin labels, or branched DNA.

AL-2 polypeptide can be produced in prokaryotic cells using the techniques taught herein, and the unglycosylated protein so produced can be used as a molecular weight marker, for example. Preferably unglycosylated, soluble AL-2 is used. AL-2 can be used as a molecular weight marker in gel filtration chromatography or SDS-PAGE, for example, either analytical or preparative modes, where it is desirable to determine molecular weight(s) for separated peptides. AL-2 is most preferably used in combination with other known molecular weight markers as standards to provide a range of molecular weights. Other known molecular weight markers can be purchased commercially, e.g., from Amersham Corporation, Arlington Heights, Ill., for example. The molecular weight markers can be labelled to enable easy detection following separation. Techniques for labelling antibodies and proteins are discussed herein and are well known in the art. For example, the molecular weight markers can be biotinylated and, following separation on SDS-PAGE, for example, can be detected using streptavidin-horseradish peroxidase.

AL-2 is used for competitive screening of potential agonists or antagonists for binding to an AL-2 receptor. AL-2 variants are useful as standards or controls in assays for AL-2, provided that they are recognized by the analytical system employed, e.g., an anti-AL-2 antibody.

One embodiment is a method for identifying compounds that modulate the activity of an AL-2-binding-Eph-family receptor. The method includes the steps of (a) exposing cells exhibiting the receptor to ligand, i.e., AL-2 or modified or variant forms, for a time sufficient to allow formation of receptor-ligand complexes and induce signal transduction, (b) determining the extent of activity within the cells, and (c) comparing the measured activity to the activity in cells not exposed to the ligand. Receptor activity may be detected by changes in target cell proliferation, differentiation, metabolism, or other activity of interest (e.g., axon-targeting, neuronal outgrowth), preferably one predictive of success of a therapeutic method. The receptor can be endogenous or can be present as a result of expression of a recombinant molecule.

AL-2 can be useful as a growth factor or differentiation for cells having an AL-2 receptor. These cells, which can be grown ex vivo, can simultaneously be exposed to other known growth factors or cytokines. Exemplary cytokines include the interleukins (e.g., IL-3), granulocyte-macrophage colony-stimulating factor (GM-CSF), macrophage colony-stimulating factor (M-CSF), granulocyte colony-stimulating factor (GM-CSF), erythropoietin (Epo), lymphotoxin, steel factor (SLF), tumor necrosis factor (TNF) and gamma-interferon. This results in proliferation and/or differentiation of the cells having a AL-2 receptor. For example, human tumor cell lines for which it is desired to isolate certain tumor associated factors (usually proteins)

therefrom can be grown ex vivo using AL-2. Also, antibodies against the tumor associated factors can be generated which may be useful for diagnostic purposes. Examples of such tumor cell lines which are candidates for treatment with AL-2 include mammary cancer cells (e.g. MCF-7), liver cell lines, Colo 205, NCI 69, HM-1 and HeLa, for example.

A different use of an AL-2 is as a reagent in protein purification procedures. AL-2 or-AL-2-IgG fusion proteins may be attached to a solid support material by conventional techniques and used to purify an AL-2-binding protein, e.g. receptor, by affinity chromatography. AL-2 can be used for affinity purification of an AL-2 receptor. Briefly, this technique involves covalently attaching AL-2 to an inert and porous matrix (e.g., agarose reacted with cyanogen bromide). A solution containing the AL-2 receptor can then be passed through the chromatographic material and can be subsequently released by changing the elution conditions (e.g. by changing pH or ionic strength).

AL-2 polypeptides find use as carriers for delivering agents to cells bearing an AL-2-binding cell surface receptor. Al-2 can be used to deliver diagnostic or therapeutic agents to these cells (or to other cell types found to express an AL-2 receptor on the cell surface) in in vitro, ex vivo, or in vivo procedures. One example of such use is to expose an AL-2 receptor expressing neoplastic cell line to a therapeutic agent/AL-2 conjugate to assess whether the conjugate exhibits a desired effect on the target cells. A number of different therapeutic agents attached to AL-2 can be included in an assay to detect and compare the effect of the agents on the target cells. In a preferred embodiment the agent is a cytotoxin; however, the agent can be a viral protease inhibitor or the like. In another embodiment, a diagnostic, i.e., detectable agent, is conjugated to AL-2 to detect the presence of AL-2-receptor-expressing cells.

Diagnostic and therapeutic agents that may be attached to a AL-2 polypeptide include, but are not limited to, drugs, toxins, antiviral agents, radionuclides, chromophores, fluorescent compounds, enzymes that catalyze a colorimetric or fluorometric reaction, and the like, with the particular agent being chosen according to the intended application. Examples of drugs include those used in treating various forms of cancer, e.g., nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine, and antibiotics such as bleomycin, doxorubicin, daunorubicin, and derivatives thereof. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Radionuclides suitable for therapeutic use include, but are not limited to, $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to AL-2 by any suitable conventional procedure. AL-2 contains functional groups on amino acid side chains that can be reacted with functional groups on a desired agent to form covalent bonds, for example. Alternatively, the protein or agent may be derivatized to generate or attach a desired reactive functional group, preferably a site-specific reactive group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to AL-2 by using a suitable bifunctional chelating agent, for example.

Conjugates comprising AL-2 and a suitable diagnostic or therapeutic agent (preferably covalently linked) are administered or otherwise employed in an amount appropriate for the particular application.

In view of the sequence identity between AL-2 and Htk-L as shown in FIGS. 4 and 5, which is determined for the first time herein, and since Htk-L is a ligand of the transmembrane-sequence type and binds an Eph-family receptor, namely Htk, the present application provides embodiments of methods of treatment wherein an effective amount of Htk-L is administered to a patient in need of such treatments as discussed for the first time herein for AL-2. Accordingly, WO 96/02645, published Feb. 1, 1996, is incorporated by reference herein for its teachings regarding nucleic acid sequences encoding Htk-L, Htk-L proteins and variants, and methods for their production and formulation. Consequently, it is the intent of the present inventors that new uses and methods of administration of AL-2, as taught for the first time herein, are to be applied to Htk-L. For example, in one embodiment Htk-L will find use in methods of treatment of angiogenesis-related conditions as taught herein for AL-2.

In summary, by providing nucleic acid molecules encoding AL-2, the present invention enables for the first time the production of AL-2 by recombinant DNA methods, thus providing a reliable source of sufficient quantities of AL-2 for use in various diagnostic and therapeutic applications. In view of its distinct biological properties, purified recombinant AL-2 will be especially useful in a variety of circumstances, such as in angiogenesis-related conditions and where it is necessary or desirable to assure neuronal function, growth, survival, or cell-cell contact, but where other neurotrophic factors or angiogenic agents either cannot be used or are less effective.

The following examples are offered by way of illustration only and are not intended to limit the invention in any manner. All patent and literature references cited herein are expressly incorporated.

EXAMPLES

Example 1

Isolation of a Full-length cDNA Encoding AL-2.

The Genbank EST database was screened with an AL-1 sequence and with sequences from several other members of the Eph-receptor ligand family, namely B61, Lerk2 and Htk-L. From this search, EST sequence H10006 was identified (see FIGS. 3A–3B) and selected to provide a sequence from which a probe-based cloning approach for a novel neurotrophic factor was devised.

Two 60-mer oligonucleotide probes were designed based on the sequence of the EST H10006, namely sense-probe-H1006 (5'-GGA CAA AGT CCC GAG GAG GGG CTG TCC CCC GAA AAC CTG TGT CTG AAA TGC CCA TGG AAA-3') (SEQ ID NO:7) and antisense-probe-H1006 (5'-CAG GTT CTC CTT CCC CAG GCT CCC AGG CTG TGG GCT GCC CCT CGG TCT CTT TCC ATG GGC-3') (SEQ ID NO:8) The probes are alternatively referred to as sense-probe-H10006 and anti-sense-probe-H10006, respectively.

Figure 3A:
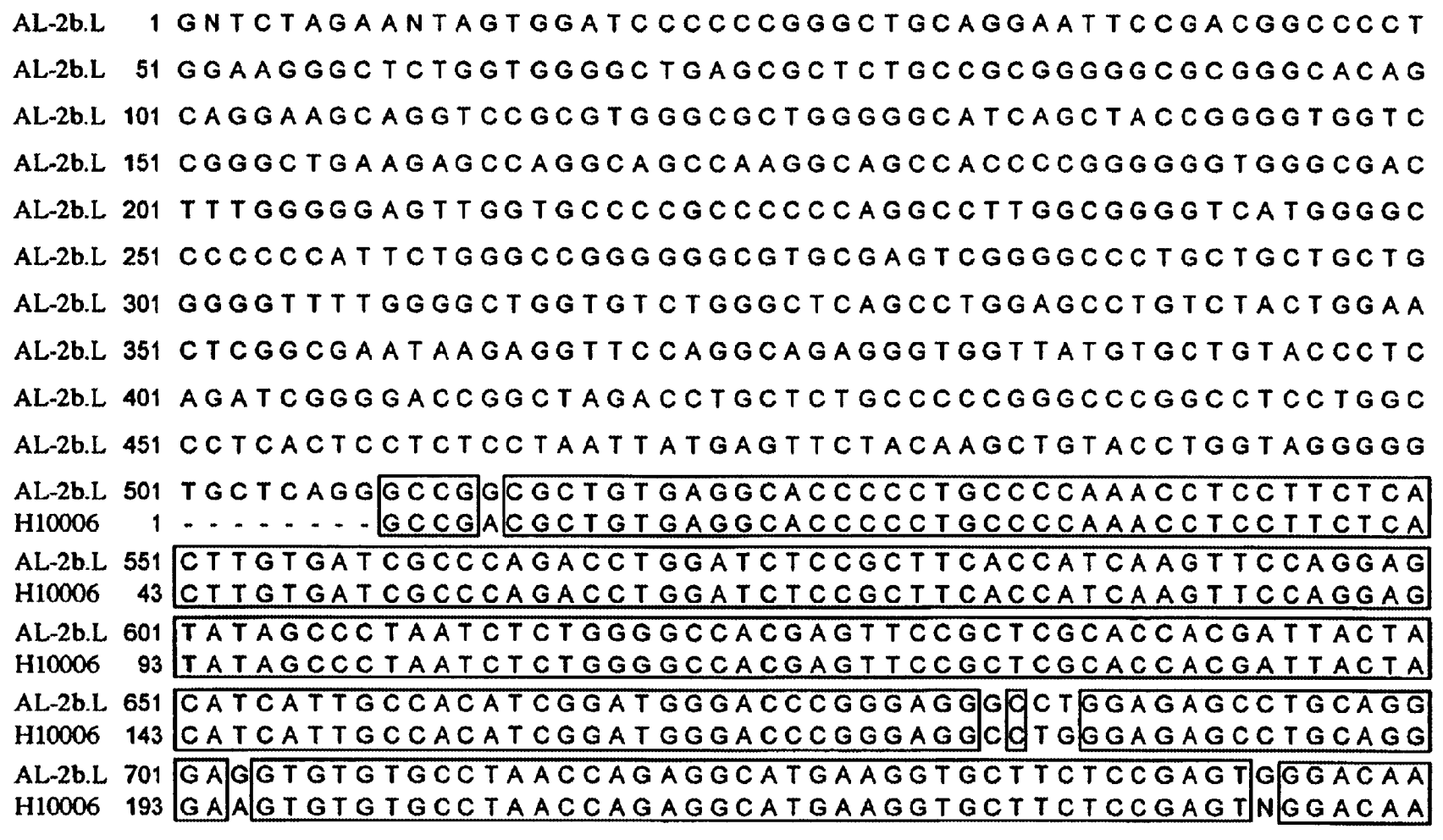

The two synthetic probes were labeled and used to screen a human fetal brain cDNA library. Filters were hybridized in 50% formamide and washed in 0.2% SSC/0.1% SDS at 55° C. Six double-positive clones, i.e., clones that hybridized with both probes, were identified and selected. These clones were plaque purified, and their cDNA inserts were transferred into a plasmid vector and sequenced. Two distinct sequences encoding identical proteins differing only at their C-termini were observed indicating a novel neurotrophic factor designated AL-2. The shorter form, which ends with the sequence "KV," was designated AL-2s ("AL-2-short"), and the longer form, which contains additional amino acids at its C-terminal end, was designated AL-21 ("AL-2-long"). FIGS. 1A–1B depicts the AL-21 cDNA sequence and the deduced AL-21 amino acid sequence. FIGS. 2A–2B depicts the AL-2s cDNA sequence and the deduced AL-2s amino acid sequence. FIGS. 3A–3B depicts alignment of the AL-21 nucleic acid sequence with the EST H10006 sequence.

Example 2

Expression of AL-2 by Northern Blot Analysis

A Northern blot of poly(A)+RNA isolated from pancreas, kidney, skeletal muscle, liver, lung, placenta, brain and heart tissue was screened with an AL-2 probe. The highest levels of AL-2 expression were in the brain, pancreas, and skeletal muscle. Lower levels were detectable in kidney, liver, placenta and heart.

Within the brain AL-2 was expressed in every brain region tested, including cerebellum, cerebral cortex, medulla, spinal cord, occipital pole, frontal lobe, temporal lobe, putamen, amygdala, caudate nucleus, corpus callosum, hippocampus, whole brain, substantia nigra, subthalamic nucleus and thalamus. Interestingly, a second, shorter RNA transcript was observed in the brain samples. The shorter transcript may be the AL-2s mRNA. The ratio between the observed long and short transcripts differed amongst the brain regions screened.

Example 3

Construction and Production of an AL-2-IgG Fusion

A soluble AL-2-IgG fusion protein was constructed by recombinant DNA techniques. DNA encoding a soluble AL-2-IgG chimera was constructed by joining the DNAs encoding the extracellular domain of AL-2 and the Fc domain of $IgG_1$, similar to the construction of Rek7-IgG and AL-1-IgG (see Winslow et al., Neuron, 14:973–981 (1995)), with the AL-2 sequence replacing the AL-1 sequence. The AL-2 coding region from its initiation methionine-1 to glycine-218 was fused at its 3' end to the 5'-end (at the aspartic acid) of the 343 amino acid sequence of IgG2b.

AL-2-IgG fusion protein is generated by transfection of HEK 293 cells (Graham, et al., J. Gen. Virol. 36:59 (1977)) with the plasmid pRKAL-2-IgG under conditions as described by Winslow et al., Neuron, 14:973–981 (1995)). Conditioned media is collected after 3 days and AL-2-IgG is purified by Protein A chromatography.

Example 4

Biological Activity: Activation of Eph-Related Receptors by AL-2

The ability of AL-2 or variant, e.g., AL-2-IgG, to activate a Eph-family receptor can be determined by tyrosine autophosphorylation of the receptor in a receptor-expressing cell source as described herein. Cells expressing an Eph-family receptor, preferably Hek2, Hek5, Hek6/elk/Cek6, or Htk, are incubated with AL-2 and specific phosphorylation of the Eph-family receptor is monitored. Specific phosphorylation indicates that AL-2 not only binds to the Eph-family receptor, but that it also activates the Eph-family receptor.

Cells expressing an Eph-family receptor, e.g., cultured primary cortical neurons, are detected and analyzed by in situ hybridization and/or immunoprecipitation and immunoblotting with anti-Eph-family-receptor antibodies, preferably anti-Hek2, anti-Elk/Hek6/Cek6, anti-Hek5 or anti-Htk, and anti-phosphotyrosine antibodies. Membrane-bound AL-2 is transiently expressed on the surface of transfected 293 cells and its activation of the endogenous Eph-family receptor in the receptor-expressing cell is monitored. Activation of endogenous Eph-family receptor is indicated by autophosphorylation of the receptor. Alternatively, soluble AL-2 fusion, e.g., AL-2-IgG, dimers, multimers, as taught herein, is provided to the receptor-expressing cells and tested for activation of endogenous Eph-family receptor as described, for example, by Winslow et al., Neuron, 14:973–981 (1995). Membrane-attachment has been reported as required or preferred for maximal receptor activation with other members of this ligand family (Davis et al., Science, 266:816–819 (1994)).

HEK 293 cells are transfected with an AL-2 cDNA expression plasmid using the calcium phosphate coprecipitation method (Simonsen et al., Proc. Natl. Acad. Sci. USA, 80:2495–2499 (1983)). Primary cortical neurons from E16 rats are plated at a density of $5 \times 10^6$ cells/15 cm dish and cultured for 4 days. These cells are then treated with purified soluble AL-2 or soluble AL-2-IgG (0.1–1 $\mu$g/ml) or a number of 293 cells expressing an equivalent number of membrane-bound AL-2 for 10 min at 37° C. Immunoprecipitation of lysates with rabbit anti-Eph-family receptors and immunoblotting with mouse anti-phosphotyrosine is essentially as described (Kaplan et al., Science, 252:554–559 (1991); Kaplan et al., Nature, 350:158–160 (1991)). Immunoblotted bands are visualized using a horseradish peroxidase-conjugated sheep anti-mouse antibody and the ECL fluorescence detection system (Amersham) as described by the manufacturer.

An ability of AL-2-IgG to activate the autophosphorylation of receptor, preferably to a similar extent as membrane-bound AL-2, indicates that the soluble AL-2-IgG fusion protein and the like can be used as an agonist for Eph-family receptors in vitro, ex vivo, and in vivo. An inability of soluble AL-2 (e.g., free ECD) to activate receptor autophosphorylation despite its ability to bind receptor indicates that certain soluble forms of AL-2 as taught herein can act as antagonists of Eph-family receptors.

What is claimed is:

1. An isolated nucleic acid comprising a nucleotide sequence encoding the extracellular domain of AL-2 as set forth by amino acids 27–219 of SEQ ID NO:2 fused to an immunoglobulin amino acid sequence.

2. An isolated nucleic acid comprising a nucleotide sequence encoding the amino acid sequence for mature AL-21 of SEQ ID NO:2 fused to an immunoglobulin amino acid sequence.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:

```
        (A) LENGTH: 1877 base pairs
        (B) TYPE: Nucleic Acid
        (C) STRANDEDNESS: Double
        (D) TOPOLOGY: Linear (ix) FEATURE:
        (A) NAME/KEY: Extra Cellular Domain
        (B) LOCATION: 244-899
        (C) IDENTIFICATION METHOD:
        (D) OTHER INFORMATION:

(ix) FEATURE:
        (A) NAME/KEY: Transmembrane Domain
        (B) LOCATION: 901-978
        (C) IDENTIFICATION METHOD:
        (D) OTHER INFORMATION:

(ix) FEATURE:
        (A) NAME/KEY: signal peptide
        (B) LOCATION: 244-321
        (C) IDENTIFICATION METHOD:
        (D) OTHER INFORMATION:

(xi) SEQUENCE DESCRIPTION: SEQ ID NO:1:

GNTCTAGAAN TAGTGGATCC CCCCGGGCTG CAGGAATTCC GACGGCCCCT              50

GGAAGGGCTC TGGTGGGGCT GAGCGCTCTG CCGCGGGGGC GCGGGCACAG             100

CAGGAAGCAG GTCCGCGTGG GCGCTGGGGG CATCAGCTAC CGGGGTGGTC             150

CGGGCTGAAG AGCCAGGCAG CCAAGGCAGC CACCCCGGGG GGTGGGCGAC             200

TTTGGGGGAG TTGGTGCCCC GCCCCCCAGG CCTTGGCGGG GTC ATG                246
                                                  Met
                                                   1

GGG CCC CCC CAT TCT GGG CCG GGG GGC GTG CGA GTC GGG                285
Gly Pro Pro His Ser Gly Pro Gly Gly Val Arg Val Gly
            5                  10

GCC CTG CTG CTG CTG GGG GTT TTG GGG CTG GTG TCT GGG                324
Ala Leu Leu Leu Leu Gly Val Leu Gly Leu Val Ser Gly
 15                  20                  25

CTC AGC CTG GAG CCT GTC TAC TGG AAC TCG GCG AAT AAG                363
Leu Ser Leu Glu Pro Val Tyr Trp Asn Ser Ala Asn Lys
         30                  35                  40

AGG TTC CAG GCA GAG GGT GGT TAT GTG CTG TAC CCT CAG                402
Arg Phe Gln Ala Glu Gly Gly Tyr Val Leu Tyr Pro Gln
                 45                  50

ATC GGG GAC CGG CTA GAC CTG CTC TGC CCC CGG GCC CGG                441
Ile Gly Asp Arg Leu Asp Leu Leu Cys Pro Arg Ala Arg
         55                  60                  65

CCT CCT GGC CCT CAC TCC TCT CCT AAT TAT GAG TTC TAC                480
Pro Pro Gly Pro His Ser Ser Pro Asn Tyr Glu Phe Tyr
                 70                  75

AAG CTG TAC CTG GTA GGG GGT GCT CAG GGC CGG CGC TGT                519
Lys Leu Tyr Leu Val Gly Gly Ala Gln Gly Arg Arg Cys
 80                  85                  90

GAG GCA CCC CCT GCC CCA AAC CTC CTT CTC ACT TGT GAT                558
Glu Ala Pro Pro Ala Pro Asn Leu Leu Leu Thr Cys Asp
         95                 100                 105

CGC CCA GAC CTG GAT CTC CGC TTC ACC ATC AAG TTC CAG                597
Arg Pro Asp Leu Asp Leu Arg Phe Thr Ile Lys Phe Gln
                110                 115

GAG TAT AGC CCT AAT CTC TGG GGC CAC GAG TTC CGC TCG                636
Glu Tyr Ser Pro Asn Leu Trp Gly His Glu Phe Arg Ser
 120                 125                 130

CAC CAC GAT TAC TAC ATC ATT GCC ACA TCG GAT GGG ACC                675
His His Asp Tyr Tyr Ile Ile Ala Thr Ser Asp Gly Thr
```

-continued

|  |  |
|---|---|
| CGG GAG GGC CTG GAG AGC CTG CAG GGA GGT GTG TGC CTA<br>Arg Glu Gly Leu Glu Ser Leu Gln Gly Gly Val Cys Leu<br>145                   150                   155 | 714 |
| ACC AGA GGC ATG AAG GTG CTT CTC CGA GTG GGA CAA AGT<br>Thr Arg Gly Met Lys Val Leu Leu Arg Val Gly Gln Ser<br>        160                   165                 170 | 753 |
| CCC CGA GGA GGG GCT GTC CCC CGA AAA CCT GTG TCT GAA<br>Pro Arg Gly Gly Ala Val Pro Arg Lys Pro Val Ser Glu<br>                  175                   180 | 792 |
| ATG CCC ATG GAA AGA GAC CGA GGG GCA GCC CAC AGC CTG<br>Met Pro Met Glu Arg Asp Arg Gly Ala Ala His Ser Leu<br>185                   190                   195 | 831 |
| GAG CCT GGG AAG GAG AAC CTG CCA GGT GAC CCC ACC AGC<br>Glu Pro Gly Lys Glu Asn Leu Pro Gly Asp Pro Thr Ser<br>        200                   205 | 870 |
| AAT GCA ACC TCC CGG GGT GCT GAA GGC CCC CTG CCC CCT<br>Asn Ala Thr Ser Arg Gly Ala Glu Gly Pro Leu Pro Pro<br>210                   215                   220 | 909 |
| CCC AGC ATG CCT GCA GTG GCT GGG GCA GCA GGG GGG CTG<br>Pro Ser Met Pro Ala Val Ala Gly Ala Ala Gly Gly Leu<br>        225                   230                 235 | 948 |
| GCG CTG CTC TTG CTG GGC GTG GCA GGG GCT GGG GGT GCC<br>Ala Leu Leu Leu Leu Gly Val Ala Gly Ala Gly Gly Ala<br>                  240                   245 | 987 |
| ATG TGT TGG CGG AGA CGG CGG GCC AAG CCT TCG GAG AGT<br>Met Cys Trp Arg Arg Arg Arg Ala Lys Pro Ser Glu Ser<br>250                   255                   260 | 1026 |
| CGC CAC CCT GGT CCT GGC TCC TTC GGG AGG GGA GGG TCT<br>Arg His Pro Gly Pro Gly Ser Phe Gly Arg Gly Gly Ser<br>        265                   270 | 1065 |
| CTG GGC CTG GGG GGT GGA GGT GGG ATG GGA CCT CGG GAG<br>Leu Gly Leu Gly Gly Gly Gly Met Gly Pro Arg Glu<br>275                     280                   285 | 1104 |
| GCT GAG CCT GGG GAG CTA GGG ATA GCT CTG CGG GGT GGC<br>Ala Glu Pro Gly Glu Leu Gly Ile Ala Leu Arg Gly Gly<br>            290                   295                   300 | 1143 |
| GGG GCT GCA GAT CCC CCC TTC TGC CCC CAC TAT GAG AAG<br>Gly Ala Ala Asp Pro Pro Phe Cys Pro His Tyr Glu Lys<br>                  305                   310 | 1182 |
| GTG AGT GGT GAC TAT GGG CAT CCT GTG TAT ATC GTG CAG<br>Val Ser Gly Asp Tyr Gly His Pro Val Tyr Ile Val Gln<br>        315                   320                   325 | 1221 |
| GAT GGG CCC CCC CAG AGC CCT CCA AAC ATC TAC TAC ACA<br>Asp Gly Pro Pro Gln Ser Pro Pro Asn Ile Tyr Tyr Thr<br>                  330                   335 | 1260 |
| TCG ATT TCT GTG TTG GAG TGG CCC ATA TTG CAT ACG ATA<br>Ser Ile Ser Val Leu Glu Trp Pro Ile Leu His Thr Ile<br>340                   345                   350 | 1299 |
| CAA CTG TTT TTC ATG CGA TCC AAG TGC TCC CGT GTC ACT<br>Gln Leu Phe Phe Met Arg Ser Lys Cys Ser Arg Val Thr<br>                  355                   360                   365 | 1338 |
| ACA TTC TTA TTT CCT GTG CAA GTT ATT ACG ACA TCG ACT<br>Thr Phe Leu Phe Pro Val Gln Val Ile Thr Thr Ser Thr<br>                        370                   375 | 1377 |
| TGC CGG ATG ACT TCA TTT AGC TTT ACC ACC CTG AAC CCA<br>Cys Arg Met Thr Ser Phe Ser Phe Thr Thr Leu Asn Pro<br>380                   385                   390 | 1416 |
| TCC ATG CAG GCC TGC AGA GCA CAG ATG GGG GAA TTC CGA | 1455 |

-continued

```
Ser Met Gln Ala Cys Arg Ala Gln Met Gly Glu Phe Arg
            395                 400
ATC AGA TGG TGT TTC TGG GGG GAC AGG ATC CTG GGT ACG           1494
Ile Arg Trp Cys Phe Trp Gly Asp Arg Ile Leu Gly Thr
405             410                 415
GCT CTG TTT GTG CTT GTG CTT ATT CTT CTT CTT GGG AGG           1533
Ala Leu Phe Val Leu Val Leu Ile Leu Leu Leu Gly Arg
            420                 425             430
CTG AAT ATG CAT CAG ACG ACA CTG CTC CGG CAA CGG GCC           1572
Leu Asn Met His Gln Thr Thr Leu Leu Arg Gln Arg Ala
                435                 440
AGT GTG GAG GCG GAA GCC GGC CAG CAT GGT CCC CTG TG            1610
Ser Val Glu Ala Glu Ala Gly Gln His Gly Pro Leu
445                 450                 455
ATAGGATTGA AAGAGCTACT GAGAATAGGG GGCTTCTCAA TGAGAGAGCG         1660
GAGGCTGCTG TTATCATGGG AACCAGGCAG ATCAATCATC CCTGGCAGGT         1710
CAGGCAGGAA GTTACTTAGC TTCTCCTTCA CCTTCTTCCC ACAGAATTTA         1760
TTATAGGCTT GTTCCAAGTT GTAGTGTGTG ATCAGATTCG TGCTGCCTGT         1810
CAGCTCTGTG CTACCTGGCA GTTCCCCTCA TGGAATTCGA TATCAAGCTT         1860
ATCGATACCG TCGACCT                                            1877
```

(2) INFORMATION FOR SEQ ID NO:2:

(i) SEQUENCE CHARACTERISTICS:
       (A) LENGTH: 455 amino acids
       (B) TYPE: Amino Acid
       (D) TOPOLOGY: Linear (xi) SEQUENCE DESCRIPTION: SEQ ID NO:2:

```
Met Gly Pro Pro His Ser Gly Pro Gly Gly Val Arg Val Gly Ala
1               5                   10                  15
Leu Leu Leu Leu Gly Val Leu Gly Leu Val Ser Gly Leu Ser Leu
                20                  25                  30
Glu Pro Val Tyr Trp Asn Ser Ala Asn Lys Arg Phe Gln Ala Glu
                35                  40                  45
Gly Gly Tyr Val Leu Tyr Pro Gln Ile Gly Asp Arg Leu Asp Leu
                50                  55                  60
Leu Cys Pro Arg Ala Arg Pro Gly Pro His Ser Ser Pro Asn
                65                  70                  75
Tyr Glu Phe Tyr Lys Leu Tyr Leu Val Gly Ala Gln Gly Arg
                80                  85                  90
Arg Cys Glu Ala Pro Pro Ala Pro Asn Leu Leu Leu Thr Cys Asp
                95                  100                 105
Arg Pro Asp Leu Asp Leu Arg Phe Thr Ile Lys Phe Gln Glu Tyr
                110                 115                 120
Ser Pro Asn Leu Trp Gly His Glu Phe Arg Ser His His Asp Tyr
                125                 130                 135
Tyr Ile Ile Ala Thr Ser Asp Gly Thr Arg Glu Gly Leu Glu Ser
                140                 145                 150
Leu Gln Gly Gly Val Cys Leu Thr Arg Gly Met Lys Val Leu Leu
                155                 160                 165
Arg Val Gly Gln Ser Pro Arg Gly Gly Ala Val Pro Arg Lys Pro
                170                 175                 180
Val Ser Glu Met Pro Met Glu Arg Asp Arg Gly Ala Ala His Ser
                185                 190                 195
```

-continued

```
Leu Glu Pro Gly Lys Glu Asn Leu Pro Gly Asp Pro Thr Ser Asn
            200                 205                 210

Ala Thr Ser Arg Gly Ala Glu Gly Pro Leu Pro Pro Ser Met
            215                 220                 225

Pro Ala Val Ala Gly Ala Ala Gly Leu Ala Leu Leu Leu
            230                 235                 240

Gly Val Ala Gly Ala Gly Ala Met Cys Trp Arg Arg Arg
            245                 250                 255

Ala Lys Pro Ser Glu Ser Arg His Pro Gly Pro Gly Ser Phe Gly
            260                 265                 270

Arg Gly Gly Ser Leu Gly Leu Gly Gly Gly Gly Met Gly Pro
            275                 280                 285

Arg Glu Ala Glu Pro Gly Glu Leu Gly Ile Ala Leu Arg Gly Gly
            290                 295                 300

Gly Ala Ala Asp Pro Pro Phe Cys Pro His Tyr Glu Lys Val Ser
            305                 310                 315

Gly Asp Tyr Gly His Pro Val Tyr Ile Val Gln Asp Gly Pro Pro
            320                 325                 330

Gln Ser Pro Pro Asn Ile Tyr Tyr Thr Ser Ile Ser Val Leu Glu
            335                 340                 345

Trp Pro Ile Leu His Thr Ile Gln Leu Phe Phe Met Arg Ser Lys
            350                 355                 360

Cys Ser Arg Val Thr Thr Phe Leu Phe Pro Val Gln Val Ile Thr
            365                 370                 375

Thr Ser Thr Cys Arg Met Thr Ser Phe Ser Phe Thr Thr Leu Asn
            380                 385                 390

Pro Ser Met Gln Ala Cys Arg Ala Gln Met Gly Glu Phe Arg Ile
            395                 400                 405

Arg Trp Cys Phe Trp Gly Asp Arg Ile Leu Gly Thr Ala Leu Phe
            410                 415                 420

Val Leu Val Leu Ile Leu Leu Leu Gly Arg Leu Asn Met His Gln
            425                 430                 435

Thr Thr Leu Leu Arg Gln Arg Ala Ser Val Glu Ala Glu Ala Gly
            440                 445                 450

Gln His Gly Pro Leu
            455

(2) INFORMATION FOR SEQ ID NO:3:

(i) SEQUENCE CHARACTERISTICS:
        (A) LENGTH: 2380 base pairs
        (B) TYPE: Nucleic Acid
        (C) STRANDEDNESS: Single
        (D) TOPOLOGY: Linear (xi) SEQUENCE DESCRIPTION: SEQ ID NO:3:

GNTCTAGAAN TAGTGGATCC CCCCGGGCTG CAGGAATTCC GACGGCCCCT           50

GGAAGGGCTC TGGTGGGGCT GAGCGCTCTG CCGCGGGGGC GCGGGCACAG          100

CAGGAAGCAG GTCCGCGTGG GCGCTGGGGG CATCAGCTAC CGGGGTGGTC          150

CGGGCTGAAG AGCCAGGCAG CCAAGGCAGC CACCCCGGGG GGTGGGCGAC          200

TTTGGGGGAG TTGGTGCCCC GCCCCCCAGG CCTTGGCGGG GTCATGGGGC          250

CCCCCCATTC TGGGCCGGGG GGCGTGCGAG TCGGGGCCCT GCTGCTGCTG          300

GGGGTTTTGG GGCTGGTGTC TGGGCTCAGC CTGGAGCCTG TCTACTGGAA          350
```

-continued

| | |
|---|---|
| CTCGGCGAAT AAGAGGTTCC AGGCAGAGGG TGGTTATGTG CTGTACCCTC | 400 |
| AGATCGGGGA CCGGCTAGAC CTGCTCTGCC CCCGGGCCCG GCCTCCTGGC | 450 |
| CCTCACTCCT CTCCTAATTA TGAGTTCTAC AAGCTGTACC TGGTAGGGGG | 500 |
| TGCTCAGGGC CGGCGCTGTG AGGCACCCCC TGCCCCAAAC CTCCTTCTCA | 550 |
| CTTGTGATCG CCCAGACCTG GATCTCCGCT TCACCATCAA GTTCCAGGAG | 600 |
| TATAGCCCTA ATCTCTGGGG CCACGAGTTC CGCTCGCACC ACGATTACTA | 650 |
| CATCATTGCC ACATCGGATG GGACCCGGGA GGGCCTGGAG AGCCTGCAGG | 700 |
| GAGGTGTGTG CCTAACCAGA GGCATGAAGG TGCTTCTCCG AGTGGGACAA | 750 |
| AGTCCCCGAG GAGGGCTGT CCCCCGAAAA CCTGTGTCTG AAATGCCCAT | 800 |
| GGAAAGAGAC CGAGGGGCAG CCCACAGCCT GGAGCCTGGG AAGGAGAACC | 850 |
| TGCCAGGTGA CCCCACCAGC AATGCAACCT CCCGGGGTGC TGAAGGCCCC | 900 |
| CTGCCCCCTC CCAGCATGCC TGCAGTGGCT GGGGCAGCAG GGGGGCTGGC | 950 |
| GCTGCTCTTG CTGGGCGTGG CAGGGCTGG GGGTGCCATG TGTTGGCGGA | 1000 |
| GACGGCGGGC CAAGCCTTCG GAGAGTCGCC ACCCTGGTCC TGGCTCCTTC | 1050 |
| GGGAGGGGAG GGTCTCTGGG CCTGGGGGGT GGAGGTGGGA TGGGACCTCG | 1100 |
| GGAGGCTGAG CCTGGGGAGC TAGGGATAGC TCTGCGGGGT GGCGGGCTG | 1150 |
| CAGATCCCCC CTTCTGCCCC CACTATGAGA AGGTGAGTGG TGACTATGGG | 1200 |
| CATCCTGTGT ATATCGTGCA GGATGGGCCC CCCCAGAGCC CTCCAAACAT | 1250 |
| CTACTACAAG GTATGAGGGC TCCTCTCACG TGGCTATCCT GAATCCAGCC | 1300 |
| CTTCTTGGGG TGCTCCTCCA GTTTAATTCC TGGTTTGAGG ACACCTCTA | 1350 |
| ACATCTCGGC CCCCTGTGCC CCCCAGCCC CTTCACTCCT CCCGGCTGCT | 1400 |
| GTCCTCGTCT CCACTTTTAG GATTCCTTAG GATTCCCACT GCCCCACTTC | 1450 |
| CTGCCCTCCC GTTTGGCCAT GGGTGCCCCC CTCTGTCTCA GTGTCCCTGG | 1500 |
| ATCCTTTTTC CTTGGGGAGG GGCACAGGCT CAGCCTCCTC TCTGACCATG | 1550 |
| ACCCAGGCAT CCTTGTCCCC CTCACCCACC CAGAGCTAGG GGCGGGAACA | 1600 |
| GCCCACCTTT TGGTTGGCAC CGCCTTCTTT CTGCCTCTCA CTGGTTTTCT | 1650 |
| CTTCTCTATC TCTTATTCTT TCCCTCTCTT CCGTCTCTAG GTCTGTTCTT | 1700 |
| CTTCCCTAGC ATCCTCCTCC CCACATCTCC TTTCACCCTC TTGGCTTCTT | 1750 |
| ATCCTGTGCC TCTCCCATCT CCTGGGTGGG GGCATCAAAG CATTTCTCCC | 1800 |
| CTTAGCTTTC AGCCCCCCTT CTGACCTCTC ATACCAACCA CTCCCCTCAG | 1850 |
| TCTGCCAAAA ATGGGGGCCT TATGGGGAAG GCTCTGACAC TCCACCCCAG | 1900 |
| CTCAGGCCAT GGGCAGCAGG GCTCCATTCT CTGGCCTGGC CCAGGCCTCT | 1950 |
| ACATACTTAC TCCAGCCATT TGGGGTGGTT GGGTCATGAC AGCTACCATG | 2000 |
| AGAAGAAGTG TCCCGTTTTG TCCAGTGGCC AATAGCAAGA TATGAACCGG | 2050 |
| TCGGGACATG TATGGACTTG GTCTGATGCT GAATGGGCCA CTTGGGACCG | 2100 |
| GAAGTGACTT GCTCCAGACA AGAGGTGACC AGGCCCGGAC AGAAATGGCC | 2150 |
| TGGGAAGTAG CAGAAGCAGT GCAGCAGGAA CTGGAAGTGC CTTCATCCAG | 2200 |
| GACAGGAAGT AGCACTTCTG AAACAGGAAG TGGTCTGGCT GGAACTCCAA | 2250 |
| GTGGCTTAGT CTGGGGATC AGGAGGTGGG AGGTGGATGG TTCTTATTCT | 2300 |

```
GTGGAGAAGA AGGGCGGGAA GAACTTCCTT TCAGGAGGAA GCTGGAACTT       2350

ACTGACTGTA AGAGGTTAGA GGTGGACCGA                             2380
```

(2) INFORMATION FOR SEQ ID NO:4:

(i) SEQUENCE CHARACTERISTICS:
        (A) LENGTH: 340 amino acids
        (B) TYPE: Amino Acid
        (D) TOPOLOGY: Linear (xi) SEQUENCE DESCRIPTION: SEQ ID NO:4:

```
Met Gly Pro Pro His Ser Gly Pro Gly Gly Val Arg Val Gly Ala
 1               5                  10                  15

Leu Leu Leu Leu Gly Val Leu Gly Leu Val Ser Gly Leu Ser Leu
                20                  25                  30

Glu Pro Val Tyr Trp Asn Ser Ala Asn Lys Arg Phe Gln Ala Glu
                35                  40                  45

Gly Gly Tyr Val Leu Tyr Pro Gln Ile Gly Asp Arg Leu Asp Leu
                50                  55                  60

Leu Cys Pro Arg Ala Arg Pro Pro Gly Pro His Ser Ser Pro Asn
                65                  70                  75

Tyr Glu Phe Tyr Lys Leu Tyr Leu Val Gly Gly Ala Gln Gly Arg
                80                  85                  90

Arg Cys Glu Ala Pro Pro Ala Pro Asn Leu Leu Leu Thr Cys Asp
                95                 100                 105

Arg Pro Asp Leu Asp Leu Arg Phe Thr Ile Lys Phe Gln Glu Tyr
               110                 115                 120

Ser Pro Asn Leu Trp Gly His Glu Phe Arg Ser His His Asp Tyr
               125                 130                 135

Tyr Ile Ile Ala Thr Ser Asp Gly Thr Arg Glu Gly Leu Glu Ser
               140                 145                 150

Leu Gln Gly Gly Val Cys Leu Thr Arg Gly Met Lys Val Leu Leu
               155                 160                 165

Arg Val Gly Gln Ser Pro Arg Gly Ala Val Pro Arg Lys Pro
               170                 175                 180

Val Ser Glu Met Pro Met Glu Arg Asp Arg Gly Ala Ala His Ser
               185                 190                 195

Leu Glu Pro Gly Lys Glu Asn Leu Pro Gly Asp Pro Thr Ser Asn
               200                 205                 210

Ala Thr Ser Arg Gly Ala Glu Gly Pro Leu Pro Pro Ser Met
               215                 220                 225

Pro Ala Val Ala Gly Ala Ala Gly Gly Leu Ala Leu Leu Leu Leu
               230                 235                 240

Gly Val Ala Gly Ala Gly Gly Ala Met Cys Trp Arg Arg Arg
               245                 250                 255

Ala Lys Pro Ser Glu Ser Arg His Pro Gly Pro Gly Ser Phe Gly
               260                 265                 270

Arg Gly Gly Ser Leu Gly Leu Gly Gly Gly Gly Met Gly Pro
               275                 280                 285

Arg Glu Ala Glu Pro Gly Glu Leu Gly Ile Ala Leu Arg Gly Gly
               290                 295                 300

Gly Ala Ala Asp Pro Pro Phe Cys Pro His Tyr Glu Lys Val Ser
               305                 310                 315

Gly Asp Tyr Gly His Pro Val Tyr Ile Val Gln Asp Gly Pro Pro
               320                 325                 330
```

```
Gln Ser Pro Pro Asn Ile Tyr Tyr Lys Val
            335                 340
```

(2) INFORMATION FOR SEQ ID NO:5:

(i) SEQUENCE CHARACTERISTICS:
        (A) LENGTH: 454 base pairs
        (B) TYPE: Nucleic Acid
        (C) STRANDEDNESS: Single
        (D) TOPOLOGY: Linear (xi) SEQUENCE DESCRIPTION: SEQ ID NO:5:

```
GCCGACGCTG TGAGGCACCC CCTGCCCCAA ACCTCCTTCT CACTTGTGAT            50

CGCCCAGACC TGGATCTCCG CTTCACCATC AAGTTCCAGG AGTATAGCCC           100

TAATCTCTGG GGCCACGAGT TCCGCTCGCA CCACGATTAC TACATCATTG           150

CCACATCGGA TGGGACCCGG GAGGCCTGGG AGAGCCTGCA GGGAAGTGTG           200

TGCCTAACCA GAGGCATGAA GGTGCTTCTC CGAGTNGGAC AAAGTCCCGA           250

GGAGGGGCTG TCCCCCGAAA ACCTGTGTCT GAAATGCCCA TGGAAAGAGA           300

CCGAGGGGCA GCCCACAGCC TGGGAGCCTG GGAAGGAGA  ACCTGCCAGG           350

TGACCCCACC AGCAATNCAA CCTTCCGGGG TTGCTTGAAG GGCCCCTTGA           400

CCCTTTCCCA GCATTGCNTG CANTTGGTTN GGGGCAGCAN GGGGGNGTTT           450

TGGC                                                             454
```

(2) INFORMATION FOR SEQ ID NO:6:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:6:

```
Asp Lys Thr His Thr Cys Pro Pro Cys Pro
 1               5                   10
```

(2) INFORMATION FOR SEQ ID NO:7:

(i) SEQUENCE CHARACTERISTICS:
        (A) LENGTH: 60 base pairs
        (B) TYPE: Nucleic Acid
        (C) STRANDEDNESS: Single
        (D) TOPOLOGY: Linear (xi) SEQUENCE DESCRIPTION: SEQ ID NO:7:

```
GGACAAAGTC CCGAGGAGGG GCTGTCCCCC GAAAACCTGT GTCTGAAATG            50

CCCATGGAAA                                                        60
```

(2) INFORMATION FOR SEQ ID NO:8:

(i) SEQUENCE CHARACTERISTICS:
        (A) LENGTH: 60 base pairs
        (B) TYPE: Nucleic Acid
        (C) STRANDEDNESS: Single
        (D) TOPOLOGY: Linear (xi) SEQUENCE DESCRIPTION: SEQ ID NO:8:

```
CAGGTTCTCC TTCCCCAGGC TCCCAGGCTG TGGGCTGCCC CTCGGTCTCT            50

TTCCATGGGC                                                        60
```

(2) INFORMATION FOR SEQ ID NO:9:

(i) SEQUENCE CHARACTERISTICS:
        (A) LENGTH: 346 amino acids
        (B) TYPE: Amino Acid
        (D) TOPOLOGY: Linear (xi) SEQUENCE DESCRIPTION: SEQ ID NO:9:

```
Met Ala Arg Pro Gly Gln Arg Trp Leu Gly Lys Trp Leu Val Ala
 1               5                  10                  15

Met Val Val Trp Ala Leu Cys Arg Leu Ala Thr Pro Leu Ala Lys
                20                  25                  30

Asn Leu Glu Pro Val Ser Trp Ser Ser Leu Asn Pro Lys Phe Leu
                35                  40                  45

Ser Gly Lys Gly Leu Val Ile Tyr Pro Lys Ile Gly Asp Lys Leu
                50                  55                  60

Asp Ile Ile Cys Pro Arg Ala Glu Ala Gly Arg Pro Tyr Glu Tyr
                65                  70                  75

Tyr Lys Leu Tyr Leu Val Arg Pro Glu Gln Ala Ala Ala Cys Ser
                80                  85                  90

Thr Val Leu Asp Pro Asn Val Leu Val Thr Cys Asn Arg Pro Glu
                95                 100                 105

Gln Glu Ile Arg Phe Thr Ile Lys Phe Gln Glu Phe Ser Pro Asn
               110                 115                 120

Tyr Met Gly Leu Glu Phe Lys Lys His His Asp Tyr Tyr Ile Thr
               125                 130                 135

Ser Thr Ser Asn Gly Ser Leu Glu Gly Leu Glu Asn Arg Glu Gly
               140                 145                 150

Gly Val Cys Arg Thr Arg Thr Met Lys Ile Ile Met Lys Val Gly
               155                 160                 165

Gln Asp Pro Asn Ala Val Thr Pro Glu Gln Leu Thr Thr Ser Arg
               170                 175                 180

Pro Ser Lys Glu Ala Asp Asn Thr Val Lys Met Ala Thr Gln Ala
               185                 190                 195

Pro Gly Ser Arg Gly Ser Leu Gly Asp Ser Asp Gly Lys His Glu
               200                 205                 210

Thr Val Asn Gln Glu Glu Lys Ser Gly Pro Gly Ala Ser Gly Gly
               215                 220                 225

Ser Ser Gly Asp Pro Asp Gly Phe Phe Asn Ser Lys Val Ala Leu
               230                 235                 240

Phe Ala Ala Val Gly Ala Gly Cys Val Ile Phe Leu Leu Ile Ile
               245                 250                 255

Ile Phe Leu Thr Val Leu Leu Leu Lys Leu Arg Lys Arg His Arg
               260                 265                 270

Lys His Thr Gln Gln Arg Ala Ala Ala Leu Ser Leu Ser Thr Leu
               275                 280                 285

Ala Ser Pro Lys Gly Gly Ser Gly Thr Ala Gly Thr Glu Pro Ser
               290                 295                 300

Asp Ile Ile Ile Pro Leu Arg Thr Thr Glu Asn Asn Tyr Cys Pro
               305                 310                 315

His Tyr Glu Lys Val Ser Gly Asp Tyr Gly His Pro Val Tyr Ile
               320                 325                 330

Val Gln Glu Met Pro Pro Gln Ser Pro Ala Asn Ile Tyr Tyr Lys
               335                 340                 345

Val
```

346

(2) INFORMATION FOR SEQ ID NO:10:

(i) SEQUENCE CHARACTERISTICS:
        (A) LENGTH: 333 amino acids
        (B) TYPE: Amino Acid
        (D) TOPOLOGY: Linear (xi) SEQUENCE DESCRIPTION: SEQ ID NO:10:

```
Met Ala Val Arg Arg Asp Ser Val Trp Lys Tyr Cys Trp Gly Val
 1               5                  10                  15

Leu Met Val Leu Cys Arg Thr Ala Ile Ser Lys Ser Ile Val Leu
                20                  25                  30

Glu Pro Ile Tyr Trp Asn Ser Ser Asn Ser Lys Phe Leu Pro Gly
                35                  40                  45

Gln Gly Leu Val Leu Tyr Pro Gln Ile Gly Asp Lys Leu Asp Ile
                50                  55                  60

Ile Cys Pro Lys Val Asp Ser Lys Thr Val Gly Gln Tyr Glu Tyr
                65                  70                  75

Tyr Lys Val Tyr Met Val Asp Lys Asp Gln Ala Asp Arg Cys Thr
                80                  85                  90

Ile Lys Lys Glu Asn Thr Pro Leu Leu Asn Cys Ala Lys Pro Asp
                95                 100                 105

Gln Asp Ile Lys Phe Thr Ile Lys Phe Gln Glu Phe Ser Pro Asn
               110                 115                 120

Leu Trp Gly Leu Glu Phe Gln Lys Asn Lys Asp Tyr Tyr Ile Ile
               125                 130                 135

Ser Thr Ser Asn Gly Ser Leu Glu Gly Leu Asp Asn Gln Glu Gly
               140                 145                 150

Gly Val Cys Gln Thr Arg Ala Met Lys Ile Leu Met Lys Val Gly
               155                 160                 165

Gln Asp Ala Ser Ser Ala Gly Ser Thr Arg Asn Lys Asp Pro Thr
               170                 175                 180

Arg Arg Pro Glu Leu Glu Ala Gly Thr Asn Gly Arg Ser Ser Thr
               185                 190                 195

Thr Ser Pro Phe Val Lys Pro Asn Pro Gly Ser Ser Thr Asp Gly
               200                 205                 210

Asn Ser Ala Gly His Ser Gly Asn Asn Ile Leu Gly Ser Glu Val
               215                 220                 225

Ala Leu Phe Ala Gly Ile Ala Ser Gly Cys Ile Ile Phe Ile Val
               230                 235                 240

Ile Ile Ile Thr Leu Val Val Leu Leu Leu Lys Tyr Arg Arg Arg
               245                 250                 255

His Arg Lys His Ser Pro Gln His Thr Thr Thr Leu Ser Leu Ser
               260                 265                 270

Thr Leu Ala Thr Pro Lys Arg Ser Gly Asn Asn Asn Gly Ser Glu
               275                 280                 285

Pro Ser Asp Ile Ile Ile Pro Leu Arg Thr Ala Asp Ser Val Phe
               290                 295                 300

Cys Pro His Tyr Glu Lys Val Ser Gly Asp Tyr Gly His Pro Val
               305                 310                 315

Tyr Ile Val Gln Glu Met Pro Pro Gln Ser Pro Ala Asn Ile Tyr
               320                 325                 330
```

-continued

```
Tyr Lys Val
        333
```